United States Patent
Cassayre et al.

(10) Patent No.: US 9,216,973 B2
(45) Date of Patent: *Dec. 22, 2015

(54) INSECTICIDAL COMPOUNDS

(71) Applicants: Syngenta Participations AG, Basel (CH); Syngenta Limited, Guildford Surrey (GB)

(72) Inventors: Jerome Yves Cassayre, Stein (CH); Peter Renold, Stein (CH); Vladimir Bobosik, Bratislava (SK); Myriem El Qacemi, Stein (CH); Anne Jacqueline Dalencon, Berkshire (GB); Werner Zambach, Stein (CH); Christopher Richard Godfrey, Stein (CH); Thomas Pitterna, Stein (CH); Pierre Joseph Jung, Stein (CH); Jagadish Pabba, Goa (IN)

(73) Assignees: Syngenta Participations AG, Basel (CH); Syngenta Limited, Guildford, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/771,829

(22) Filed: Feb. 20, 2013

(65) Prior Publication Data

US 2013/0165485 A1 Jun. 27, 2013

Related U.S. Application Data

(63) Continuation of application No. 13/060,219, filed as application No. PCT/EP2009/059563 on Jul. 24, 2009, now abandoned.

(30) Foreign Application Priority Data

| Aug. 22, 2008 | (GB) | 0815437.9 |
|---|---|---|
| Sep. 4, 2008 | (GB) | 0816133.3 |
| Jan. 14, 2009 | (GB) | 0900561.2 |
| Jan. 22, 2009 | (IN) | 127/DEL/2009 |
| Jan. 29, 2009 | (GB) | 0901508.2 |
| Mar. 20, 2009 | (GB) | 0904868.7 |
| Mar. 26, 2009 | (GB) | 0905239.0 |
| Apr. 24, 2009 | (GB) | 0907122.6 |
| Jun. 22, 2009 | (GB) | 0910767.3 |
| Jun. 22, 2009 | (GB) | 0910768.1 |
| Jun. 22, 2009 | (GB) | 0910769.9 |
| Jun. 22, 2009 | (GB) | 0910771.5 |

(51) Int. Cl.
C07D 413/12 (2006.01)
A01N 43/44 (2006.01)
A01N 43/76 (2006.01)
A01N 43/36 (2006.01)
A01N 43/56 (2006.01)
A01N 43/80 (2006.01)
A01N 43/82 (2006.01)
C07D 409/12 (2006.01)

(Continued)

(52) U.S. Cl.
CPC ........... *C07D 413/12* (2013.01); *A01N 43/36* (2013.01); *A01N 43/44* (2013.01); *A01N 43/56* (2013.01); *A01N 43/76* (2013.01); *A01N 43/80* (2013.01); *A01N 43/82* (2013.01); *C07D 409/12* (2013.01); *C07D 413/14* (2013.01); *C07D 417/14* (2013.01)

(58) Field of Classification Search
CPC .. C07D 413/12; C07D 409/12; C07D 413/14; C07D 417/14; A01N 43/44; A01N 43/76; A01N 43/36; A01N 43/56; A01N 43/80; A01N 43/82

See application file for complete search history.

(56) References Cited

U.S. PATENT DOCUMENTS

2007/0066617 A1 3/2007 Mita et al.

FOREIGN PATENT DOCUMENTS

| EP | 1538138 A | 6/2005 |
|---|---|---|
| EP | 1731512 A | 12/2006 |

(Continued)

OTHER PUBLICATIONS

Diggle A.W., et al., "Pathways in fission of strained rings" Bulletin de la societe chimique de France, Societe Francaise de Chimie, Paris, France, Jan. 1, 1988, p. 317-321.
DERWENT 2010-E08368/33 JP 2010-083883-A machine translation.
DERWENT 2008-L39202/67 JP 2008133273-A machine translation.
DERWENT 2010-J92669/66 JP 2010168367-A machine translation.

*Primary Examiner* — Samantha Shterengarts
(74) *Attorney, Agent, or Firm* — R. Kody Jones

(57) ABSTRACT

A compound of formula (I):

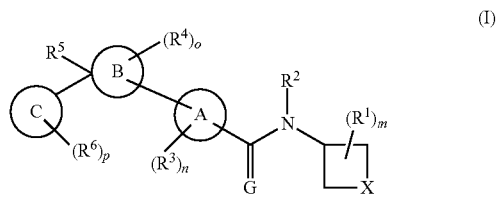

where A, B, C, G, m, n, o, p, $R^1$, $R^2$, $R^3$, $R^4$, $R^5$, $R^6$, X, $R^7$, $R^8$, $R^9$, $R^{10}$ and $R^{11}$ are as defined in claim 1; or a salt or N-oxide thereof.

Furthermore, the present invention relates to processes and intermediates for preparing compounds of formula (I), to insecticidal, acaricidal, nematicidal and molluscicidal compositions comprising the compounds of formula (I) and to methods of using the compounds of formula (I) to control insect, acarine, nematode and mollusc pests.

5 Claims, No Drawings

(51) Int. Cl.
*C07D 413/14* (2006.01)
*C07D 417/14* (2006.01)

(56) References Cited

FOREIGN PATENT DOCUMENTS

| | | |
|---|---|---|
| EP | 1932836 A | 6/2008 |
| EP | 2151437 | 2/2010 |
| EP | 2172448 | 4/2010 |
| EP | 2172462 | 7/2010 |
| JP | 2007/091708 | 4/2007 |
| JP | 2008/133273 | 6/2008 |
| JP | 2008/239611 | 10/2008 |
| JP | 2009/108046 | 5/2009 |
| JP | 2010/83883 | 4/2010 |
| JP | 2010/168367 | 8/2010 |
| WO | 2007/070606 | 6/2007 |
| WO | 2007/075459 | 7/2007 |
| WO | 2007/079162 | 7/2007 |
| WO | 2007/080131 | 7/2007 |
| WO | 2007/093402 | 8/2007 |
| WO | 2009/002809 | 12/2008 |
| WO | 2009/003075 | 12/2008 |
| WO | 2009/154528 | 12/2008 |
| WO | 2009/024541 | 2/2009 |
| WO | 2009/025983 | 2/2009 |
| WO | 2009/063910 | 5/2009 |
| WO | 2009/080250 | 7/2009 |
| WO | 2010/003877 | 1/2010 |
| WO | 2010/003923 | 1/2010 |
| WO | 2010/005048 | 1/2010 |
| WO | 2010/017902 | 2/2010 |
| WO | 2010/020521 | 2/2010 |
| WO | 2010/025998 | 3/2010 |
| WO | 2010/043315 | 4/2010 |
| WO | 2010/079077 | 7/2010 |
| WO | 2010/084067 | 7/2010 |
| WO | 2010/086225 | 8/2010 |
| WO | 2010/108733 | 9/2010 |
| WO | 2010/125130 | 11/2010 |
| WO | 2010/149506 | 12/2010 |

INSECTICIDAL COMPOUNDS

This application is a Continuation of U.S. Ser. No. 13/060,219 which is a 371 of International Application No. PCT/EP2009/059563 filed Jul. 24, 2009, which claims priority to GB 0815437.9 filed Aug. 22, 2008, GB 0816133.3 filed Sep. 4, 2008, 0900561.2 filed Jan. 14, 2009, IN 127/DEL/2009 filed Jan. 22, 2009, GB 0901508.2 filed Jan. 29, 2009, GB 0904868.7 filed Mar. 20, 2009, GB 0905239.0 filed Mar. 26, 2009, GB 0907122.6 filed Apr. 24, 2009, GB 0910768.1 filed Jun. 22, 2009, GB 0910767.3 filed Jun. 22, 2009, GB 0910771.5 filed Jun. 22, 2009, GB 0910769.9 filed Jun. 22, 2009, the contents of which are incorporated herein by reference.

The present invention relates to certain tetracyclic derivatives with a sulfur-containing four-membered ring connected to the nitrogen atom of the amide group, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain tetracyclic derivatives with a carbon only four-membered ring connected to the nitrogen atom of the amide group are disclosed in, for example, EP 1,731,512 and US 2007/066617 as having insecticidal properties. Certain tetracyclic derivatives with a sulfur-containing four-membered ring connected to the nitrogen atom of the amide group are disclosed in, for example, PCT/EP2008/010701 as having insecticidal properties. The compounds of PCT/EP2008/010701 have been excluded from the present invention.

It has now been found that further tetracyclic derivatives with a sulfur-containing four-membered ring connected to the nitrogen atom of the amide group have insecticidal properties.

The present invention therefore provides a compound of formula (I)

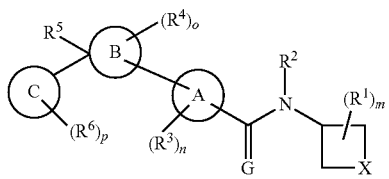

(I)

where
A is aryl or heteroaryl;
B is a saturated or partially unsaturated heterocyclyl;
C is aryl or heteroaryl;
G is oxygen or sulfur;
m is 0, 1, 2, 3, 4 or 5;
n is 0, 1, 2, 3, 4 or 5;
o is 0, 1, 2, 3, 4 or 5;
p is 1, 2, 3, 4 or 5;
each $R^1$ is independently $C_1$-$C_8$alkyl;
$R^2$ is hydrogen, $C_1$-$C_8$alkyl, $C_1$-$C_8$alkylcarbonyl-, or $C_1$-$C_8$alkoxycarbonyl-;
each $R^3$ is independently halogen, cyano, nitro, $C_1$-$C_8$alkyl, $C_1$-$C_8$haloalkyl, $C_2$-$C_8$-alkenyl, $C_2$-$C_8$haloalkenyl, $C_2$-$C_8$-alkynyl, $C_3$-$C_{10}$cycloalkyl, $C_1$-$C_8$-alkoxy-, $C_1$-$C_8$haloalkoxy-, or $C_1$-$C_8$alkoxycarbonyl-;
each $R^4$ is independently halogen, cyano, $C_1$-$C_8$alkyl, $C_1$-$C_8$haloalkyl, hydroxy, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-, or if two $R^4$ are attached to the same carbon atom the two $R^4$ together form $=O$, $=N-OR^7$ or $=CR^8R^9$;

$R^5$ is $C_1$-$C_8$haloalkyl;

each $R^6$ is independently halogen, cyano, nitro, $C_1$-$C_8$alkyl, $C_1$-$C_8$haloalkyl, $C_1$-$C_8$alkoxy-, $C_1$-$C_8$haloalkoxy-, $C_1$-$C_8$alkoxycarbonyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

X is S, SO, $SO_2$, $S(NR^{10})$ or $SO(NR^{10})$;

$R^7$ is hydrogen or $C_1$-$C_4$alkyl;

$R^8$ and $R^9$ are independently of each other hydrogen or $C_1$-$C_4$alkyl;

$R^{10}$ is hydrogen, cyano, nitro, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene- where the aryl moiety is substituted by one to three $R^{11}$, or heteroaryl-$C_1$-$C_4$alkylene- or heteroaryl-$C_1$-$C_4$alkylene- where the heteroaryl moiety is substituted by one to three $R^{11}$, aryl or aryl substituted by one to five $R^{11}$, or heteroaryl or heteroaryl substituted by one to five $R^{11}$; and each $R^{11}$ is independently halogen, cyano, nitro, $C_1$-$C_8$alkyl, $C_1$-$C_8$haloalkyl, $C_1$-$C_8$alkoxy or $C_1$-$C_8$haloalkoxy, or $C_1$-$C_8$alkoxycarbonyl-;

or a salt or an N-oxide thereof;

provided that if A is a group of formula (A.I), (A.II), (A.III), (A.IV) or (A.V)

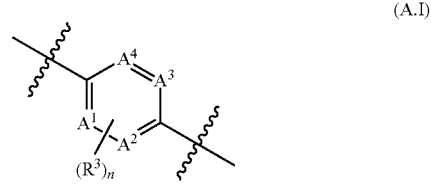
(A.I)

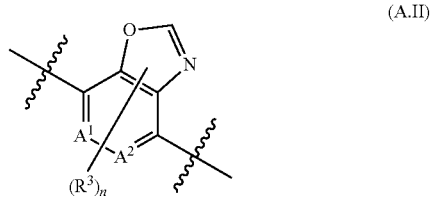
(A.II)

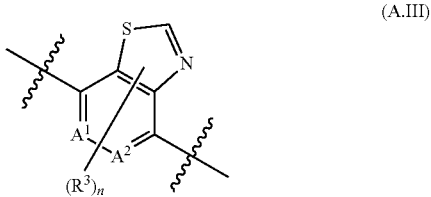
(A.III)

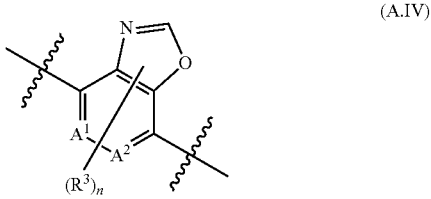
(A.IV)

-continued

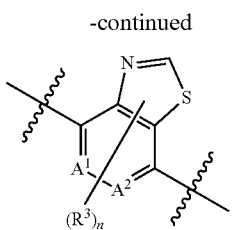
(A.V)

where
A$^1$, A$^2$, A$^3$ and A$^4$ are independently of each other C—H or nitrogen;
n is 0, 1, 2, 3, 4 or 5, and
each R$^3$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_3$-C$_{10}$cycloalkyl, C$_1$-C$_8$alkoxy-, C$_1$-C$_8$haloalkoxy-, or C$_1$-C$_8$alkoxycarbonyl-,
B is not a group of formula (B.VI)

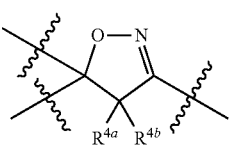
(B.VI)

where R$^{4a}$ and R$^{4b}$ are both hydrogen.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are, unless indicated to the contrary, preferably C$_1$-C$_6$, more preferably C$_1$-C$_4$, most preferably C$_1$-C$_3$ alkyl groups.

Alkylene groups can be in the form of a straight or branched chain and are, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—. The alkylene groups are, unless indicated to the contrary, preferably C$_1$-C$_3$, more preferably C$_1$-C$_2$, most preferably C$_1$ alkylene groups.

Alkenyl groups can be in the form of straight or branched chains, and can be, where appropriate, of either the (E) or (Z) configuration. Examples are vinyl and allyl. The alkenyl groups are, unless indicated to the contrary, preferably C$_2$-C$_6$, more preferably C$_2$-C$_4$, most preferably C$_2$-C$_3$ alkenyl groups.

Alkynyl groups can be in the form of straight or branched chains. Examples are ethynyl and propargyl. The alkynyl groups are, unless indicated to the contrary, preferably C$_2$-C$_6$, more preferably C$_2$-C$_4$, most preferably C$_2$-C$_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl-, haloalkylsulfonyl-, haloalkylcarbonyl- or haloalkoxycarbonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups, unless indicated to the contrary, are preferably C$_3$-C$_8$, more preferably C$_3$-C$_6$ cycloalkyl groups.

Aryl groups are aromatic ring systems which can be in mono, bi or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is, unless indicated to the contrary, preferably substituted by one to four substituents, most preferably by one to three substituents.

Heteroaryl groups are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is, unless indicated to the contrary, preferably substituted by one to four substituents, most preferably by one to three substituents.

Heterocyclyl groups or heterocyclic rings are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is, unless indicated to the contrary, preferably substituted by one to four substituents, most preferably by one to three substituents.

Preferred values for A, A$^1$, A$^2$, A$^3$, A$^4$, A$^5$, A$^6$, B, C, G, m, n, o, p, R$^1$, R$^2$, R$^3$, R$^4$, R$^5$, R$^6$, X, R$^7$, R$^8$, R$^9$, R$^{10}$ and R$^{11}$ are, in any combination, as set out below.

Preferably A is a phenyl or a naphthyl group, or a six-membered monocyclic heteroaryl group, or a bicyclic heteroaryl group which comprises a six-membered ring. More preferably A is a phenyl or a naphthyl group. Where A is bicyclic it is preferred that the B ring and the amide group are connected to the same six-membered ring moiety. Furthermore it is preferred that the B ring and the amide group are attached to in para-position (as shown in the groups of formula (A.I), (A.VI) and (A.VIII) below).

Preferably A is a group of formula (A.I), (A.VI), (A.VII) or (A.VIII)

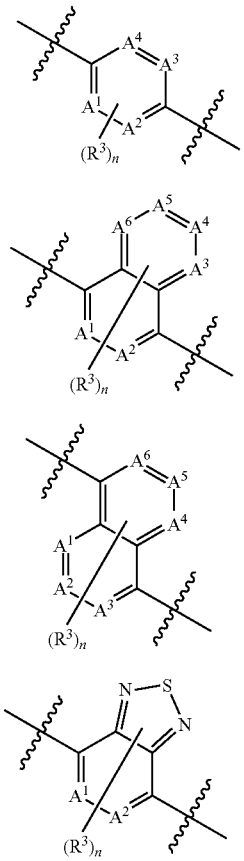

(A.I)

(A.VI)

(A.VII)

(A.VIII)

where
A$^1$, A$^2$, A$^3$, A$^4$, A$^5$ and A$^6$ are independently of each other C—H or nitrogen;
n is 0, 1, 2, 3, 4 or 5, and
each R$^3$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_3$-C$_{10}$cycloalkyl, C$_1$-C$_8$alkoxy-, C$_1$-C$_8$haloalkoxy-, or C$_1$-C$_8$alkoxycarbonyl-.
Preferably no more than two of A$^1$, A$^2$, A$^3$, A$^4$, A$^5$ and A$^6$ are nitrogen.
Preferably A$^1$ is C—H.
Preferably A$^2$ is C—H.
Preferably A$^3$ is C—H.
Preferably A$^4$ is C—H.
Preferably A$^5$ is C—H.
Preferably A$^6$ is C—H.
More preferably A is a group of formula (A.Ia), (A.VIa), (A.VIIa) or (A.VIIIa)

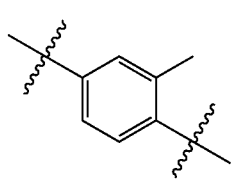

(A.Ia)

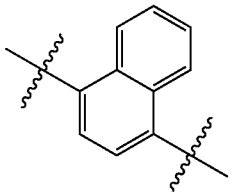

(A.VIa)

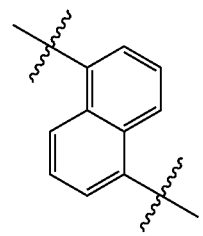

(A.VIIa)

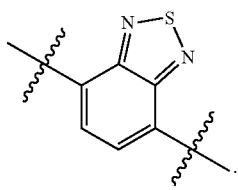

(A.VIIIa)

Preferably B is a three- to five-membered saturated or partially unsaturated heterocyclyl group. More preferably B is a five-membered saturated or partially unsaturated heterocyclyl group.
Preferably B is a group of formula (B.I), (B.II), (B.III), (B.IV), (B.V), (B.VI) or (B.VII)

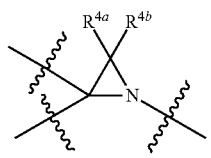

(B.I)

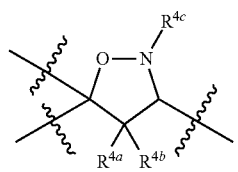

(B.II)

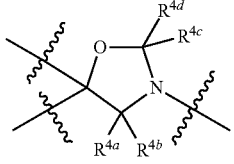

(B.III)

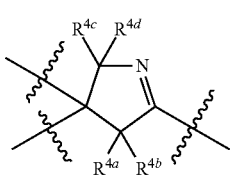

(B.IV)

-continued

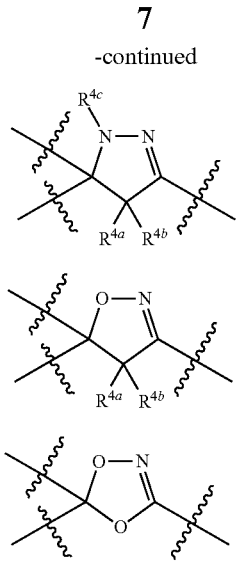

(B.V)

(B.VI)

(B.VII)

where
R$^{4a}$, R$^{4b}$, R$^{4c}$ and R$^{4d}$ are independently of each other hydrogen, halogen, cyano, C$_1$-C$_8$alkyl, C$_1$-C$_1$haloalkyl, hydroxy, C$_1$-C$_8$alkoxy-, C$_1$-C$_8$haloalkoxy-, C$_1$-C$_8$alkylthio-, C$_1$-C$_8$haloalkylthio-, C$_1$-C$_8$ alkylsulfinyl-, C$_1$-C$_8$haloalkylsulfinyl-, C$_1$-C$_8$alkylsulfonyl-, or C$_1$-C$_8$haloalkylsulfonyl-, or
R$^{4a}$ and R$^{4b}$ and/or R$^{4c}$ and R$^{4d}$ when attached to the same carbon atom together form =O, N=OR$^7$ or =CR$^8$R$^9$.

More preferably B is a group of formula (B.Ia), (B.IIa), (B.IIIa), (B.IVa), (B.Va), (B.VIa) or (B.VIIa)

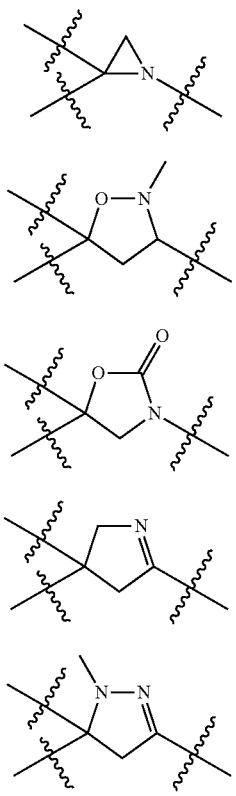

(B.Ia)

(B.IIa)

(B.IIIa)

(B.IVa)

(B.Va)

-continued

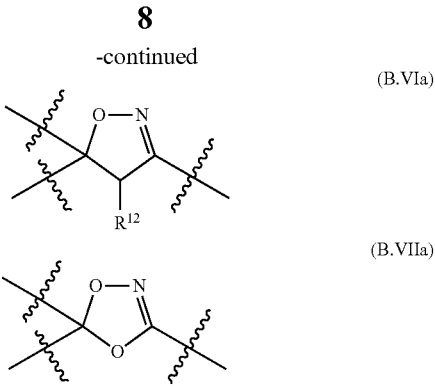

(B.VIa)

(B.VIIa)

where R$^{12}$ is halogen.
Preferably C is a six-membered aryl or heteroaryl group.
Preferably C is a group of formula (C.I)

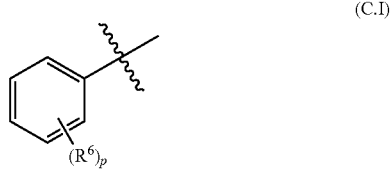

(C.I)

where
p is 1, 2, 3, 4 or 5; and
each R$^6$ is independently halogen, cyano, nitro, C$_1$-C$_8$alkyl, C$_1$-C$_8$haloalkyl, C$_1$-C$_8$alkoxy-, C$_1$-C$_8$haloalkoxy-, C$_1$-C$_8$alkoxycarbonyl-, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl- or C$_1$-C$_8$haloalkylsulfonyl-.
More preferably C is a group of formula (C.Ia)

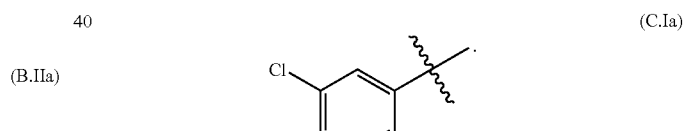

(C.Ia)

Preferably G is oxygen.
Preferably m is 0, 1, 2, 3 or 4.
Preferably n is 0, 1 or 2.
Preferably o is 0, 1 or 2.
Preferably p is 1, 2 or 3.
Preferably each R$^1$ is independently methyl.
Preferably R$^2$ is hydrogen, methyl, ethyl, methylcarbonyl- or methoxycarbonyl-, more preferably hydrogen, methyl or ethyl, most preferably hydrogen.
Preferably each R$^3$ is independently halogen, cyano, C$_1$-C$_8$alkyl, C$_2$-C$_8$alkenyl or C$_1$-C$_8$alkoxy-, more preferably each R$^3$ is independently methyl.
Preferably each R$^4$ is independently halogen, C$_1$-C$_8$alkyl, C$_1$-C$_8$alkylthio-, C$_1$-C$_8$alkylsulfinyl- or C$_1$-C$_8$alkylsulfonyl-, or
if two R$^4$ are attached to the same carbon atom the two R$^4$ together form =O or =CR$^8$R$^9$.
Preferably R$^5$ is chlorodifluoromethyl or trifluoromethyl, most preferably trifluoromethyl.

Preferably each $R^6$ is independently halogen, cyano, nitro, $C_1$-$C_8$alkyl, $C_1$-$C_8$haloalkyl, $C_1$-$C_8$alkoxy-, $C_1$-$C_8$alkylthio-, $C_1$-$C_8$alkylsulfinyl- or $C_1$-$C_8$alkylsulfonyl-.

Preferably X is S, SO or $SO_2$.

Preferably $R^7$ is hydrogen.

Preferably $R^8$ and $R^9$ are independently of each other hydrogen or methyl.

Preferably $R^{10}$ is hydrogen or cyano, more preferably hydrogen.

Preferably each $R^{11}$ is independently fluoro, chloro, cyano, nitro, methyl, trifluoromethyl, methoxy or trifluoromethoxy.

The compounds of the invention may be made by a variety of methods, for example, as shown in Scheme 1.

Scheme 1

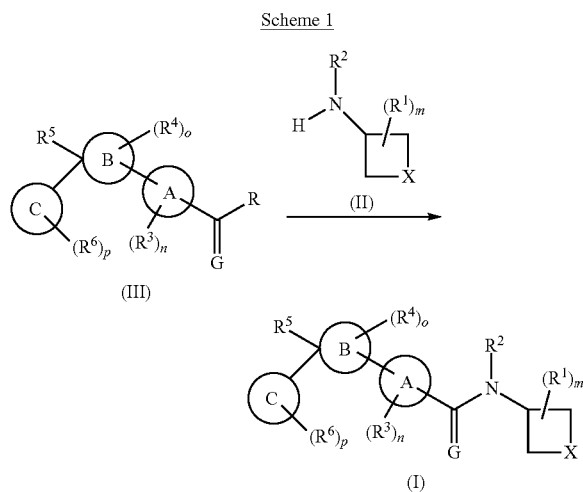

1) A compound of formula (I) where G is oxygen, can be made by reacting a compound of formula (III) where A, B, C, n, o, p, $R^3$, $R^4$, $R^5$ and $R^6$ are as defined for a compound of formula (I), G is oxygen and R is OH, $C_1$-$C_8$alkoxy, or Br, Cl or F, with an amine of formula (II) where m, $R^1$, $R^2$ and X are as defined for a compound of formula (I). When R is OH, such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst. When R is Br, Cl or F, such reactions are usually carried out in the presence of a base, and optionally in the presence of a nucleophilic catalyst. Alternatively, when R is Cl it is possible to conduct the reaction in a biphasic system comprising an organic solvent, preferably ethyl acetate, and an aqueous solvent, preferably a solution of sodium hydrogen carbonate. When R is $C_1$-$C_8$alkoxy, it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Suitable nucleophilic catalysts include hydroxybenzotriazole ("HOBT"). Suitable solvents include dimethylacetamide, tetrahydrofuran, dioxane, 1,2-dimethoxyethane, ethyl acetate and toluene. When R is OH, the reaction is carried out preferably at a temperature of from −20° C. to +200° C., more preferably from 50° C. to 150° C., in particular at 100° C. When R is Br, Cl or F, the reaction is carried out preferably at a temperature of from −20° C. to +50° C., more preferably from 0° C. to 50° C., in particular at ambient temperature. Amines of formula (II) are known from the literature (for example, from WO 2007/080131) or can be made by methods known to a person skilled in the art.

2) Compounds of formula (I) where G is sulfur, can be made by reacting a compound of formula (III) where A, B, C, n, o, p, $R^3$, $R^4$, $R^5$ and $R^6$ are as defined for a compound of formula (I), G is oxygen and R is OH, $C_1$-$C_8$alkoxy, or Br, Cl or F, with a thio-transfer reagent, such as Lawesson's reagent or phosphorus pentasulfide, prior to reacting with the amine of formula (II) as described under 1).

The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*

(vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:
a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidene methyl)cyclopropane carboxylate;
b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad, azadirachtin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, nithiazine or flonicamid;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, spirodiclofen or spiromesifen;
s) Diamides, such as flubendiamide, chlorantraniliprole or cyantraniliprole;
t) Sulfoxaflor; or
u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethyl-benzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

The following abbreviations were used in this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time, $[M+H]^+$ =molecular mass of the molecular cation, $[M-H]^-$=molecular mass of the molecular anion.

The following LC-MS methods were used to characterize the compounds:

Method A

| MS | ZQ Mass Spectrometer from Waters (single quadrupole mass spectrometer), ionization method: electrospray, polarity: positive ionization, capillary (kV) 3.00, cone (V) 30.00, source temperature (° C.) 100, desolvation temperature (° C.) 250, cone gas flow (L/Hr) 50, desolvation gas flow (L/Hr) 400, mass range: 150 to 1000 Da. |
|----|-----|
| LC | HP 1100 HPLC from Agilent: solvent degasser, quaternary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |

Method B

| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
|----|-----|
| LC | Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, |

-continued

| | DAD wavelength range (nm): 200 to 500, solvent gradient: A = 0.1% v/v formic acid in water and B = 0.1% v/v formic acid in acetonitrile. | | | |
|---|---|---|---|---|
| Time (min) | A % | B % | Flow (ml/min) | |
| 0.0 | 80 | 20 | 1.7 | |
| 5.0 | 0.0 | 100 | 1.7 | |
| 5.6 | 0.0 | 100 | 1.7 | |
| 6.0 | 80 | 20 | 1.7 | |

Method C

| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
|---|---|
| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method D

| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
|---|---|
| LC | Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method E

| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
|---|---|
| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): |

| | 200 to 500, solvent gradient: A = 0.1% v/v formic acid in water and B = 0.1% v/v formic acid in acetonitrile. | | | |
|---|---|---|---|---|
| Time (min) | A % | B % | Flow (ml/min) | |
| 0.0 | 80 | 20 | 1.7 | |
| 2.5 | 0.0 | 100 | 1.7 | |
| 2.8 | 0.0 | 100 | 1.7 | |
| 2.9 | 80 | 20 | 1.7 | |

Method F

| MS | ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da. |
|---|---|
| LC | HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Example 1.1

Method A for Preparing the Compounds of the Invention from a Carboxylic Acid

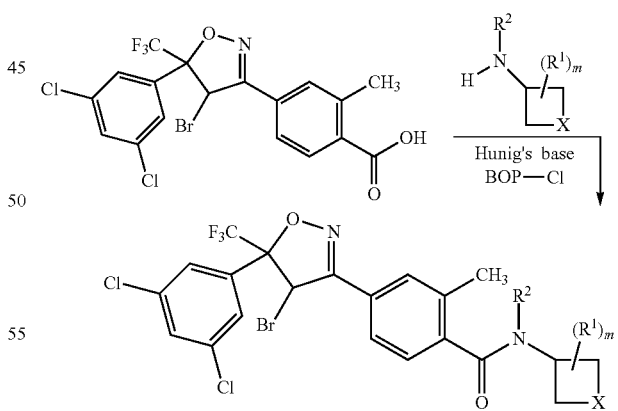

To a solution of the appropriate carboxylic acid (30 μmol), for example, 4-[4-bromo-5-(3,5-dichloro-phenyl)-5-trifluoromethyl-4,5-dihydro-isoxazol-3-yl]-2-methyl-benzoic acid (Example 1.7) for Compound No. A5 of Table A, in dimethylacetamide (0.4 ml) was added a solution of the appropriate amine (30 μmol), for example, 3-methyl-thietan-3-ylamine (preparation described in, for example, WO 2007/080131) for Compound No. A5 of Table A, in dimethylacetamide (0.145 ml) followed by diisopropylethylamine (Hunig's Base) (0.02 ml, 100 μmol) and a solution of bis(2-oxo-3-oxazolidinyl)phosphonic chloride ("BOP-Cl") (15.3 mg) in dimethylacetamide (0.2 ml). The reaction mixture was stirred at 80° C. for 16 hours. Then the mixture was diluted with acetonitrile (0.6 ml) and a sample was used for the LC-MS analysis. The remaining mixture was further diluted with acetonitrile/dimethylformamide (4:1) (0.8 ml) and purified by HPLC to give the desired compound.

This method was used to make:

Compound Nos. A1, A2, A15 and A16 of Table A from 4-[5-(3,5-dichloro-phenyl)-5-methyl-4,5-dihydro-isoxazol-3-yl]-naphthalene-1-carboxylic acid (preparation described in, for example, WO 2007/079162), Compound Nos. A3 and A4 of Table A from 4-[2-(3,5-dichloro-phenyl)-2-trifluoromethyl-aziridin-1-yl]-2-methyl-benzoic acid (Example 2.2), Compound Nos. A5-A8 of Table A from 4-[4-bromo-5-(3,5-dichloro-phenyl)-5-trifluoromethyl-4,5-dihydro-isoxazol-3-yl]-2-methyl-benzoic acid (preparation described in, for example, WO 2009/005015), Compound Nos. A9-A11 of Table A from 4-[5-(3,5-dichloro-phenyl)-2-oxo-5-trifluoromethyl-oxazolidin-3-yl]-2-methyl-benzoic acid (preparation described in, for example, in WO 2007/123853), Compound Nos. A12-A14 of Table A from 4-[5-(3,5-dichloro-phenyl)-1-methyl-5-trifluoromethyl-4,5-dihydro-1H-pyrazol-3-yl]-2-methyl-benzoic acid (preparation described in, for example, JP 2008/133273), Compound Nos. A18-A21 of Table A from 4-[5-(3,5-dichloro-phenyl)-2-methyl-5-trifluoromethyl-isoxazolidin-3-yl]-2-methyl-benzoic acid (Example 4.5), Compound Nos. A22-A25 of Table A from 7-[5-(3,5-dichloro-phenyl)-5-trifluoromethyl-4,5-dihydro-isoxazol-3-yl]-benzo[1,2,5]thiadiazole-4-carboxylic acid (Example 5.8), Compound Nos. A26-A29 of Table A from 4-[5-(3,5-dichloro-phenyl)-5-trifluoromethyl-4,5-dihydro-isoxazol-3-yl]-2-methyl-benzooxazole-7-carboxylic acid (Example 6.11), Compound Nos. A32-A35 of Table A from 4-[4-chloro-5-(3,5-dichloro-phenyl)-5-trifluoromethyl-4,5-dihydro-isoxazol-3-yl]-2-methyl-benzoic acid (preparation of corresponding methyl ester described in, for example, WO 2009/005015), Compound Nos. A36-A38 of Table A from 5-[5-(3,5-dichloro-phenyl)-5-trifluoromethyl-4,5-dihydro-isoxazol-3-yl]-naphthalene-1-carboxylic acid (Example 9.6), Compound Nos. A42-A45 of Table A were made from 4-[4-bromo-5-(3,5-dichloro-phenyl)-5-trifluoromethyl-4,5-dihydro-isoxazol-3-yl]-naphthalene-1-carboxylic acid (preparation of similar compounds described in, for example, WO 2009/005015), Compound Nos. A46-A49 of Table A were made from 4-[4-(3,5-dichloro-phenyl)-4-trifluoromethyl-3,4-dihydro-2H-pyrrol-2-yl]-2-methyl-benzoic acid (Example 10.6), Compound Nos. A51-A54 of Table A were made from 4-[5-(3,5-dichloro-phenyl)-4-hydroxy-5-trifluoromethyl-4,5-dihydro-isoxazol-3-yl]-2-methyl-benzoic acid (Example 12.2), Compound Nos. A55-A58 of Table A were made from 4-{5-(3,5-dichloro-phenyl)-4-hydroxyimino-5-trifluoromethyl-4,5-dihydro-isoxazol-3-yl}-2-methyl-benzoic acid (Example 13.3), and Compound Nos. A59-A62 of Table A were made from 4-[5-(3,5-dichloro-phenyl)-4-fluoro-5-trifluoromethyl-4,5-dihydro-isoxazol-3-yl]-2-methyl-benzoic acid (Example 14.2).

Compound Nos. A63, A68, A69 and A70 of Table A were made from 5'-(3,5-Dichloro-phenyl)-5'-trifluoromethyl-4',5'-dihydro[3,3']biisoxazolyl-5-carboxylic acid (Example 15.5).

Compound Nos. A64-A67 of Table A were made from 5-[5-(3,5-dichloro-phenyl)-5-trifluoromethyl-4,5-dihydro-isoxazol-3-yl]-2-methyl-2H-pyrazole-3-carboxylic acid (Example 16.2)

Example 1.2

Method B for Preparing the Compounds of the Invention from a Carboxylic Acid

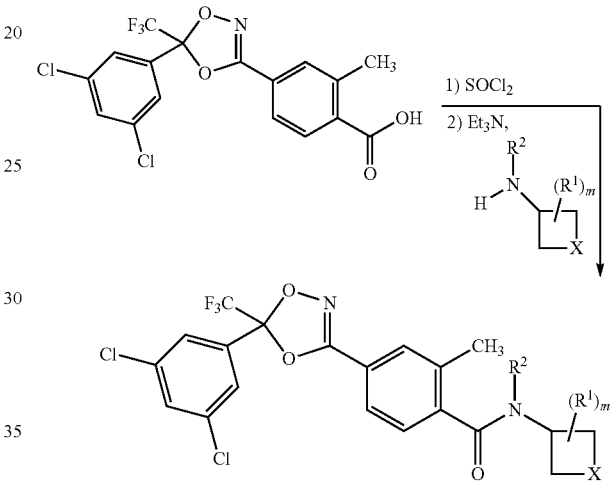

To a solution of the appropriate carboxylic acid, for example, 4-[5-(3,5-dichloro-phenyl)-5-trifluoromethyl-[1,4,2]dioxazol-3-yl]-2-methyl-benzoic acid (105 mg) (Example 3.2), in dichloromethane (3 ml) was added oxalyl chloride (0.025 ml). After addition of N,N-dimethylformamide ("DMF") (2 drops) the reaction mixture was stirred at ambient temperature for 2 hours. The reaction mixture was concentrated to give the acid chloride as a yellow solid, which was used without further purification. Triethylamine (0.175 ml) and the appropriate amine, for example, 3-methyl-thietan-3-ylamine (117 mg) (preparation as described in, for example, WO 2007/080131) were added to a solution of the acid chloride residue in dichloromethane (2 ml). The reaction mixture was stirred at ambient temperature for 16 hours. The reaction mixture was diluted with water and ethyl acetate and the phases were separated. The organic phase was washed successively with saturated aqueous hydrogen carbonate (1M) and brine, dried over sodium sulfate and concentrated. The residue was purified by column chromatography on silica gel (eluent: cylohexane/ethyl acetate) to afford Compound No. A17 of Table A (8 mg) as a colorless solid. M.p. 180-181° C.

This method was used to make:

Compound No. A17 of Table A from 4-[5-(3,5-dichloro-phenyl)-5-trifluoromethyl-[1,4,2]dioxazol-3-yl]-2-methyl-benzoic acid (Example 3.2), Compound No. A30 of Table A from 4-[5-(3,5-dichloro-phenyl)-4-ethylidene-5-trifluoromethyl-4,5-dihydro-isoxazol-3-yl]-2-methyl-benzoic acid (Example 7.2), Compound No. A31 of Table A from 8-bromo-4-[5-(3,5-dichloro-phenyl)-5-trifluoromethyl-4,5-dihydro-isoxazol-3-yl]-naphthalene-1-carboxylic acid (Example 8.2), Compound No. A39 of Table A from 4-[5-(3,5-dichloro-phenyl)-4-methyl-5-trifluoromethyl-4,5-dihydro-isoxazol-3-yl]-2-methyl-benzoic acid (preparation described in, for example, WO 2009/005015), Compound No. A40 of Table A from 4-[5-(3,5-dichloro-phenyl)-4-methylthio-5-trifluoromethyl-4,5-dihydro-isoxazol-3-yl]-2-methyl-benzoic acid (preparation described in, for example, WO 2009/005015), Compound No. A41 of Table A from 4-[5-(3,5-dichloro-phenyl)-4-methyl-sulfinyl-5-trifluoromethyl-4,5-dihydro-isoxazol-3-yl]-2-methyl-benzoic acid (which was obtained by oxidation of 4-[5-(3,5-dichloro-phenyl)-4-methylthio-5-trifluoromethyl-4,5-dihydro-isoxazol-3-yl]-2-methyl-benzoic acid with, for example, 3-chloroperoxybenzoic acid), and Compound No. A50 of Table A from 4-[5-(3,5-dichloro-phenyl)-5-trifluoromethyl-4,5-dihydro-isoxazol-3-yl]-2-methyl-naphthalene-1-carboxylic acid (Example 11.1).

Example 2.1

Preparation of 4-[2-(3,5-dichloro-phenyl)-2-trifluoromethyl-aziridin-1-yl]-2-methyl-benzoic acid methyl ester

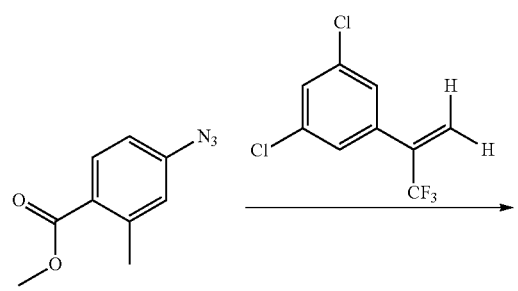

A mixture of 4-azido-2-methyl-benzoic acid methyl ester (made in analogy to methods described in, for example, Journal of Organic Chemistry, 2006, 71(15), 5822-5825) (820 mg, 3.4 mmol) and 1,3-dichloro-5-(1-trifluoromethyl-vinyl)-benzene (preparation described in, for example, EP 1,731,512) (500 mg, 2.6 mmol) in toluene (20 ml) was heated at 130° C. for 48 hours. The reaction mixture was concentrated and the residue purified by column chromatography on silica gel (eluent: 3% v/v ethyl acetate in hexane) to give 4-[4-(3,5-dichloro-phenyl)-4-trifluoromethyl-4,5-dihydro-[1,2,3]triazol-1-yl]-2-methyl-benzoic acid methyl ester as a gummy oil (200 mg).

Example 2.2

Preparation of 4-[2-(3,5-dichloro-phenyl)-2-trifluoromethyl-aziridin-1-yl]-2-methyl-benzoic acid

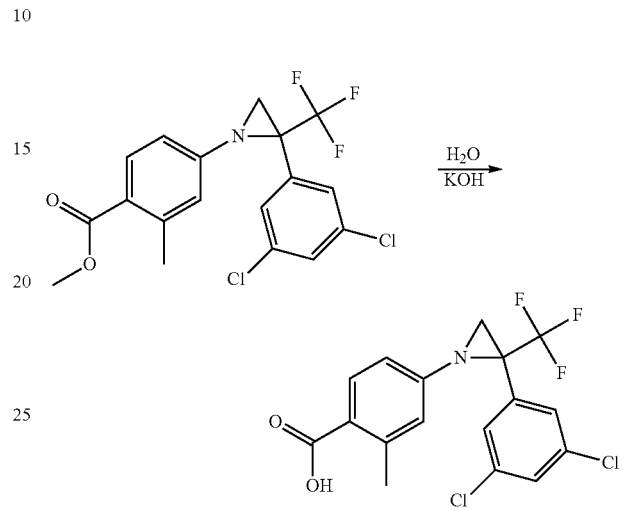

To a solution of 4-[4-(3,5-dichloro-phenyl)-4-trifluoromethyl-4,5-dihydro-[1,2,3]triazol-1-yl]-2-methyl-benzoic acid methyl ester (Example 2.1) (3.6 g, 8.33 mmol) in methanol (10 ml) was added aqueous potassium hydroxide (40% w/v) (35 ml) and the reaction mixture heated at 80° C. for 15 hours. The reaction mixture was then diluted with water and extracted with ethyl acetate. The aqueous phase was acidified by addition of aqueous hydrochloric acid (1M) and extracted again with ethyl acetate (3×200 ml). The combined organic extracts were washed with brine and concentrated. The residue was purified by column chromatography on silica gel (eluent: 15% v/v ethyl acetate in hexane) to give 4-[2-(3,5-dichloro-phenyl)-2-trifluoromethyl-aziridin-1-yl]-2-methyl-benzoic acid as a white solid (1.2 g). 1H-NMR (DMSO-d6, 400 MHz): 12.57 (s, 1H), 7.70 (d, 1H), 7.65 (s, 3H), 6.99 (s, 1H), 6.97 (d, 1H), 3.27 (s, 1H), 3.05 (s, 1H), 2.45 (s, 3H).

Example 3.1

Preparation of 5-(3,5-dichloro-phenyl)-3-(3,4-dimethyl-phenyl)-5-trifluoromethyl-[1,4,2]dioxazole

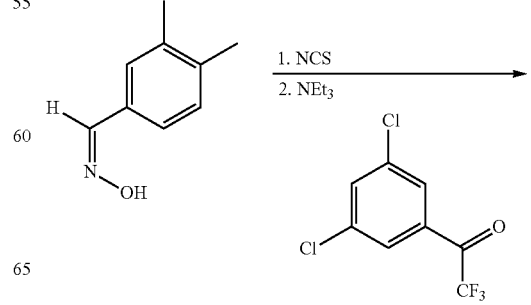

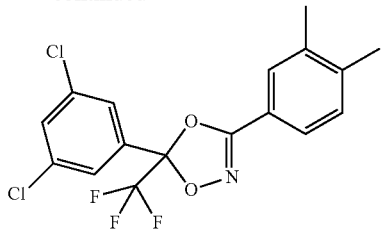

A solution of 3,4-dimethyl-benzaldehyde oxime (commercially available) (1.56 g) and N-chlorosuccinimide ("NCS") (1.4 g) in dimethylformamide (30 ml) was stirred at ambient temperature under an atmosphere of nitrogen for 3 hours. A solution of 3,5-dichloro-2,2,2-trifluoro-acetophenone (commercially available) (1 g) and triethylamine (1.46 ml) in dimethylformamide (12 ml) was then added dropwise and the reaction mixture was stirred at ambient temperature for 16 hours. The reaction mixture was diluted with water and extracted three times with diethyl ether. The combined organic extracts were washed with brine, dried over sodium sulfate and concentrated. The residue was purified by column chromatography on silica gel (eluent: cyclohexane/ethyl acetate) to give 5-(3,5-dichloro-phenyl)-3-(3,4-dimethyl-phenyl)-5-trifluoromethyl-[1,4,2]dioxazole (1.18 g).

Example 3.2

Preparation of 4-[5-(3,5-dichloro-phenyl)-5-trifluoromethyl-[1,4,2]dioxazol-3-yl]-2-methyl-benzoic acid

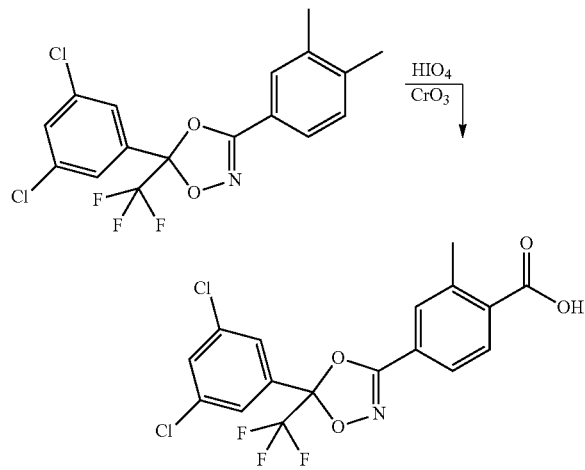

Periodic acid (2.2 g) was dissolved under an atmosphere of nitrogen in dimethylformamide (35 ml). After 15 minutes, chromium(VI) oxide (55 mg) was added followed by 5-(3,5-dichloro-phenyl)-3-(3,4-dimethyl-phenyl)-5-trifluoromethyl-[1,4,2]dioxazole (Example 3.1) (1 g) and the reaction mixture was stirred at ambient temperature for 16 hours. The solids were removed by filtration and the filtrate was concentrated. The residue was diluted with aqueous sodium carbonate (1M) (100 ml) and dichloromethane (100 ml) and the phases were separated. The aqueous layer was extracted twice with dichloromethane and then acidified to pH 1 by addition of aqueous hydrochloric acid (concentrated). The aqueous layer was extracted three times with dichloromethane. The combined organic extracts were dried over sodium sulfate and concentrated. The residue was purified by column chromatography on silica gel (eluent: cyclohexane/ethyl acetate, then methanol) to afford a mixture of isomers. The mixture of isomers were separated by reverse phase HPLC to give 4-[5-(3,5-dichloro-phenyl)-5-trifluoromethyl-[1,4,2]dioxazol-3-yl]-2-methyl-benzoic acid (792 mg) as a solid. M.p. 114-134° C. 1H-NMR (DMSO-d6, 400 MHz): 13.5 (bs, 1H), 7.8-8.0 (m, 6H), 2.6 (s, 3H).

Example 4.1

Preparation of 4-bromo-2-methyl-benzoic acid tert-butyl ester

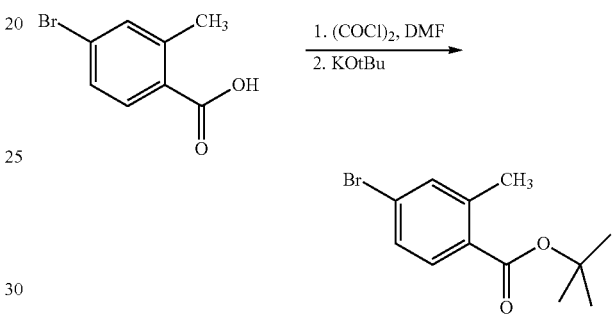

4-Bromo-2-methyl-benzoic acid (commercially available) (50 g) was suspended in dichloromethane (500 ml). A catalytic amount of dimethylformamide ("DMF") and oxalyl chloride (23 ml) were added to the suspension. The reaction mixture was stirred at ambient temperature for 3 hours. The reaction mixture was concentrated and the residue dissolved in dry tetrahydrofuran (800 ml). The solution was cooled to 2° C. and added to a solution of potassium tert-butoxide (39.2 g) in dry tetrahydrofuran (300 ml) dropwise at 5-10° C. The reaction mixture was stirred at ambient temperature for 30 minutes and then poured onto a mixture of ice and water. The mixture was extracted with ethyl acetate. The organic extract was washed with water, dried over sodium sulfate and concentrated to give 4-bromo-2-methyl-benzoic acid tert-butyl ester (65.3 g) as yellow oil. $^1$H-NMR (CDCl$_3$, 400 MHz): 7.70 (d, 1H), 7.40 (s, 1H), 7.35 (d, 1H), 2.58 (s, 3H), 1.60 (s, 9H).

Example 4.2

Preparation of 4-formyl-2-methyl-benzoic acid tert-butyl ester

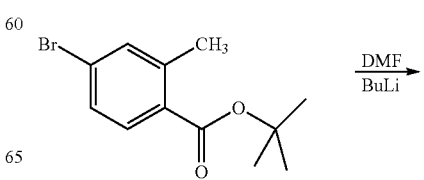

(CDCl₃, 400 MHz): 8.10 (s, 1H), 8.02 (d, 1H), 7.85 (d, 1H), 7.35 (s, 1H), 3.90 (s, 3H), 2.60 (s, 3H).

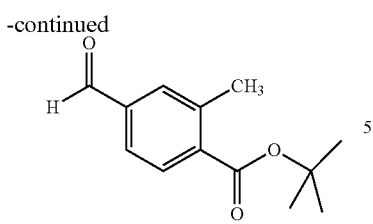

A solution of 4-bromo-2-methyl-benzoic acid tert-butyl ester (Example 4.1) (75 g) in dry tetrahydrofuran (750 ml) was cooled to −100° C. A solution of butyl lithium (1.6M in hexane) (163 ml) was added dropwise at −100° C. Dimethylformamide ("DMF") (1.14 ml) was added at −100° C. The reaction mixture was stirred at −95° C. for 75 minutes. The reaction was quenched by addition of aqueous ammonium chloride (saturated) (8 ml) at −90° C. The mixture was stirred for 10 minutes at −90° C., warmed to 0° C. and poured onto a mixture of ice and water. The mixture was allowed to warm to ambient temperature and then extracted twice with ethyl acetate. The combined organic phases were washed with water, dried over sodium sulfate, and concentrated to give 4-formyl-2-methyl-benzoic acid tert-butyl ester (60.3 g) as yellow oil. ¹H-NMR (CDCl₃, 400 MHz): 10.03 (s, 1H), 7.93 (d, 1H), 7.75 (m, 2H), 2.65 (s, 3H), 1.65 (s, 9H).

Example 4.3

Preparation of (4-tert-butoxycarbonyl-3-methyl-benzylidene)-N-methyl-nitrone

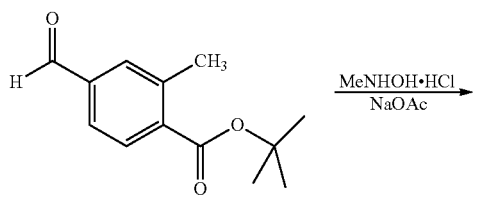

To a solution of 4-formyl-2-methyl-benzoic acid tert-butyl ester (Example 4.2) (1.57 g) in tetrahydrofuran/water (3:1) (20 ml) was added sodium acetate (0.67 g) and N-methyl-hydroxylamine hydrochloride (0.69 g). The reaction mixture was stirred at 50° C. for 15 hours. The reaction mixture was diluted with ethyl acetate and water. The phases were separated and the organic layer was washed with water, dried over sodium sulfate and concentrated. The residue was purified by column chromatography on silica gel (eluent: methanol/ethyl acetate 5:5) to give (4-tert-butoxycarbonyl-3-methyl-benzylidene)-N-methyl-nitrone (1.43 g) as yellow oil. ¹H-NMR

Example 4.4

Preparation of 4-[5-(3,5-dichloro-phenyl)-2-methyl-5-trifluoromethyl-isoxazolidin-3-yl]-2-methyl-benzoic acid tert-butyl ester

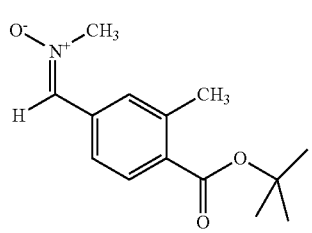

To a solution of (4-tert-butoxycarbonyl-3-methyl-benzylidene)-N-methyl-nitrone (Example 4.3) (1.42 g) in toluene (10 ml) was added 1,3-dichloro-5-(1-trifluoromethyl-vinyl)-benzene (preparation described in, for example, EP 1,731,512) (2.17 g). The reaction mixture was heated in a microwave at 120° C. for 3.5 hours. The toluene was evaporated and the residue was purified by column chromatography on silica gel (eluent: ethyl acetate/heptane 5:95 to 50:50) to give 4-[5-(3,5-dichloro-phenyl)-2-methyl-5-trifluoromethyl-isoxazolidin-3-yl]-2-methyl-benzoic acid tert-butyl ester as a mixture of diastereoisomers (1.73 g). ¹H-NMR (CDCl₃, 400 MHz): 7.80-7.10 (m, 6H), 3.85-3.55 (m, 1H), 3.32-2.50 (m, 9H), 1.60 (m, 9H).

Example 4.5

Preparation 4-[5-(3,5-dichloro-phenyl)-2-methyl-5-trifluoromethyl-isoxazolidin-3-yl]-2-methyl-benzoic acid

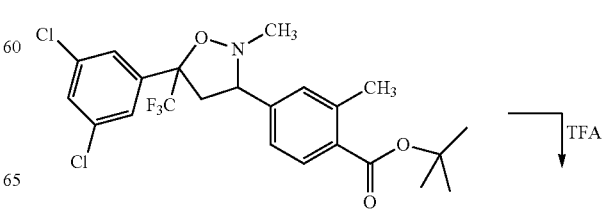

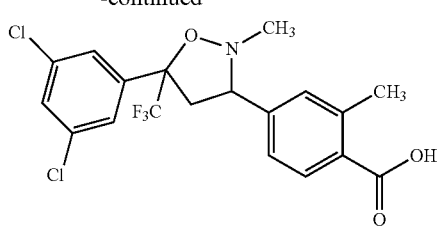

To a solution of 4-[5-(3,5-dichloro-phenyl)-2-methyl-5-trifluoromethyl-isoxazolidin-3-yl]-2-methyl-benzoic acid tert-butyl ester (Example 4.4) (0.67 g) in dichloromethane (15 ml) was added trifluoroacetic acid ("TFA") (1.05 ml). The reaction mixture was stirred at ambient temperature for 16 hours. The dichloromethane was evaporated and ethyl acetate was added. The mixture was washed with water, dried over sodium sulfate and concentrated. The residue was purified by preparative HPLC to give 4-[5-(3,5-dichloro-phenyl)-2-methyl-5-trifluoromethyl-isoxazolidin-3-yl]-2-methyl-benzoic acid as a mixture of diastereoisomers (0.56 g). $^1$H-NMR (CDCl$_3$, 400 MHz): 8.05 (m, 1H), 7.45-7.15 (m, 5H), 3.90-3.60 (m, 1H), 3.35-2.60 (m, 9H).

Example 5.1

Preparation of 4-bromo-7-bromomethyl-benzo[1,2,5]thiadiazole

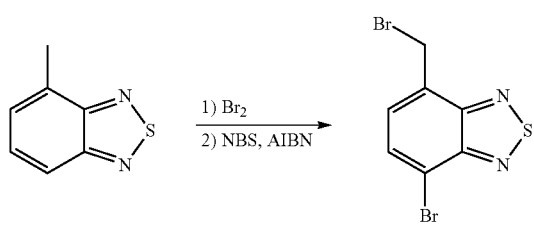

Bromine (9.78 ml) was added to a solution of 4-methyl-benzo[c][1,2,5]thiadiazole (commercially available) (15 g) in aqueous hydrobromic acid (48% w/v) (100 ml). The reaction mixture was heated at reflux temperature for 2 hours. The reaction mixture was allowed to cool to ambient temperature and diluted with aqueous sodium metabisulfite (20 g in 250 ml water). The mixture was extracted twice with dichloromethane. The combined organic phases were washed with water and brine, dried over sodium sulfate, and concentrated to give a mixture of brominated products. This mixture was suspended in α,α,α-trifluorotoluene (250 ml) and N-bromosuccinimide ("NBS") (13.88 g) and 2,2'-azobis(2-methylpropionitrile) ("AIBN") (0.640 g) were added. The reaction mixture was heated at 90° C. for 3 hours. The reaction mixture was allowed to cool to ambient temperature and was diluted with dichloromethane (600 ml) and aqueous hydrochloric acid (1M) (300 ml). The phases were separated and the organic layer was washed successively with aqueous hydrochloric acid (1M) (2×250 ml), water (200 ml) and brine (200 ml), dried over sodium sulfate and concentrated to give 4-bromo-7-bromomethyl-benzo[1,2,5]thiadiazole (29.05 g) as a yellow solid. $^1$H-NMR (400 MHz, CDCl$_3$): 7.82 (d, 1H), 7.54 (d, 1H), 4.94 (s, 2H) ppm.

Example 5.2

Preparation of (7-bromo-benzo[1,2,5]thiadiazol-4-yl)-methanol

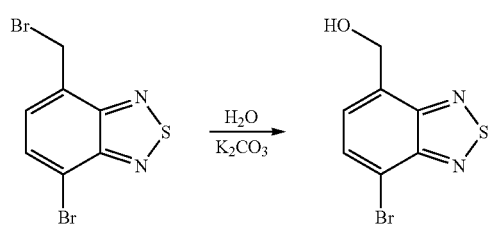

A mixture of 4-bromo-7-bromomethyl-benzo[1,2,5]thiadiazole (Example 5.1) (29.05 g), potassium carbonate (65.2 g) and water (400 ml) was stirred at 110° C. for 16 hours. The reaction mixture was cooled to ambient temperature and quenched by addition of aqueous hydrochloric acid (2M) (400 ml). Ethyl acetate (600 ml) was added to the mixture. The phases were separated and the organic layer was washed successively with aqueous hydrochloric acid (2M) (400 ml), water (250 ml) and brine (250 ml), dried over sodium sulfate and concentrated to give (7-bromo-benzo[1,2,5]thiadiazol-4-yl)-methanol (20.22 g) as a orange solid. $^1$H-NMR (400 MHz, CDCl$_3$): 7.87 (d, 1H), 7.57 (d, 1H), 5.14 (s, 2H) ppm.

Example 5.3

Preparation of 7-bromo-benzo[1,2,5]thiadiazole-4-carbaldehyde

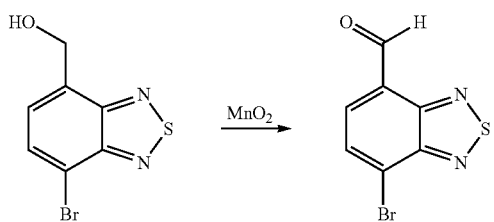

To a solution of (7-bromo-benzo[1,2,5]thiadiazol-4-yl)-methanol (Example 5.2) (20.22 g) in dichloromethane (185 ml) was added manganese(IV) oxide (71.7 g). The suspension was stirred at ambient temperature for 16 hours. The reaction mixture was filtered through a plug of Celite®. The filtrate was concentrated to give 7-bromo-benzo[1,2,5]thiadiazole- 4-carbaldehyde (16.65 g) as an orange solid. $^1$H-NMR (400 MHz, CDCl$_3$): 10.74 (s, 1H), 8.11-8.05 (m, 2H) ppm.

Example 5.4

Preparation of 7-bromo-benzo[1,2,5]thiadiazole-4-carbaldehyde oxime

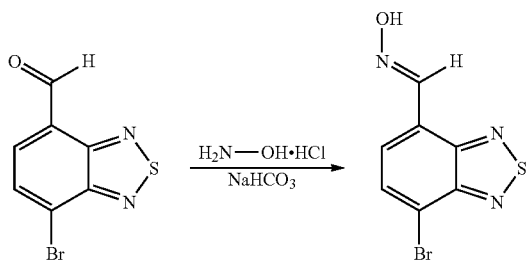

To a solution of 7-bromo-benzo[1,2,5]thiadiazole-4-carbaldehyde (Example 5.3) (16.65 g) in ethanol (150 ml) were added hydroxylamine hydrochloride (9.52 g), sodium hydrogen carbonate (11.51 g) and water (15 ml). The reaction mixture was stirred at ambient temperature for 16 hours. The reaction mixture was diluted with ethyl acetate (1500 ml) and water (400 ml). After separation of the phases, the aqueous layer was extracted with ethyl acetate (200 ml). The combined organic layers were washed with water (200 ml) and brine (200 ml), dried over sodium sulfate and concentrated to give 7-bromo-benzo[1,2,5]thiadiazole-4-carbaldehyde oxime (16.65 g) as a brown solid. $^1$H-NMR (DMSO-d6, 400 MHz): 11.94 (s, 1H), 8.66 (s, 1H), 8.09-9.90 (m, 2H) ppm.

Example 5.5

Preparation of 7-bromo-N-hydroxy-benzo[1,2,5]thiadiazole-4-carbimidoyl chloride

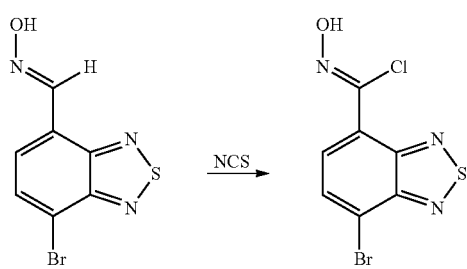 [SMILES: O/N=C/c1ccc(Br)c2nsnc12 ; "NCS" ; O/N=C(\Cl)c1ccc(Br)c2nsnc12]

To a solution of 7-bromo-benzo[1,2,5]thiadiazole-4-carbaldehyde oxime (Example 5.4) (16.65 g) in dimethylformamide (150 ml) was added N-chlorosuccinimide ("NCS") (10.34 g). The reaction mixture stirred at ambient temperature for 16 hours. Water (750 ml) was added to the reaction mixture and the solids were isolated by filtration to obtain 7-bromo-N-hydroxy-benzo[1,2,5]thiadiazole-4-carbimidoyl chloride (15.77 g) as a yellow solid which was used without further purification.

Example 5.6

Preparation of 4-bromo-7-[5-(3,5-dichloro-phenyl)-5-trifluoromethyl-4,5-dihydro-isoxazol-3-yl]-benzo[1,2,5]thiadiazole

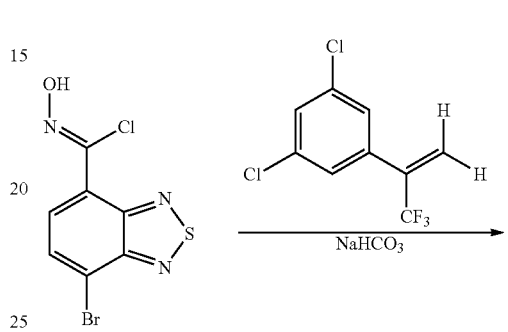

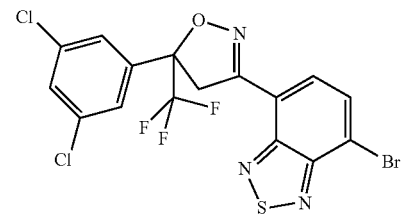

To a solution of 7-bromo-N-hydroxy-benzo[1,2,5]thiadiazole-4-carbimidoyl chloride (Example 5.5) (10.01 g) in 2-propanol (140 ml) was added 1,3-dichloro-5-(1-trifluoromethyl-vinyl)-benzene (preparation described in, for example, EP 1,731,512) (6.87 g) and sodium hydrogen carbonate (5.99 g). The reaction mixture was stirred at 65° C. for 3 hours. The reaction mixture was concentrated and the residue was purified by column chromatography (heptane/ethyl acetate 9:1) to give 4-bromo-7-[5-(3,5-dichloro-phenyl)-5-trifluoromethyl-4,5-dihydro-isoxazol-3-yl]-benzo[1,2,5]thiadiazole (7.4 g). $^1$H-NMR (DMSO-d6, 400 MHz): 8.17-7.53 (m, 5H), 4.70 (d, 1H), 4.49 (d, 1H) ppm.

Example 5.7

Preparation of 7-[5-(3,5-dichloro-phenyl)-5-trifluoromethyl-4,5-dihydro-isoxazol-3-yl]-benzo[1,2,5]thiadiazole-4-carboxylic acid methyl ester

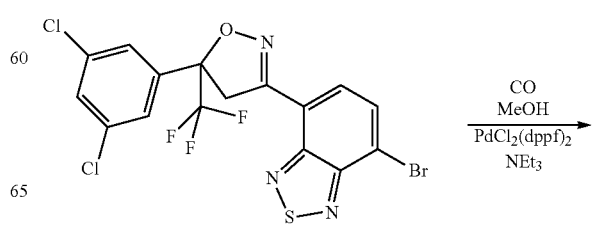

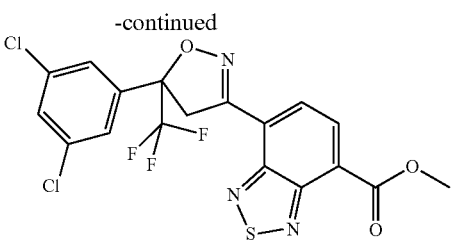

Triethylamine (7.8 ml) and methanol (72 ml) were added at ambient temperature to a solution of 4-bromo-7-[5-(3,5-dichloro-phenyl)-5-trifluoromethyl-4,5-dihydro-isoxazol-3-yl]-benzo[1,2,5]thiadiazole (Example 5.6) (7.96 g) in dimethylformamide (72 ml). [1,1'-Bis(diphenylphosphino)ferrocene]dichloropalladium(II) ("PdCl$_2$(dppf)") (654 mg) was added and the reaction mixture was stirred in a pressure reactor in an atmosphere of carbon monoxide (3 bar) at 87° C. for 16 hours. The reaction mixture was cooled to ambient temperature, filtered through a plug of Celite® and concentrated. The residue was purified by column chromatography on silica gel (eluent: heptane/ethyl acetate) to give 7-[5-(3,5-dichloro-phenyl)-5-trifluoromethyl-4,5-dihydro-isoxazol-3-yl]-benzo[1,2,5]thiadiazole-4-carboxylic acid methyl ester (4.01 g) as an orange oil. $^1$H-NMR (CDCl$_3$, 400 MHz): 8.43-7.57 (m, 5H), 4.66 (d, 1H), 4.27 (d, 1H), 4.09 (s, 3H) ppm.

Example 5.8

Preparation of 7-[5-(3,5-dichloro-phenyl)-5-trifluoromethyl-4,5-dihydro-isoxazol-3-yl]-benzo[1,2,5]thiadiazole-4-carboxylic acid

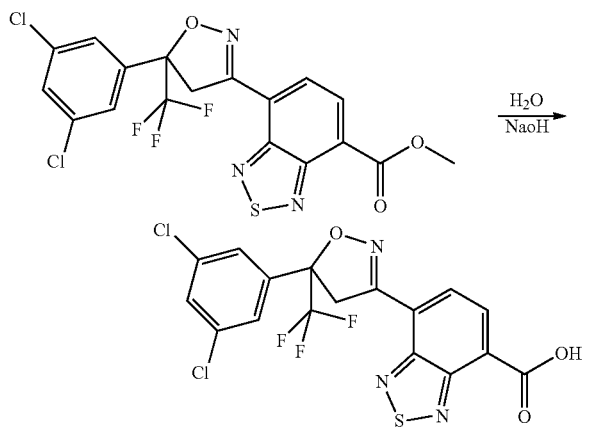

To a solution of 7-[5-(3,5-dichlorophenyl)-5-trifluoromethyl-4,5-dihydro-isoxazol-3-yl]-benzo[1,2,5]thiadiazole-4-carboxylic acid methyl ester (Example 5.7) (4.01 g) in tetrahydrofuran (30 ml) was added aqueous sodium hydroxide (1M) (25.3 ml). The reaction mixture was stirred at ambient temperature for 1.5 hours. Aqueous hydrochloric acid (1M) (100 ml) was added and the mixture diluted with ethyl acetate (150 ml). After separation of the layers, the aqueous layer was extracted with ethyl acetate (2×75 ml). The combined organic layers were washed with water (75 ml) and brine (75 ml), dried over sodium sulfate and concentrated. The residue was purified by column chromatography (dichloromethane/methanol) to give 7-[5-(3,5-dichloro-phenyl)-5-trifluoromethyl-4,5-dihydro-isoxazol-3-yl]-benzo[1,2,5]thiadiazole-4-carboxylic acid (1.29 g) as yellow solid. $^1$H-NMR (DMSO-d6, 400 MHz): 13.67 (bs, 1H), 8.37-7.26 (m, 5H), 4.76 (d, 1H), 4.53 (d, 1H) ppm.

Example 6.1

Preparation of 3-hydroxy-2-nitro-benzoic acid methyl ester

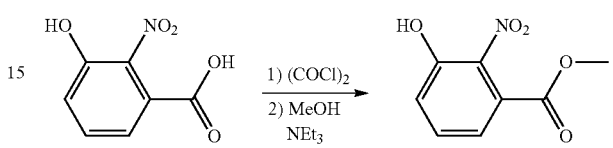

3-Hydroxy-2-nitro-benzoic acid (commercially available) (31.5 g) was suspended in acetonitrile (100 ml). Oxalyl chloride (22 ml) in acetonitrile (20 ml) was added dropwise upon which a vigorous gas stream evolved. After 15 minutes the reaction slowed down and therefore, the reaction mixture was heated with a warm water bath (40° C.) for 40 minutes. The mixture was concentrated and the residue was re-dissolved in dichloromethane (100 ml). A mixture of methanol (50 ml) and triethylamine (20 ml) in dichloromethane (30 ml) was added dropwise while cooling the mixture with an ice bath. The reaction mixture was stirred at ambient temperature for 16 hours. The mixture was concentrated and the residue was purified by column chromatography on silica gel (eluent: 10-55% v/v ethyl acetate in heptane) to give 3-hydroxy-2-nitro-benzoic acid methyl ester (15.9 g). 1H-NMR (400 MHz, CDCl$_3$): 10.15 (bs, 1H), 7.60 (t, 1H), 7.27 (d, 1H), 7.08 (d, 1H), 3.93 (s, 3H) ppm.

Example 6.2

Preparation of 4-bromo-3-hydroxy-2-nitro-benzoic acid methyl ester

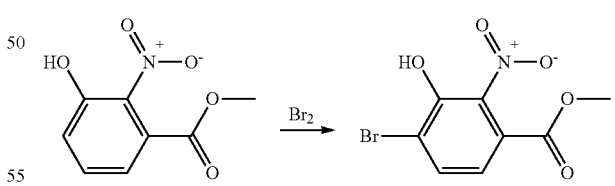

To a solution of 3-hydroxy-2-nitrobenzoic acid methyl ester (Example 6.1) (11 g) in chloroform (220 ml) was added dropwise bromine (18.7 g). The reaction mixture was heated at reflux for 16 hours. The reaction mixture was allowed to cool to ambient temperature and the reaction quenched by addition of aqueous sodium metabisulfite (22 g in 100 ml water) and the mixture was stirred for 15 minutes. The phases were separated and the organic phase was washed with brine, dried over sodium sulfate and concentrated. The residue was crystallized from diethyl ether/heptane to give 4-bromo-3- hydroxy-2-nitro-benzoic acid methyl ester (6.6 g). 1H-NMR (400 MHz, CDCl$_3$): 9.92 (s, 1H), 7.84 (d, 1H), 7.09 (d, 1H), 3.93 (s, 3H) ppm.

Example 6.3

Preparation of 2-amino-4-bromo-3-hydroxy-benzoic acid methyl ester

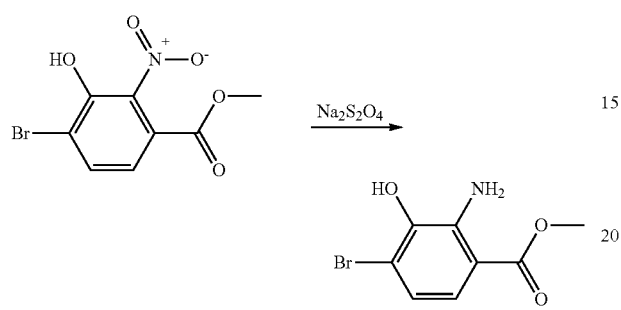

To a solution of 4-bromo-3-hydroxy-2-nitro-benzoic acid methyl ester (Example 6.2) (3.13 g) in tetrahydrofuran (40 ml) was added a solution of sodium dithionite (10.23 g) in water (40 ml). The reaction mixture was stirred at 60° C. for 2 hours. Then the reaction was diluted with ethyl acetate (80 ml) and aqueous hydrochloric acid (1M) (30 ml) and the mixture vigorously shaken. The phases were separated and the aqueous phase was extracted with ethyl acetate (60 ml). The combined organic extracts were washed with brine, dried over sodium sulfate and concentrated to give 2-amino-4-bromo-3-hydroxy-benzoic acid methyl ester (2.46 g). 1H-NMR (400 MHz, CDCl$_3$): 7.35 (d, 1H), 6.72 (d, 1H), 6.05 (s, 1H), 5.47 (s, 1H), 3.87 (s, 3H) ppm.

Example 6.4

Preparation of 7-bromo-2-methyl-benzo[d]oxazole-4-carboxylic acid methyl ester

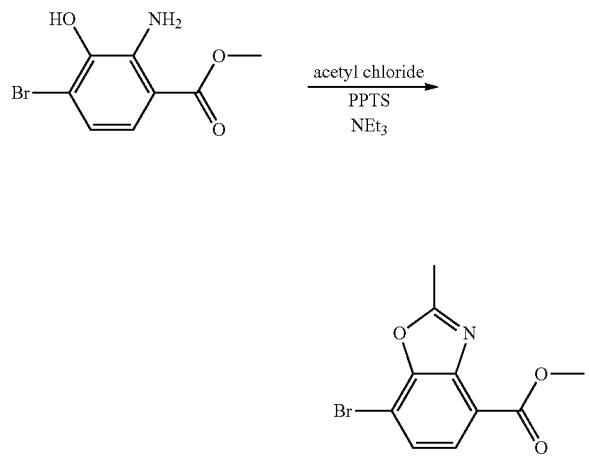

To a solution of 2-amino-4-bromo-3-hydroxy-benzoic acid methyl ester (Example 6.3) (2.46 g) in toluene (250 ml) was added sequentially triethylamine (1.53 ml), pyridinium p-toluenesulfonate ("PPTS") (0.75 g) and acetyl chloride (0.78 ml). The reaction mixture was heated at reflux for 16 hours. The reaction mixture was cooled to ambient temperature and diluted with aqueous hydrochloric acid (1M) (100 ml) and ethyl acetate (200 ml). The phases were separated and the organic extract was washed with aqueous hydrochloric acid (1M) (150 ml) and brine (150 ml) and then dried over sodium sulfate. The solids were removed by filtration and the filtrate was concentrated to give 7-bromo-2 methyl-benzo[d] oxazole-4-carboxylic acid methyl ester (2.94 g). 1H-NMR (400 MHz, CDCl$_3$): 7.87 (d, 1H), 7.52 (d, 1H), 4.04 (s, 3H), 2.77 (s, 3H) ppm.

Example 6.5

Preparation of (7-bromo-2-methyl-benzo[d]oxazol-4-yl)-methanol

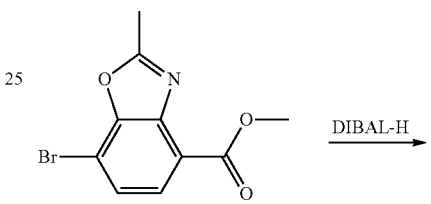

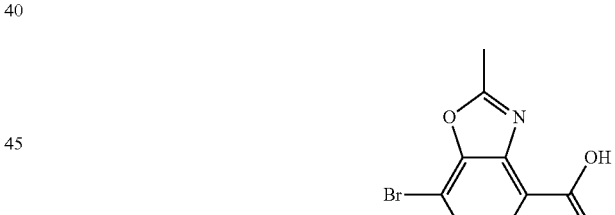

To a solution of 7-bromo-2 methyl-benzo[d]oxazole-4-carboxylic acid methyl ester (Example 6.4) (8.64 g) in tetrahydrofuran (250 ml) was added dropwise a solution of diisobutylaluminium hydride ("DIBAL-H") (1M in hexane) (80 ml) under a nitrogen atmosphere at 0° C. The reaction mixture was stirred at 0° C. for 20 minutes. Then the ice-bath was removed and the reaction mixture was allowed to warm to ambient temperature. After 40 minutes the mixture was cooled with an ice-bath and the reaction was quenched by the slow addition of water (5.0 ml). The mixture was poured onto aqueous sodium hydrogen carbonate (saturated) (300 ml) and extracted with diethyl ether (400 ml). The aqueous phase was further extracted with diethyl ether (2×300 ml). The combined organic extracts were washed with brine, dried over sodium sulfate and concentrated. The residue was triturated in a mixture of diisopropyl ether and heptane (3:1) to give (7-bromo-2-methyl-benzo[d]oxazol-4-yl)-methanol (4.45 g). 1H-NMR (400 MHz, CDCl₃): 7.41 (d, 1H), 7.17 (d, 1H), 4.98 (s, 3H), 3.06 (s, 1H), 2.67 (s, 3H) ppm.

Example 6.6

Preparation of 7-bromo-2-methyl-benzo[d]oxazole-4-carbaldehyde

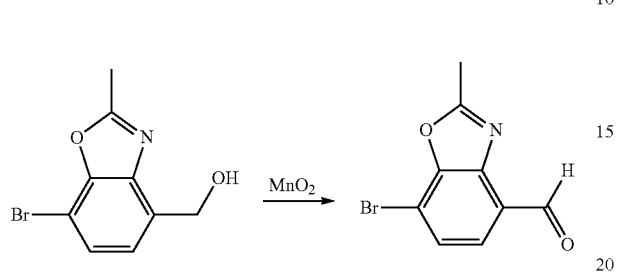

To a solution of (7-bromo-2-methyl-benzo[d]oxazol-4-yl) methanol (Example 6.5) (5.16 g) in dichloromethane (300 ml) was added manganese(IV) oxide (59.9 g) and the suspension stirred at ambient temperature for 16 hours. The reaction mixture was filtered through a plug of silica gel and the filtrate concentrated to give 7-bromo-2-methyl-benzo[d]oxazole-4-carbaldehyde (3.23 g). LC-MS: RT=1.83 min, [M+H]⁺ =240.0/242.0, method A.

Example 6.7

Preparation of (E)-7-bromo-2-methyl-benzo[d]oxazole-4-carbaldehyde oxime

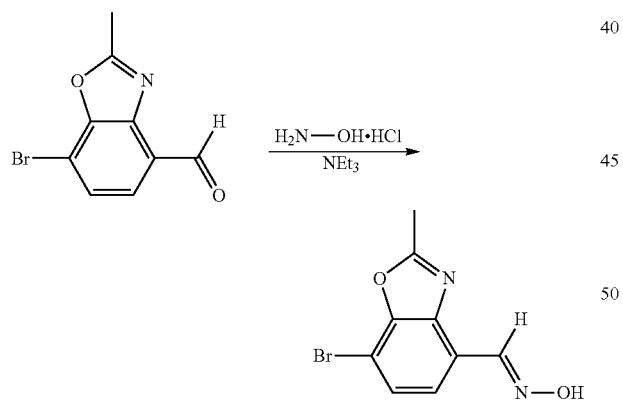

To a suspension of 7-bromo-2-methyl-benzo[d]oxazole-4-carbaldehyde (Example 6.6) (3.23 g) in a mixture of methanol and water (7:3) (60 ml) were added successively hydroxylamine hydrochloride (1.03 g) and triethylamine (2.06 ml) and the reaction mixture was stirred at ambient temperature for 1 hour. The reaction mixture was diluted with ethyl acetate (200 ml) and water (200 ml). The phases were separated and the aqueous phase was extracted with ethyl acetate (150 ml). The combined organic extracts were washed with brine (200 ml), dried over sodium sulfate and concentrated to give (E)-7-bromo-2-methyl-benzo[d]oxazole-4-carbaldehyde oxime (3.61 g) as a brown solid. 1H-NMR (400 MHz, CDCl₃): 9.47 (s, 1H) 7.47 (d, 1H), 7.33 (d, 1H), 2.74 (s, 3H) ppm.

Example 6.8

Preparation of (Z)-7-bromo-N-hydroxy-2-methyl-benzo[d]oxazole-4-carbimidoyl chloride

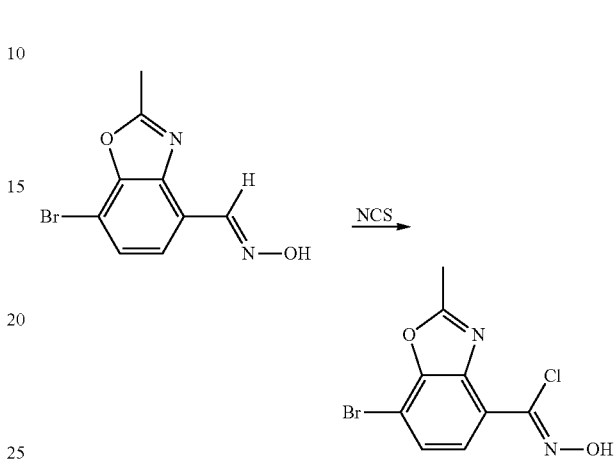

To a solution of (E)-7-bromo-2-methyl-benzo[d]oxazole-4-carbaldehyde oxime (Example 6.7) (3.61 g) in dimethylformamide (30 ml) was added N-bromosuccinimide ("NCS") (7.54 g) and the reaction mixture stirred at ambient temperature for two hours. Water (300 ml) was added to the mixture and the solids were isolated by filtration to give (Z)-7-bromo-N-hydroxy-2-methyl-benzo[d]oxazole-4-carbimidoyl chloride (3.63 g) as an orange solid. 1H-NMR (DMSO-d6, 400 MHz): 12.76 (s, 1H) 7.69 (d, 1H), 7.58 (d, 1H), 2.68 (s, 3H) ppm.

Example 6.9

Preparation of 7-bromo-4-(5-(3,5-dichlorophenyl)-5-trifluoromethyl-4,5-dihydro-isoxazol-3-yl)-2-methyl-benzo[d]oxazole

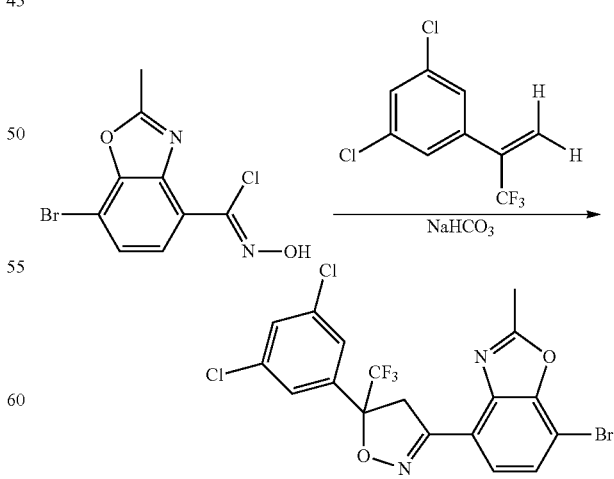

To a solution of 7-bromo-N-hydroxy-2-methyl-benzo[d] oxazole-4-carbimidoyl chloride (Example 6.8) (3.63 g) in 2-propanol (100 ml) was added 1,3-dichloro-5-(1-trifluoromethyl-vinyl)-benzene (preparation described in, for example, EP 1,731,512) (3.43 g) and sodium hydrogen carbonate (1.44 g). The reaction mixture was stirred at 65° C. for 16 hours. The reaction mixture was concentrated and the residue was purified by column chromatography on silica gel (eluent: 2-25% v/v ethyl acetate in heptane) to give 7-bromo-4-(5-(3,5-dichlorophenyl)-5-trifluoromethyl-4,5-dihydro-isoxazol-3-yl)-2-methyl-benzo[d]oxazole (3.7 g). 1H-NMR (400 MHz, CDCl$_3$): 7.71-7.42 (m, 5H), 4.50 (d, 1H), 4.06 (d, 1H), 2.73 (s, 3H) ppm.

Example 6.10

Preparation of 4-(5-(3,5-dichlorophenyl)-5-trifluoromethyl-4,5-dihydro-isoxazol-3-yl)-2-methyl-benzo[d]oxazole-7-carboxylic acid methyl ester

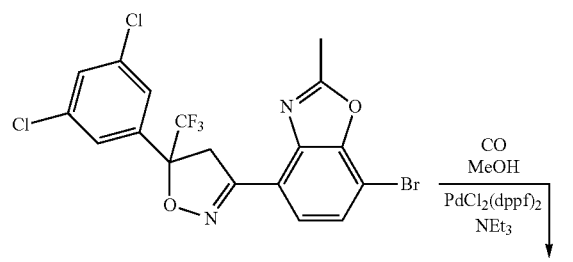

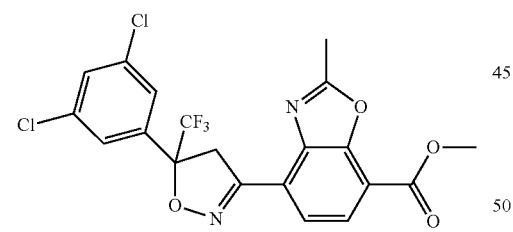

To a solution of 7-bromo-4-(5-(3,5-dichlorophenyl)-5-trifluoromethyl-4,5-dihydro-isoxazol-3-yl)-2-methyl-benzo[d]oxazole (Example 6.9) (3.5 g) in dimethyl-formamide (40 ml) was added successively triethylamine (2.5 ml), methanol (60 ml) and [1,1'-bis(diphenylphosphino)ferrocene]dichloropalladium(II) ("PdCl2(dppf)") (259 mg). The reaction mixture was stirred in a pressure reactor in an atmosphere of carbon monoxide (4 bar) at 80° C. for 16 hours. The reaction mixture was cooled to ambient temperature, filtered over a plug of Celite® and concentrated. The residue was purified by column chromatography on silica gel (eluent: 15-55% v/v ethyl acetate in heptane) to give 4-(5-(3,5-dichlorophenyl)-5-trifluoromethyl-4,5-dihydro-isoxazol-3-yl)-2-methyl-benzo[d]oxazole-7-carboxylic acid methyl ester (2.75 g). 1H-NMR (400 MHz, CDCl$_3$): 7.95-7.42 (m, 5H), 4.56 (d, 1H), 4.12 (d, 1H), 4.02 (s, 3H), 2.77 (s, 3H) ppm.

Example 6.11

Preparation of 4-(5-(3,5-dichlorophenyl)-5-trifluoromethyl-4,5-dihydro-isoxazol-3-yl)-2-methyl-benzo[d]oxazole-7-carboxylic acid

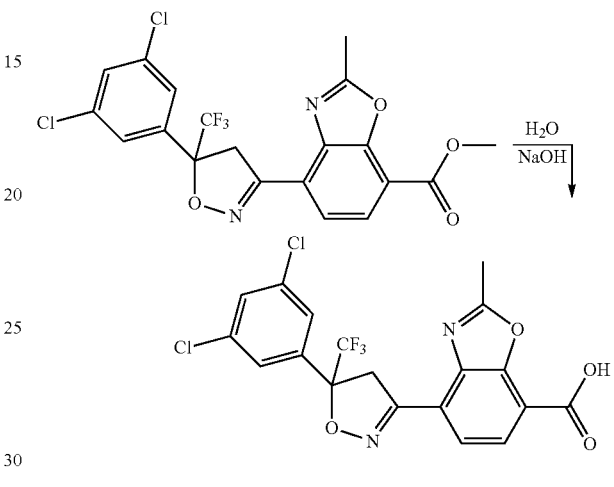

To a solution of 4-(5-(3,5-dichlorophenyl)-5-trifluoromethyl-4,5-dihydro-isoxazol-3-yl)-2-methyl-benzo[d]oxazole-7-carboxylic acid methyl ester (Example 6.10) (2.75 g) in tetrahydrofuran (50 ml) was added aqueous sodium hydroxide (1M) (8.7 ml) and methanol (5 ml). The reaction mixture was stirred at ambient temperature for 2.5 hours. The reaction mixture was diluted with aqueous hydrochloric acid (1M) (150 ml) and ethyl acetate (200 ml) and the phases separated. The organic phase was washed with brine, dried over sodium sulfate and concentrated. The residue was purified by column chromatography on silica gel (eluent: 1-6% v/v methanol in dichloromethane) to give 4-(5-(3,5-dichlorophenyl)-5-trifluoromethyl-4,5-dihydro-isoxazol-3-yl)-2-methyl-benzo[d]oxazole-7-carboxylic acid (2.12 g) as yellow solid. 1H-NMR (400 MHz, CDCl$_3$): 8.05-7.43 (m, 5H), 4.57 (d, 1H), 4.13 (d, 1H), 2.79 (s, 3H) ppm.

Example 7.1

Preparation of 4-[5-(3,5-dichloro-phenyl)-4-(1-hydroxy-ethyl)-5-trifluoro-methyl-4,5-dihydro-isoxazol-3-yl]-2-methyl-benzoic acid methyl ester

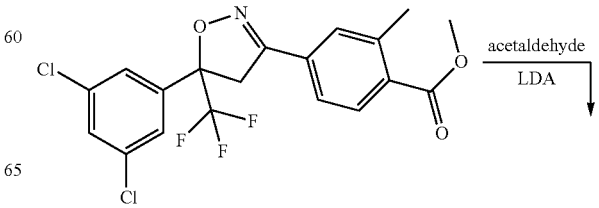

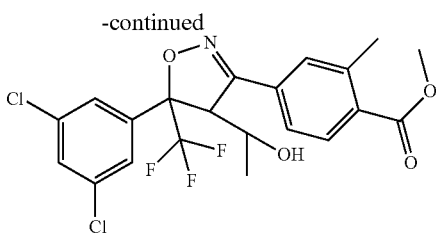

To a solution of N,N-diisopropylamine (0.24 ml) in dry tetrahydrofuran (6 ml) stirred under argon at 0° C., was added butyl lithium (2.5M in hexane) (0.80 ml). The solution was stirred at 0° C. for 30 minutes then was cooled to −85° C. To this solution was added a solution of 4-[5-(3,5-dichloro-phenyl)-5-trifluoromethyl-4,5-dihydro-isoxazol-3-yl]-2-methyl-benzoic acid methyl ester (preparation described in, for example, EP 1,731,512) (404 mg) in dry tetrahydrofuran (3 ml). The reaction mixture was stirred at −85° C. until deprotonation was completed as monitored by thin layer chromatography. Then, to this solution was added acetaldehyde (0.14 ml) and the reaction mixture was stirred at −85° C. for 1.5 hours. The reaction was quenched by addition of aqueous ammonium chloride (saturated) at −85° C. The mixture allowed to warm to ambient temperature and was then extracted with dichloromethane. The combined organic extracts were dried over magnesium sulfate and concentrated. The residue was purified by chromatography on silica gel (eluent: heptane/diethyl ether 60:40) to give 4-[5-(3,5-dichloro-phenyl)-4-(1-hydroxy-ethyl)-5-trifluoromethyl-4,5-dihydro-isoxazol-3-yl]-2-methyl-benzoic acid methyl ester (290 mg) as a white solid. $^1$H-NMR (CDCl$_3$, 400 MHz): 7.98-7.96 (d, 1H), 7.60-7.45 (m, 5H), 4.09-4.08 (m, 1H), 3.96-3.91 (m, 1H), 3.91 (s, 3H), 2.63 (s, 3H), 1.07 and 0.94 (d, 3H).

Example 7.2

Preparation of 4-[5-(3,5-dichloro-phenyl)-4-ethylidene-5-trifluoromethyl-4,5-dihydro-isoxazol-3-yl]-2-methyl-benzoic acid

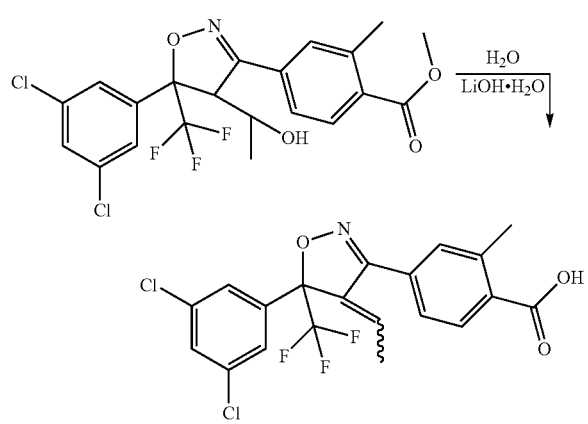

A mixture of 4-[5-(3,5-dichloro-phenyl)-4-(1-hydroxy-ethyl)-5-trifluoromethyl-4,5-dihydro-isoxazol-3-yl]-2-methyl-benzoic acid methyl ester (Example 7.1) (0.242 g, 0.51 mmol), lithium hydroxide monohydrate (0.06 g, 1.4 mmol), tetrahydrofuran (5 ml) and water (5 ml) was stirred at ambient temperature for 2 days. Then further portions of lithium hydroxide monohydrate were added to complete the reaction. In total, 545 mg of lithium hydroxide monohydrate were added over 5 days. The mixture was concentrated and the residue dissolved in water. The solution was acidified by addition of aqueous hydrochloric acid (1N) and extracted with ethyl acetate. The combined organic extracts were dried over magnesium sulfate and concentrated to give a residue which was used without further purification in the following step. LC-MS showed the presence of 4-[5-(3,5-dichloro-phenyl)-4-ethylidene-5-trifluoromethyl-4,5-dihydro-isoxazol-3-yl]-2-methyl-benzoic acid: RT=2.20 min, m/z=442/444/446 (M−H$^+$).

Example 8.1

Preparation of 8-bromo-4-[5-(3,5-dichloro-phenyl)-5-trifluoromethyl-4,5-dihydro-isoxazol-3-yl]-naphthalene-1-carboxylic acid methyl ester

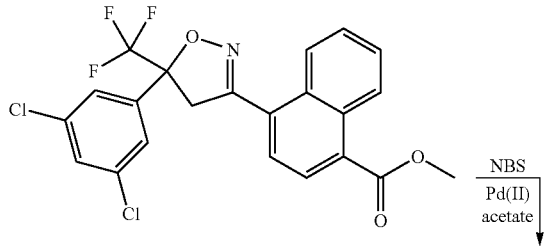

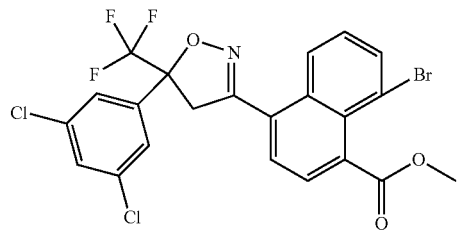

A sealed tube purged with argon was charged with 4-[5-(3,5-dichloro-phenyl)-5-trifluoromethyl-4,5-dihydro-isoxazol-3-yl]-naphthalene-1-carboxylic acid methyl ester (preparation described in, for example, WO 2007/079162) (468 mg), palladium(II) acetate (23 mg), N-bromosuccinimide ("NBS") (23 mg) and acetic acid (5 ml). The tube was heated at 100° C. under vigorous stirring for 24 hours. The reaction mixture was cooled to ambient temperature, diluted with water then extracted with ethyl acetate (3×25 ml). The combined organic extracts were washed with water and brine, treated with charcoal, dried over sodium sulfate and concentrated. The residue was purified by column chromatography on silica gel (eluent: dichloromethane/cyclohexane) to afford 8-bromo-4-[5-(3,5-dichloro-phenyl)-5-trifluoromethyl-4,5-dihydro-isoxazol-3-yl]-naphthalene-1-carboxylic acid methyl ester. MS [MH+] 548.

Example 8.2

Preparation of 8-bromo-4-[5-(3,5-dichloro-phenyl)-5-trifluoromethyl-4,5-dihydro-isoxazol-3-yl]-naphthalene-1-carboxylic acid

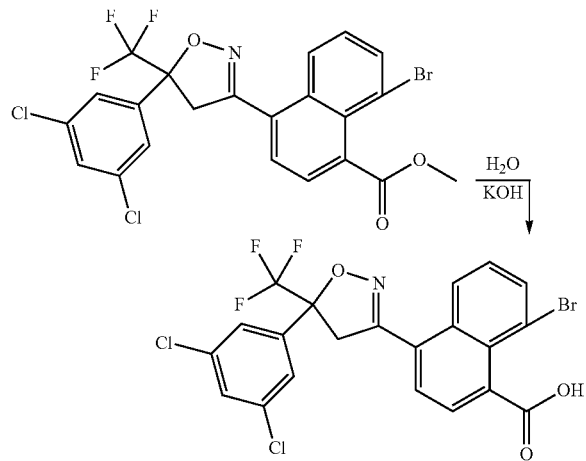

To a solution of 8-bromo-4-[5-(3,5-dichloro-phenyl)-5-trifluoromethyl-4,5-dihydro-isoxazol-3-yl]-naphthalene-1-carboxylic acid methyl ester (Example 8.1) (400 mg) in tetrahydrofuran (3.5 ml) was added a solution of potassium hydroxide (1.9 g) in methanol (3.5 ml) and water (3.5 ml). The reaction mixture was stirred at ambient temperature for 2 hours. The reaction mixture was then acidified by addition of aqueous hydrochloric acid (4N) and the mixture extracted with ethyl acetate (3×10 ml). The combined organic extracts were washed with water (3×10 ml) and brine, dried over sodium sulfate and concentrated to give 8-bromo-4-[5-(3,5-dichloro-phenyl)-5-trifluoromethyl-4,5-dihydro-isoxazol-3-yl]-naphthalene-1-carboxylic acid (342 mg). LC-MS: RT=2.41 min, [M−H]⁻=532/534, Method A.

Example 9.1

Preparation of 5-bromo-1-naphtoic acid

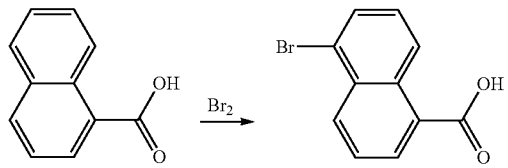

To a solution of 1-naphtoic acid (commercially available) (15 g) in acetic acid (37 ml) was added dropwise bromine (4.5 ml). The reaction mixture was heated at reflux for 4 hours. The reaction mixture was then cooled to ambient temperature and stored at ambient temperature for 16 hours. The solids were isolated by filtration and washed with acetic acid and then ethanol to give 5-bromo-1-naphtoic acid (10.8 g) as a white solid. 1H-NMR (DMSO, 400 MHz): 8.85 (d, 1H), 8.40 (d, 1H), 8.21 (d, 1H), 7.98 (d, 1H), 7.76 (m, 1H), 7.55 (m, 1H).

Example 9.2

Preparation of 5-bromo-1-naphtoic acid tert-butyl ester

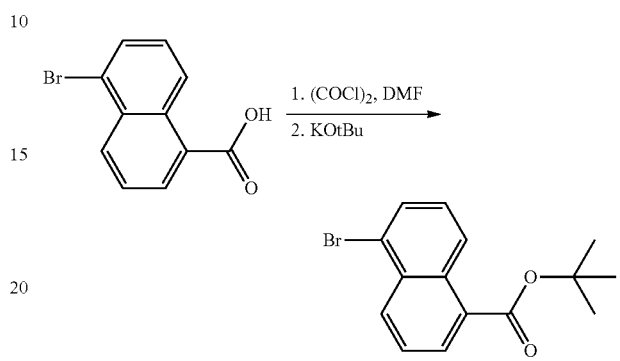

To a suspension of 5-bromo-1-naphtoic acid (Example 9.1) (10.8 g) in dichloromethane (93 ml) containing 3 drops of dimethylformamide was added oxalyl chloride (4 ml) and the reaction mixture stirred at ambient temperature for 6 hours. The solution was concentrated to afford a white solid which was re-dissolved in tetrahydrofuran. The solution was cooled to 2° C. and a solution of potassium tert-butoxide (7.2 g) in tetrahydrofuran (148 ml) was added dropwise and the reaction mixture stirred at ambient temperature for 3 hours. The solution was poured onto ice and extracted with ethyl acetate. The combined organic extracts were washed with water, dried over sodium sulfate and concentrated. The residue was purified by column chromatography on silica gel (eluent: cyclohexane/ethyl acetate) to give 5-bromo-1-naphtoic acid tert-butyl ester (12 g). 1H-NMR (CDCl₃, 400 MHz): 8.82 (d, 1H), 8.46 (d, 1H), 8.11 (d, 1H), 7.72 (d, 1H), 7.60 (m, 1H), 7.40 (m, 1H), 1.70 (s, 9H).

Example 9.3

Preparation of 5-formyl-1-naphtoic acid tert-butyl ester

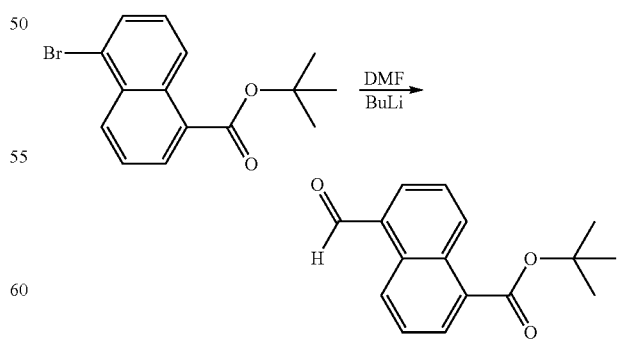

To a solution of 5-bromo-1-naphtoic acid tert-butyl ester (Example 9.2) (6.1 g) in dry tetrahydrofuran (54 ml) cooled to −100° C. was added a solution of butyl lithium (1.6M in hexane) (12.5 ml) dropwise at −100° C., followed by addition of dimethyl-formamide ("DMF") (2.77 ml) at −100° C. The reaction mixture was stirred at −95° C. for 75 minutes. The reaction was quenched by addition of aqueous ammonium chloride (saturated) (8 ml) at −90° C. The mixture was stirred for 10 minutes at −90° C., warmed to 0° C. and poured onto a mixture of ice and water. The mixture was allowed to warm to ambient temperature and then extracted twice with ethyl acetate. The combined organic extracts were washed with water, dried over sodium sulfate and concentrated to give 5-formyl-1-naphtoic acid tert-butyl ester (3 g) as yellow oil. 1H-NMR (CDCl$_3$, 400 MHz): 10.35 (s, 1H), 9.50 (s, 1H), 9.18 (d, 1H), 8.15 (d, 1H), 8.00 (d, 1H), 7.65-7.75 (m, 2H), 1.65 (s, 9H).

Example 9.4

Preparation of 5-(hydroxyimino-methyl)-1-naphtoic acid tert-butyl ester

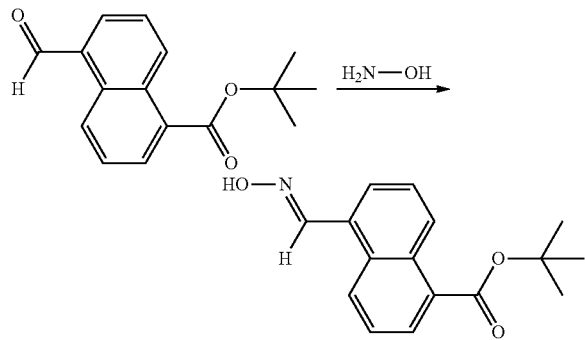

To a solution of 5-formyl-1-naphtoic acid tert-butyl ester (Example 9.3) (1.5 g) in ethanol (7.6 ml) was added aqueous hydroxylamine (50% w/v) (0.48 ml) and the reaction mixture was stirred at ambient temperature for 16 hours. The reaction mixture was concentrated and the residue was purified by column chromatography on silica gel (eluent: cyclohexane/ethyl acetate) to give 5-(hydroxyimino-methyl)-1-naphtoic acid tert-butyl ester (1.4 g). 1H-NMR (CDCl$_3$, 400 MHz): 8.90 (d, 1H), 8.81 (s, 1H), 8.62 (d, 1H), 8.10 (d, 1H), 7.80 (d, 1H), 7.50-7.65 (m, 2H), 1.70 (s, 9H).

Example 9.5

Preparation of 5-[5-(3,5-dichloro-phenyl)-5-trifluoromethyl-4,5-dihydro-isoxazol-3-yl]-naphthalene-1-carboxylic acid tert-butyl ester

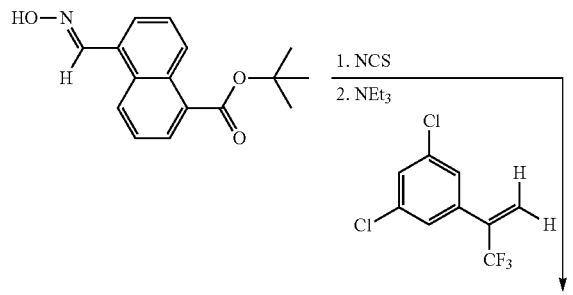

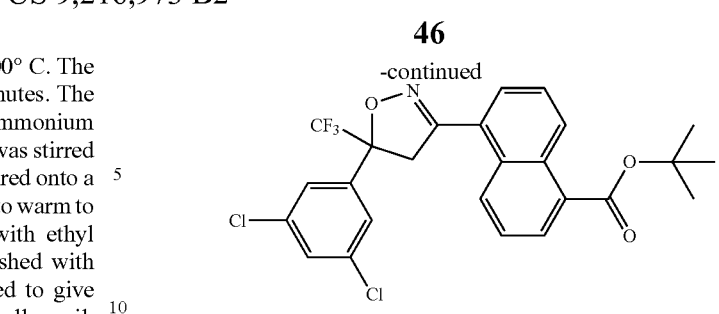

To a solution of 5-(hydroxyimino-methyl)-1-naphtoic acid tert-butyl ester (Example 9.4) (1.4 g) in dimethylformamide (3.4 ml) was added at 0° C. N-chloro-succinimide ("NCS") (759 mg). The reaction mixture was warmed to ambient temperature and stirred at ambient temperature for 30 minutes. The reaction mixture was diluted with water and extracted with ethyl acetate. The combined organic extracts were washed with water and brine, dried over sodium sulfate and concentrated. The residue was purified by column chromatography on silica gel (eluent: cyclohexane/ethyl acetate) to give 5-(chloroxime-methyl)-1-naphtoic acid tert-butyl ester. The 5-(chloroxime-methyl)-1-naphtoic acid tert-butyl ester was dissolved in dimethyl-formamide (2 ml) and a solution of 1,3-dichloro-5-(1-trifluoromethyl-vinyl)-benzene (preparation described in, for example, EP 1,731,512) (1.7 g) and triethylamine in dimethylformamide (2 ml) was added dropwise. The reaction mixture was stirred at ambient temperature for 16 hours. The reaction mixture was diluted with water and extracted with ethyl acetate. The combined organic extracts were dried over sodium sulfate and concentrated. The residue was purified by column chromatography on silica gel (eluent: cyclohexane/ethyl acetate) to give 5-[5-(3,5-dichloro-phenyl)-5-trifluoromethyl-4,5-dihydro-isoxazol-3-yl]-naphthalene-1-carboxylic acid tert-butyl ester. 1H-NMR (CDCl$_3$, 400 MHz): 8.90 (s, 1H), 8.62 (d, 1H), 7.45-7.70 (m, 5H), 7.45 (s, 1H), 7.80 (d, 1H), 4.30 (d, 1H), 3.90 (d, 1H), 1.70 (s, 9H).

Example 9.6

Preparation of 5-[5-(3,5-dichloro-phenyl)-5-trifluoromethyl-4,5-dihydro-isoxazol-3-yl]-naphthalene-1-carboxylic acid

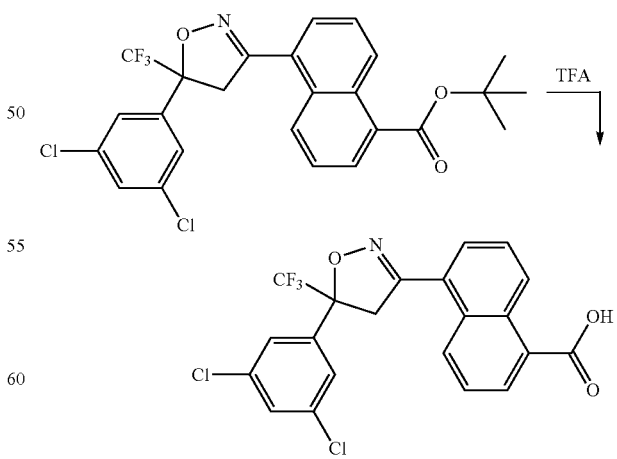

To a stirred solution of 5-[5-(3,5-dichloro-phenyl)-5-trifluoromethyl-4,5-dihydro-isoxazol-3-yl]-naphthalene-1-carboxylic acid tert-butyl ester (Example 9.5) (1.0 g) in dichloromethane (2 ml) was added trifluoroacetic acid (2 ml) and the reaction mixture was stirred at ambient temperature for 4 hours. The reaction mixture was concentrated to give a solid which was washed with cyclohexane to give 5-[5-(3,5-dichloro-phenyl)-5-trifluoromethyl-4,5-dihydro-isoxazol-3-yl]-naphthalene-1-carboxylic acid (0.76 g). 1H-NMR (DMSO, 400 MHz): 8.95 (m, 2H), 8.20 (d, 1H), 7.90 (d, 1H), 7.65-7.80 (m, 5H), 4.50 (q, 2H).

Example 10.1

Preparation of 4-bromo-3-methyl-benzylamine

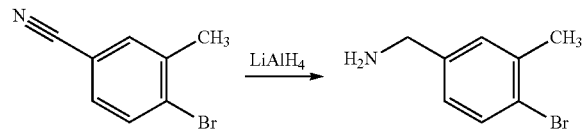

To a solution of 4-bromo-3-methyl-benzonitrile (commercially available) (15 g) in diethyl ether (150 ml) under an argon atmosphere was added a solution of lithium aluminum hydride in diethyl ether (1M) (150 ml) at ambient temperature. The reaction mixture was stirred at 40° C. for 2 hours. Then the reaction mixture was cooled to 0° C. and quenched by successive addition of water (10.5 ml), aqueous sodium hydroxide (20% w/v) (7.5 ml) and water (37.5 ml). The phases were separated. The organic phase was filtered through a plug of silica gel and the filtrate concentrated to give 4-bromo-3-methyl-benzylamine (15.11 g) as a yellow oil. 1H-NMR (400 MHz, CDCl$_3$): 7.47 (d, 1H), 7.19 (s, 1H), 6.98 (d, 1H), 3.80 (s, 2H), 2.39 (s, 3H) ppm.

Example 10.2

Preparation of N-(4-bromo-3-methyl-benzyl)-formamide

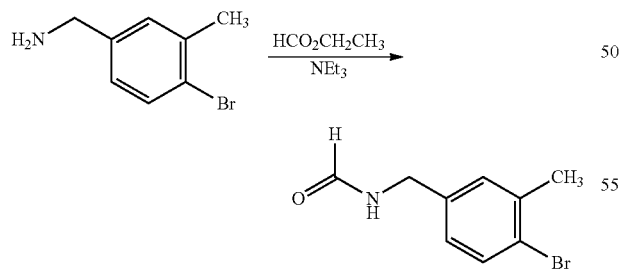

To a solution of 4-bromo-3-methyl-benzylamine (Example 10.1) (15.11 g) in ethyl formate (150 ml) was added triethylamine (1.5 ml) at ambient temperature. The reaction mixture was stirred at reflux for 16 hours. The reaction mixture was concentrated and the residue was triturated with diisopropyl ether/heptane (1:1) (100 ml) to give N-(4-bromo-3-methyl-benzyl)-formamide (14.04 g) as a white solid. 1H-NMR (400 MHz, CDCl$_3$): 8.28 (s, 1H), 7.49 (m, 1H), 7.16 (s, 1H), 6.97 (m, 1H), 5.85 (s, 1H), 4.42 (m, 2H), 2.39 (s, 3H) ppm.

Example 10.3

Preparation of 1-bromo-4-isocyanomethyl-2-methyl-benzene

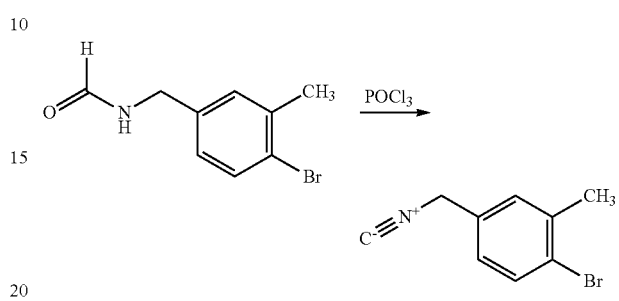

To a solution of N-(4-bromo-3-methyl-benzyl)-formamide (Example 10.2) (4.3 g) in dichloromethane (70 ml) was added a solution of phosphorus oxychloride (2.8 g) in dichloromethane (15 ml) at 0-5° C. The reaction mixture was stirred at ambient temperature for 16 hours. The reaction mixture was poured onto a mixture of ice and water (400 ml), and sodium hydrogen carbonate (saturated) (100 ml) and ethyl acetate (250 ml) were added. The phases were separated and the organic phase was washed with brine, dried over sodium sulfate and concentrated to give 1-bromo-4-isocyanomethyl-2-methyl-benzene (4.52 g) as a brown oil. 1H-NMR (400 MHz, CDCl$_3$): 7.54 (m, 1H), 7.22 (s, 1H), 7.03 (m, 1H), 4.57 (s, 2H), 2.42 (s, 3H) ppm.

Example 10.4

Preparation of 2-(4-bromo-3-methyl-phenyl)-4-(3,5-dichloro-phenyl)-4-trifluoromethyl-3,4-dihydro-2H-pyrrole

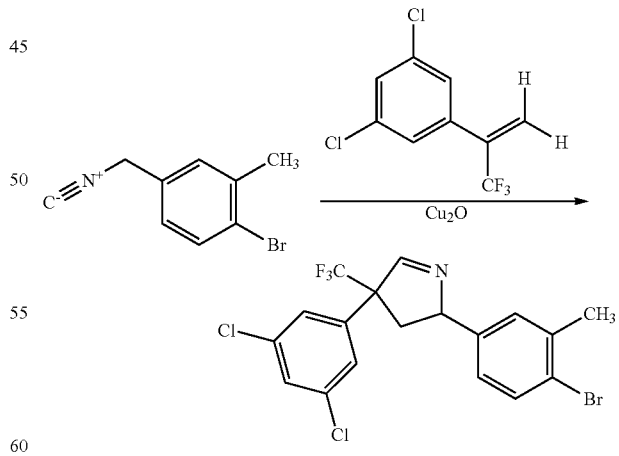

A mixture of 1,3-dichloro-5-(1-trifluoromethyl-vinyl)-benzene (preparation described in, for example, EP 1,731,512) (8.03 g), 1-bromo-4-isocyanomethyl-2-methyl-benzene (Example 10.3) (4.16 g) and copper(I) oxide (0.13 g) in toluene (50 ml) was stirred at 110° C. for 16 hours. The reaction mixture was concentrated and the residue purified by chromatography on silica gel (eluent: ethyl acetate/heptane) to give 2-(4-bromo-3-methyl-phenyl)-4-(3,5-dichloro-phenyl)-4-trifluoromethyl-3,4-dihydro-2H-pyrrole (2.39 g). 1H-NMR (400 MHz, CDCl₃): 7.39-6.86 (m, 7H), 5.39-4.98 (m, 1H), 3.24-2.77 (m, 1H), 2.35 (m, 3H), 2.32-2.09 (m, 1H) ppm.

Example 10.5

Preparation of 4-[4-(3,5-dichloro-phenyl)-4-trifluoromethyl-3,4-dihydro-2H-pyrrol-2-yl]-2-methyl-benzoic acid ethyl ester

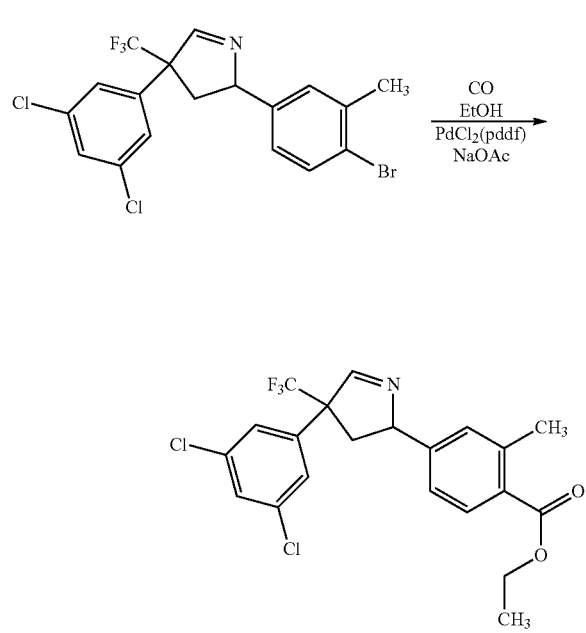

To a solution of 2-(4-bromo-3-methyl-phenyl)-4-(3,5-dichloro-phenyl)-4-trifluoromethyl-3,4-dihydro-2H-pyrrole (Example 10.4) (7.0 g) in a mixture of ethanol (60 ml) and dimethylformamide (20 ml), was added [1,1'-bis(diphenylphosphino)-ferrocene]dichloropalladium(II) ("PdCl₂(dppf)") (0.8 g) and sodium acetate (1.4 g) at ambient temperature. The reaction mixture was stirred in a pressure reactor in an atmosphere of carbon monoxide (6 bar) at 85° C. for 16 hours. The reaction mixture was cooled to ambient temperature, the ethanol was evaporated and aqueous sodium hydrogen carbonate (saturated) (200 ml) and ethyl acetate (250 ml) were added. The phases were separated and the organic phase was dried over sodium sulfate and concentrated. The residue was purified by chromatography on silica gel (eluent: 0-4% v/v methanol in dichloromethane) to give 4-[4-(3,5-dichloro-phenyl)-4-trifluoromethyl-3,4-dihydro-2H-pyrrol-2-yl]-2-methyl-benzoic acid ethyl ester (2.8 g). 1H-NMR (CDCl₃, 400 MHz): 8.04-7.06 (m, 7H), 5.46-5.06 (m, 1H), 4.35 (m, 2H), 3.27-3.79 (m, 1H), 2.59 (m, 3H), 2.38-2.10 (m, 1H), 1.39 (m, 3H) ppm.

Example 10.6

Preparation of 4-[4-(3,5-dichloro-phenyl)-4-trifluoromethyl-3,4-dihydro-2H-pyrrol-2-yl]-2-methyl-benzoic acid

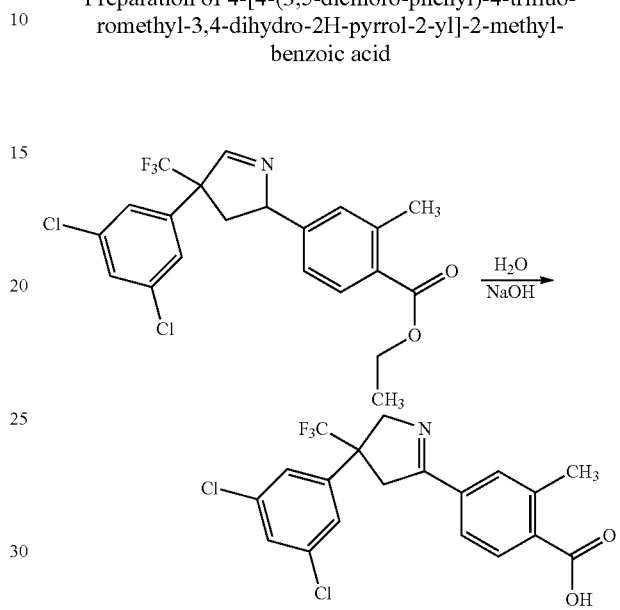

To a solution of 4-[4-(3,5-dichloro-phenyl)-4-trifluoromethyl-3,4-dihydro-2H-pyrrol-2-yl]-2-methyl-benzoic acid ethyl ester (Example 10.5) (2.8 g) in ethanol (40 ml) was added a solution of sodium hydroxide (0.51 g) in water (15 ml). The reaction mixture was stirred at reflux for 1 hour. After cooling to ambient temperature aqueous hydrochloric acid (1M) (20 ml), water (150 ml) and ethyl acetate (200 ml) was added. The phases were separated and the organic phase was washed with brine, dried over sodium sulfate and concentrated. The residue was recrystallised from diisopropyl ether to give 4-[4-(3,5-dichloro-phenyl)-4-trifluoromethyl-3,4-dihydro-2H-pyrrol-2-yl]-2-methyl-benzoic acid (2.02 g) as a white solid. 1H-NMR (d₆-DMSO, 400 MHz): 13.07 (s, 1H), 7.91-7.58 (m, 6H), 4.85 (d, 1H), 4.44 (d, 1H), 3.92-3.35 (m, 2H), 2.58 (s, 3H) ppm.

Example 11.1

Preparation of 4-[5-(3,5-dichloro-phenyl)-5-trifluoromethyl-4,5-dihydro-isoxazol-3-yl]-2-methyl-naphthalene-1-carboxylic acid

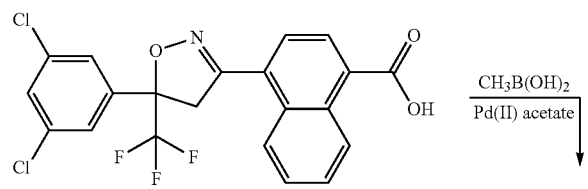

-continued

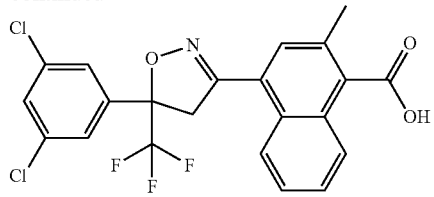

A sealed tube purged with argon was charged with 4-[5-(3,5-dichloro-phenyl)-5-trifluoromethyl-4,5-dihydro-isoxazol-3-yl]-naphthalene-1-carboxylic acid (preparation described in, for example, WO 2007/079162) (454 mg), methyl boronic acid (180 mg), palladium(II) acetate (224 mg), benzoquinone (90 mg), silver carbonate (275 mg), potassium hydrogen phosphate (8265 mg) and tert-butanol (4 ml). The tube was heated at 100° C. under vigorous stirring for 24 hours. The reaction mixture was concentrated and the residue acidified by addition of aqueous hydrochloric acid (1N). The mixture was extracted with ethyl acetate (3×25 ml). The combined organic layers were washed with water and brine, treated with charcoal, dried over sodium sulfate and concentrated. The residue was purified by preparative reverse phase HPLC to give 4-[5-(3,5-dichloro-phenyl)-5-trifluoromethyl-4,5-dihydro-isoxazol-3-yl]-2-methyl-naphthalene-1-carboxylic acid (100 mg). LC-MS: RT=2.41 min, [M−H]⁻=466/468, Method A. 1H-NMR (CDCl₃, 400 MHz): 8.8 (m, 1H), 8.1 (m, 1H), 7.7-7.4 (m, 6H), 4.3 (d, 1H), 3.9 (d, 1H), 2.6 (s, 3H).

Example 12.1

Preparation of 4-[5-(3,5-dichloro-phenyl)-4-hydroxy-5-trifluoromethyl-4,5-dihydro-isoxazol-3-yl]-2-methyl-benzoic acid tert-butyl ester To a solution of 4-[5-(3,5-dichloro-phenyl)-5-trifluoromethyl-4,5-dihydro-isoxazol-3-yl]-2-methyl-benzoic acid tert-butyl ester (preparation of similar compounds described in, for example, EP 1,731,512) (2.83 g) in tetrahydrofuran (25 ml) that was stirred at −78° C. for 5 minutes under argon, was slowly added lithium bis(trimethyl-silyl)amide ("LiHMDS") (1M in hexane) (6.9 ml). After 3 hours at −78° C., a cold (−20° C.) solution of 2-benzenesulfonyl-3-phenyl-oxaziridine (commercially available) (2.34 g) in tetrahydrofuran (10 ml) was added quickly. The temperature was kept below −65° C. for 4 hours and 30 minutes. The reaction was quenched by addition of aqueous ammonium chloride (saturated) at −78° C. tent-Butyl methyl ether ("TBME") was added and the phases were separated. The organic layer was washed successively with ammonium chloride and brine, dried over magnesium sulfate and concentrated. The residue was purified by column chromatography on silica gel (eluent: heptane/TBME 9:1) to give 4-[5-(3,5-dichloro-phenyl)-4-hydroxy-5-trifluoromethyl-4,5-dihydro-isoxazol-3-yl]-2-methyl-benzoic acid tert-butyl ester (738 mg) as a white solid.

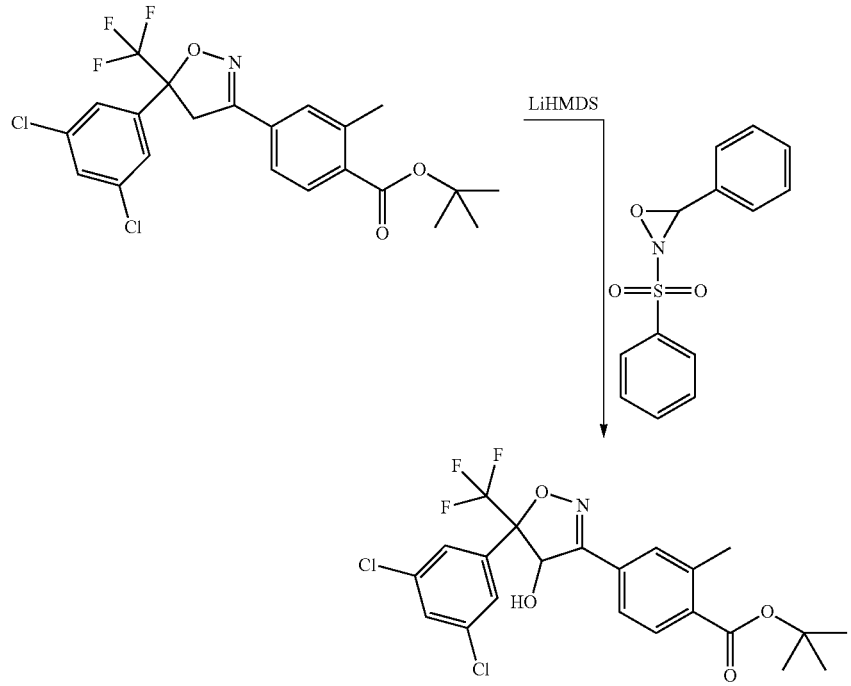

Example 12.2

Preparation of 4-[5-(3,5-dichloro-phenyl)-4-hydroxy-5-trifluoromethyl-4,5-dihydro-isoxazol-3-yl]-2-methyl-benzoic acid

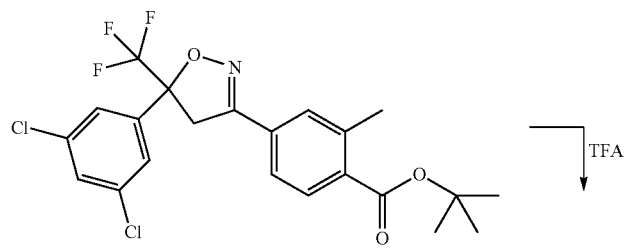

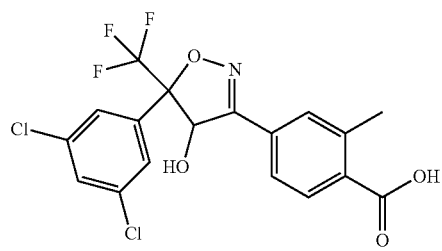

To a solution of 4-[5-(3,5-dichloro-phenyl)-4-hydroxy-5-trifluoromethyl-4,5-dihydro-isoxazol-3-yl]-2-methyl-benzoic acid tert-butyl ester (Example 12.1) (500 mg) in dichloromethane (20 ml) was added trifluoroacetic acid ("TFA") (4 ml) and the reaction mixture was stirred at ambient temperature for 16 hours. To the reaction mixture was diluted with water and the phases were separated. The organic layer was washed with water and brine, dried over magnesium sulfate and concentrated. The residue was suspended in diisopropyl ether/pentane (1:3). The solids were isolated by filtration and washed with pentane to give 4-[5-(3,5-dichloro-phenyl)-4-hydroxy-5-trifluoromethyl-4,5-dihydro-isoxazol-3-yl]-2-methyl-benzoic acid (395 mg) as a white solid. M.p. 215-217° C. 1H-NMR (CDCl$_3$, 400 MHz): 7.98 (d, 1H), 7.72 (s, 1H), 7.69 (s, 1H), 7.52 (s, 2H), 7.40 (s, 1H), 5.76 (s, 1H), 2.61 (s, 3H).

Example 13.1

Preparation of 4-[3-(3,5-dichloro-phenyl)-4,4,4-trifluoromethyl-1-hydroxyimino-but-2-enyl]-2-methyl-benzoic acid tert-butyl ester

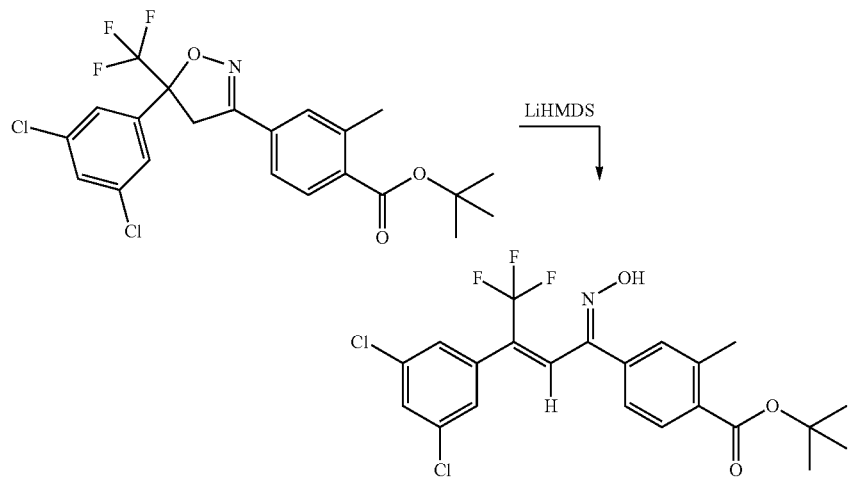

To a solution of 4-[5-(3,5-dichloro-phenyl)-5-trifluoromethyl-4,5-dihydro-isoxazol-3-yl]-2-methyl-benzoic acid tert-butyl ester (preparation of similar compounds described in, for example, EP 1,731,512) (5 g) in dry tetrahydrofuran (110 ml) under at atmosphere of argon was added lithium bis (trimethylsilyl)amide ("LiHMDS") (1M in tetrahydrofuran) (11 ml) at ambient temperature. Then, more lithium bis(trimethyl-silyl)amide ("LiHMDS") (1M in tetrahydrofuran) (6 ml in total) was added portionwise to the reaction mixture until completion of the reaction was observed. Then, the reaction mixture was quenched by addition of aqueous ammonium chloride (saturated). The mixture was extracted several times with diethyl ether. The combined organic extracts were dried over magnesium sulfate and concentrated. The residue was purified by column chromatography on silica gel (eluent: heptane/diethyl ether 9:1) to give 4-[3-(3,5-dichloro-phenyl)-4,4,4-trifluoromethyl-1-hydroxyimino-but-2-enyl]-2-methyl-benzoic acid tert-butyl ester (2 g).

Example 13.2

Preparation of 4-[5-(3,5-dichloro-phenyl)-4-hydroxyimino-5-trifluoromethyl-4,5-dihydro-isoxazol-3-yl]-2-methyl-benzoic acid tert-butyl ester

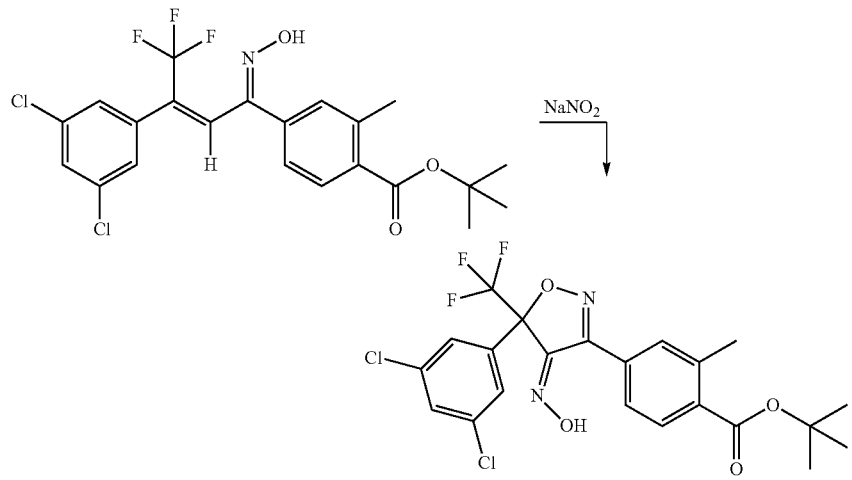

To a solution of 4-[3-(3,5-dichloro-phenyl)-4,4,4-trifluoromethyl-1-hydroxyimino-but-2-enyl]-2-methyl-benzoic acid tert-butyl ester (Example 13.1) (1 g) in a mixture of ethanol/water/tetrahydrofuran (1:2:2) (25 ml) was added sodium nitrite (500 mg). The reaction mixture was acidified to pH 1.5 by addition of aqueous hydrochloric acid (2M). The reaction mixture was stirred at ambient temperature for 24 hours. Further sodium nitrite (400 mg) was added and the reaction mixture acidified to pH 1.5 by addition of further aqueous hydrochloric acid (2M) and the reaction mixture was stirred at ambient temperature for 2 hours. Further sodium nitrite (100 mg) was added and the reaction mixture acidified to pH 1.5 by addition of further aqueous hydrochloric acid (2M) and the reaction mixture was stirred at ambient temperature for 24 hours. Further sodium nitrite (200 mg) was added and the reaction mixture acidified to pH 1.5 by addition of further aqueous hydrochloric acid (2M) and the reaction mixture was stored at ambient temperature for 48 hours. The reaction mixture was diluted with dichloromethane and water. The phases were separated and the organic layer was washed successively with water and brine, dried over magnesium sulfate and concentrated. The residue was purified by column chromatography on silica gel (eluent: heptane/diethyl ether 9:1) to give 4-{5-(3,5-dichloro-phenyl)-4-hydroxyimino-5-trifluoromethyl-4,5-dihydro-isoxazol-3-yl}-2-methyl-benzoic acid tert-butyl ester (512 mg) as yellow solid.

Example 13.3

Preparation of 4-[5-(3,5-dichloro-phenyl)-4-hydroxyimino-5-trifluoromethyl-4,5-dihydro-isoxazol-3-yl]-2-methyl-benzoic acid

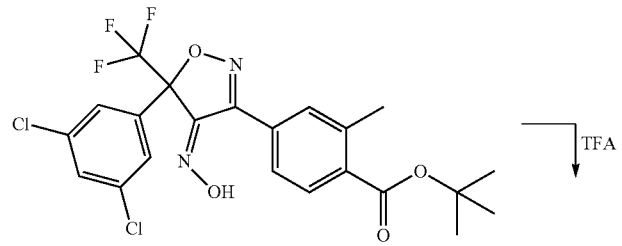

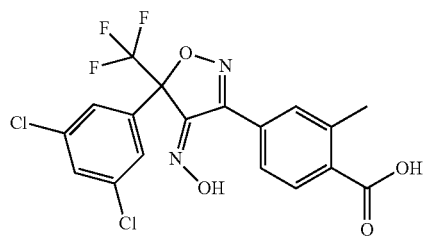

To a solution of 4-[5-(3,5-dichloro-phenyl)-4-hydroxyimino-5-trifluoromethyl-4,5-dihydro-isoxazol-3-yl]-2-methyl-benzoic acid tert-butyl ester (Example 13.2) (634 mg) in dichloromethane (4 ml) was added trifluoroacetic acid ("TFA") (0.2 ml) and the reaction mixture was stirred at ambient temperature for 8 hours. Further trifluoroacetic acid (0.2 ml) was added and the reaction mixture was stirred at ambient temperature for 16 hours. The reaction mixture was diluted with ethyl acetate and water and the phases were separated. The organic layer was washed successively with water and brine, dried over magnesium sulfate, and concentrated to give 4-[5-(3,5-dichloro-phenyl)-4-hydroxyimino-5-trifluoromethyl-4,5-dihydro-isoxazol-3-yl]-2-methyl-benzoic acid (554 mg) as a yellow foam. 1H-NMR (CDCl$_3$, 400 MHz): 8.94 (s, 1H), 8.10 (d, 1H), 7.90 (m, 2H), 7.59 (m, 2H), 7.44 (m, 1H), 2.69 (s, 3H).

Example 14.1

Preparation of 4-[5-(3,5-dichloro-phenyl)-4-fluoro-5-trifluoromethyl-4,5-dihydro-isoxazol-3-yl]-2-methyl-benzoic acid tert-butyl ester

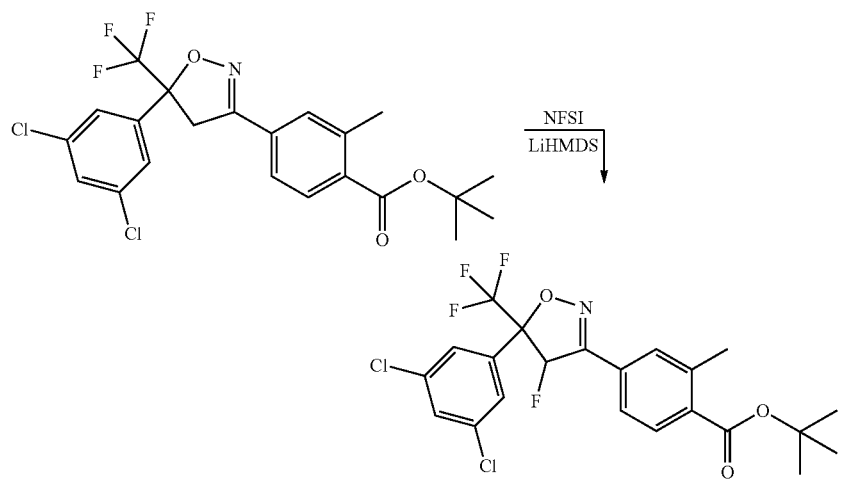

To a solution of 4-[5-(3,5-dichloro-phenyl)-5-trifluoromethyl-4,5-dihydro-isoxazol-3-yl]-2-methyl-benzoic acid tert-butyl ester (preparation of similar compounds described in, for example, EP 1,731,512) (500 mg) in tetrahydrofuran (6 ml) that was stirred at −78° C. for 15 minutes under argon, was slowly added lithium bis(trimethyl-silyl)amide ("LiHMDS") (1M in hexane) (1.1 ml). The reaction mixture was stirred at −78° C. for 1.5 hours. Then N-fluorobenzenesulfonimide ("NFSI") (433 mg) was added quickly and the reaction mixture was stirred at −78° C. for 2 hours. The reaction was quenched by addition of aqueous ammonium chloride (saturated) at −78° C. tent-Butyl methyl ether ("TBME") was added and the phases were separated. The organic layer was washed successively with aqueous ammonium chloride (saturated) and brine, dried over magnesium sulfate and concentrated. The residue was purified by column chromatography on silica gel (eluent: dichloromethane/heptane 1:2) to give 4-[5-(3,5-dichloro-phenyl)-4-fluoro-5-trifluoromethyl-4,5-dihydro-isoxazol-3-yl]-2-methyl-benzoic acid tert-butyl ester (200 mg) as a colorless oil.

Example 14.2

Preparation of 4-[5-(3,5-dichloro-phenyl)-4-fluoro-5-trifluoromethyl-4,5-dihydro-isoxazol-3-yl]-2-methyl-benzoic acid

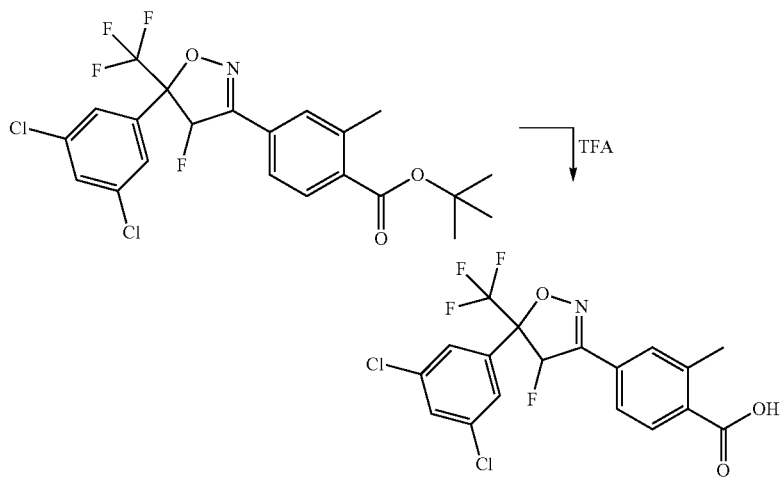

To a solution of 4-[5-(3,5-dichloro-phenyl)-4-fluoro-5-trifluoromethyl-4,5-dihydro-isoxazol-3-yl]-2-methyl-benzoic acid tert-butyl ester (Example 14.1) (310 mg) in dichloromethane (3.1 ml) was added trifluoroacetic acid ("TFA") (0.62 ml). The reaction mixture was stirred at ambient temperature for 16 hours. The reaction mixture was concentrated and the residue taken up in dichloromethane and water. The phases were separated and the organic layer was washed successively with water and brine, dried over magnesium sulfate, and concentrated to give a 1:1 mixture of the diastereoisomers of 4-[5-(3,5-dichloro-phenyl)-4-fluoro-5-trifluoromethyl-4,5-dihydro-isoxazol-3-yl]-2-methyl-benzoic acid (255 mg) as a white solid. 1H-NMR (CDCl$_3$, 400 MHz): 8.13 (2×d, 1H), 7.68 (m, 2H), 7.60 (2×s, 1H), 7.52 (2×s, 1H), 7.48 (m, 1H), 6.48 and 6.35 (2×d, 1H), 2.70 and 2.68 (2×s, 3H).

Example 15.1

5-(3,5-Dichloro-phenyl)-5-methyl-4,5-dihydro-isoxazole-3-carboxylic acid ethyl ester

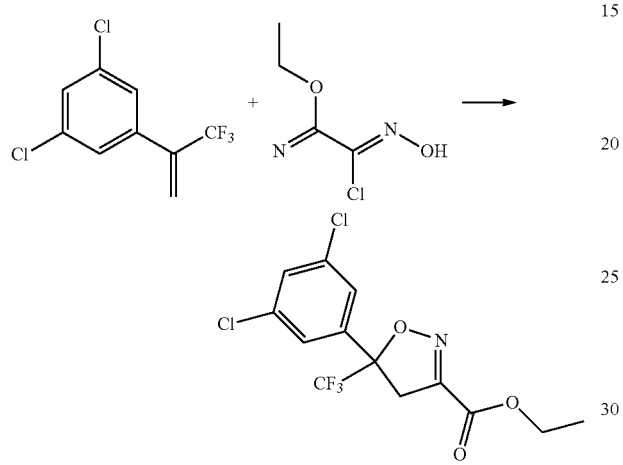

A solution of ethyl chlorooximidoacetate (9.0 g, 59.1 mmol) in ethylacetate (30 ml) was added at ambient temperature with a syringe pump over a period of 40 h to a suspension of 1,3-dichloro-5-(3,3,3-trifluoroprop-1-en-2-yl)benzene (prepared according to WO 2005/085216) (9.5 g, 39.4 mmol) and sodium hydrogen carbonate (15.9 g, 189 mmol) in ethylacetate (85 ml). The reaction mixture was diluted with ethylacetate and washed with water. The organic phase was separated dried over sodium sulfate and concentrated. The residue was purified by chromatography over silica (cyclohexane/ethylacetate; 4/1) to give 8.9 of a yellow oil. $^1$H-NMR (CDCl$_3$, 400 MHz): 7.45 (m, 3H), 4.49 (q, 2H), 3.96 (d, 1H), 3.59 (d, 1H), 1.40 (t, 3H).

Example 15.2

[5-(3,5-Dichloro-phenyl)-5-methyl-4,5-dihydro-isoxazol-3-yl]-methanol

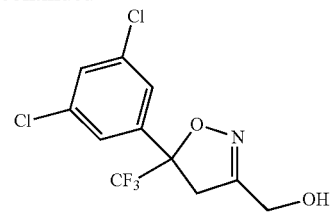

Lithiumborohydride (0.86 g, 39.7 mmol) was added in portions at ambient temperature to a solution of 5-(3,5-dichlorophenyl)-5-trifluoromethyl-4,5-dihydro-isoxazole-3-carboxylic acid ethyl ester (8.8 g, 24.8 mmol) in tetrahydrofuran (100 ml) and a small amount of methanol (1.5 ml). After stirring for 2 h at 40° C. the reaction mixture was cooled to 20° C., made acidic with 2N hydrochloric acid and stirred for 1 h. Solid potassium carbonate was added until the reaction mixture was slightly alkaline. After extraction with ethylacetate the organic phase was separated, dried over sodium sulfate and concentrated to give 7.98 g of a white material which was used in the next step without further purification $^1$H-NMR (CDCl$_3$, 400 MHz): 7.38-7.48 (m, 3H), 4.47 (d, 2H), 3.82 (d, 1H), 3.43 (d, 1H), 1.93 (t, 1H).

Example 15.3

5-(3,5-Dichloro-phenyl)-5-trifluoromethyl-4,5-dihydro-isoxazole-3-carbaldehyde

Manganese dioxide (17.7 g, 203 mmol) was added to a solution of [5-(3,5-dichloro-phenyl)-5-trifluoromethyl-4,5-dihydro-isoxazol-3-yl]-methanol (7.98 g, 25.4 mmol) in chloroform (170 ml). After stirring for 4 h at 60° C. the reaction mixture was cooled to 20° C. and filtered. The filtrate was concentrated and the residue was purified by chromatography over silica (cyclohexane/ethylacetate; 3/1) to give 4.1 g of a yellow oil. 1H-NMR (CDCl₃, 400 MHz): 9.93 (s, 1H) 7.42-7.48 (m, 3H), 3.88 (d, 2H), 3.50 (d, 1H).

Example 15.4

5-(3,5-Dichloro-phenyl)-5-trifluoromethyl-4,5-dihydro-isoxazole-3-carbaldehyde oxime

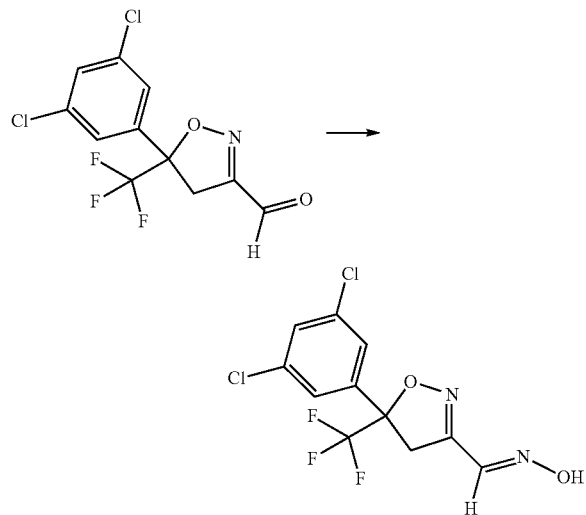

To a solution of 5-(3,5-Dichloro-phenyl)-5-trifluoromethyl-4,5-dihydro-isoxazole-3-carbaldehyde (2 g) in EtOH (4 mL) and H₂O (2 drops), was added aqueous NH₂OH (50% in water, 0.48 mL). The solution was stirred at room temperature for 3 hours then allowed to stand at room temperature for 16 hours. Then the solution was stirred again and more hydroxylamine (0.04 mL) was added. After 3 hours, the reaction was quenched by addition of water. After extraction with ethylacetate, the organic phase was separated, dried over magnesium sulfate and concentrated to give 2.02 g of a yellow solid which was used in the next step without further purification. 1H-NMR (CDCl₃, 400 MHz) shows a mixture of diastereoisomers: 8.07 and 7.94 (s, 1H), 7.43-7.38 (m, 3H), 3.88 (d, 1H), 3.50 (d, 1H).

Example 15.5

5'-(3,5-Dichloro-phenyl)-5'-trifluoromethyl-4',5'-dihydro[3,3']biisoxazolyl-5-carboxylic acid

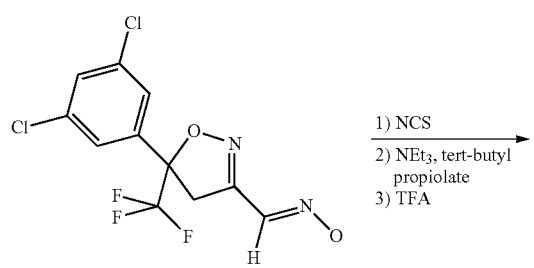

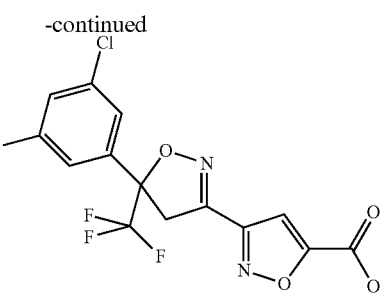

To a solution of 5-(3,5-Dichloro-phenyl)-5-trifluoromethyl-4,5-dihydro-isoxazole-3-carbaldehyde oxime (500 mg) in dimethylformamide (10 mL) under argon at room temperature, was added N-chlorosuccinimide (225 mg). The solution was stirred at room temperature for 30 minutes then was allowed to stand at room temperature for 14 hours.

The reaction was then quenched by addition of water. After extraction with dichloromethane, the organic phase was separated, dried over magnesium sulfate and concentrated to give an orange residue which was used in the next step without further purification.

To a solution of tert-butyl propiolate (2 mL) in chloroform (10 mL) was added a solution of the preceeding residue in chloroform (10 mL), at room temperature. Then triethylamine (0.3 mL) was added. The solution was stirred at room temperature for 30 minutes then was allowed to stand at room temperature for 14 hours.

The reaction was then quenched by addition of water. After extraction with dichloromethane, the organic phase was separated, dried over magnesium sulfate and concentrated to give a yellow oil. The residue was purified by chromatography over silica (heptane/dichloromethane; 1/0 to 1/1) to give 393 mg of 5'-(3,5-Dichloro-phenyl)-5'-trifluoromethyl-4',5'-dihydro-[3,3']biisoxazolyl-5-carboxylic acid tert-butyl ester as a colorless oil. ¹H-NMR (CDCl₃, 400 MHz): 7.46 (m, 2H) 7.44-7.43 (m, 1H), 7.23 (s, 1H), 4.15 (d, 1H), 3.78 (d, 1H), 1.60 (s, 9H).

Similarly to example 14.2, the 5'-(3,5-Dichloro-phenyl)-5'-trifluoromethyl-4',5'-dihydro-[3,3']biisoxazolyl-5-carboxylic acid tert-butyl ester (393 mg) was deprotected with trifluoroacetic acid to give the 5'-(3,5-Dichloro-phenyl)-5'-trifluoromethyl-4',5'-dihydro-[3,3']biisoxazolyl-5-carboxylic acid (331 mg) as a white solid. ¹H-NMR (CDCl₃, 400 MHz): 7.65 (bs, 1H) 7.46 (m, 2H), 7.44-7.42 (m, 2H), 4.17 (d, 1H), 3.81 (d, 1H).

Example 16.1

5-Formyl-2-methyl-2H-pyrazole-3-carboxylic acid methyl ester

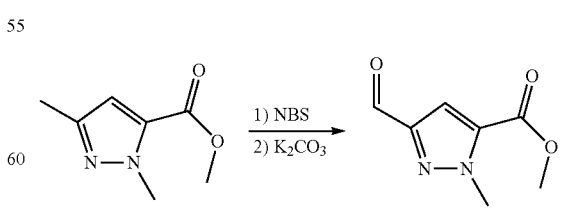

To a solution of 2,5-Dimethyl-2H-pyrazole-3-carboxylic acid methyl ester (2 g) in carbon tetrachloride (100 mL) under argon, was added N-bromosuccinimide (5 g). The reaction mixture was refluxed under argon for 10 minutes then benzoyl peroxide (75% in water, 300 mg) was added. After 1 hour at reflux, more benzoyl peroxide (75% in water, 130 mg) was added and the reaction was refluxed for a further hour. The reaction mixture was then cooled to room temperature, and the solution was filtered. The filtrate was concentrated to give a yellow residue that was then dissolved in water (16 mL). To this solution was added $K_2CO_3$ (500 mg) at room temperature and the reaction mixture was heated at 90 C for one hour.

The reaction was then diluted with ethyl acetate, the aqueous phase was acidified to pH=1 with HCl 1M. After extraction with ethyl acetate, the organic phase was separated, dried over magnesium sulfate and concentrated to give a yellow oil. The residue was purified by chromatography over silica (heptane/diethyl ether; 1/0 to 8/2) to give 5-Formyl-2-methyl-2H-pyrazole-3-carboxylic acid methyl ester (210 mg) as a white solid. $^1$H-NMR (CDCl$_3$, 400 MHz): 9.94 (s, 1H) 7.30 (s, 1H), 4.26 (s, 3H), 3.90 (s, 3H).

Example 16.2

5-[5-(3,5-Dichloro-phenyl)-5-trifluoromethyl-4,5-dihydro-isoxazol-3-yl]-2-methyl-2H-pyrazole-3-carboxylic acid

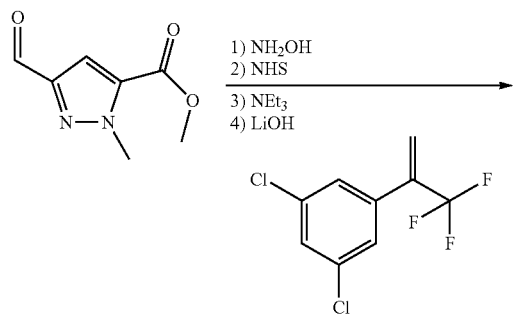

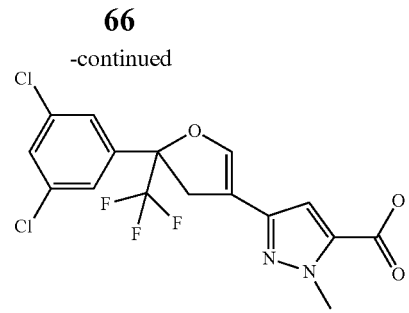

To a solution of 5-Formyl-2-methyl-2H-pyrazole-3-carboxylic acid methyl ester (210 mg) in ethanol (10 mL), was added aqueous NH$_2$OH (50% in water, 0.10 mL). The solution was stirred at room temperature for 4 hours then was concentrated to give a white solid which was then dissolved in dimethylformamide (4 mL). To this solution was added N-chlorosuccinimide (180 mg). The solution was stirred at room temperature for 4 hours. This solution was slowly added to a solution of 1,3-Dichloro-5-(1-trifluoromethyl-vinyl)-benzene (750 mg) (prepared according to WO 2005/085216) in dimethylformamide (6 mL). When the addition was completed, triethylamine (0.2 mL) was added. The solution was stirred at room temperature for 4 hours then the reaction was then quenched by addition of water. After extraction with diethyl ether, the organic phase was separated, dried over magnesium sulfate and concentrated to give an orange oil. The residue was purified by chromatography over silica (heptane/diethyl ether; 1/0 to 7/3) to give 300 mg of 5-[5-(3,5-Dichloro-phenyl)-5-trifluoromethyl-4,5-dihydro-isoxazol-3-yl]-2-methyl-2H-pyrazole-3-carboxylic acid methyl ester as a white solid. $^1$H-NMR (CDCl$_3$, 400 MHz): 7.48 (m, 2H), 7.39-7.38 (m, 1H), 7.23 (s, 1H), 4.17 (s, 3H), 4.14 (d, 1H), 3.89 (s, 3H), 3.75 (d, 1H).

Similarly to example 7.2, 5-[5-(3,5-Dichloro-phenyl)-5-trifluoromethyl-4,5-dihydro-isoxazol-3-yl]-2-methyl-2H-pyrazole-3-carboxylic acid was obtained from the 5-[5-(3,5-Dichloro-phenyl)-5-trifluoromethyl-4,5-dihydro-isoxazol-3-yl]-2-methyl-2H-pyrazole-3-carboxylic acid methyl ester. $^1$H-NMR (CDCl$_3$, 400 MHz): 7.49 (m, 2H), 7.41 (m, 1H), 7.35 (s, 1H), 4.19 (s, 3H), 4.15 (d, 1H), 3.76 (s, 3H).

TABLE A

| Comp No. | Structure | RT (min) | Molecular ion | LC-MS method |
|---|---|---|---|---|
| A1 | 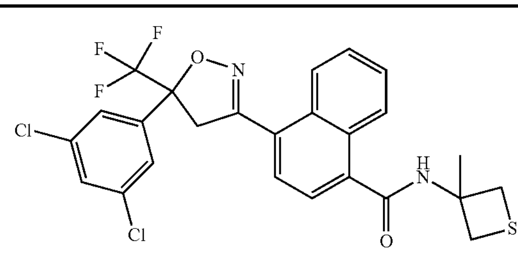 | 2.25 | [M + H]$^+$ = 538 | A |
| A2 | 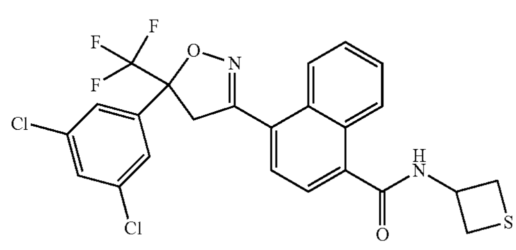 [SMILES: O=C(NC1CSC1)c1ccc(C2=NOC(c3cc(Cl)cc(Cl)c3)(C(F)(F)F)C2)c2ccccc12] | 2.15 | [M + H]$^+$ = 524 | A |

TABLE A-continued

| Comp No. | Structure | RT (min) | Molecular ion | LC-MS method |
|---|---|---|---|---|
| A3 | 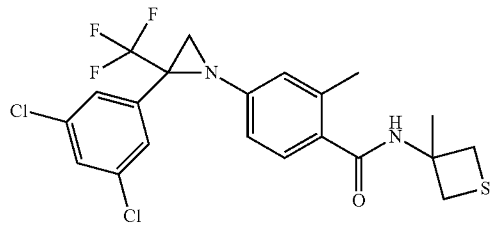 [SMILES: Cc1cc(N2CC2(c2cc(Cl)cc(Cl)c2)C(F)(F)F)ccc1C(=O)NC1(C)CSC1] | 1.98 | [M + H]⁺ = 475 | D |
| A4 | 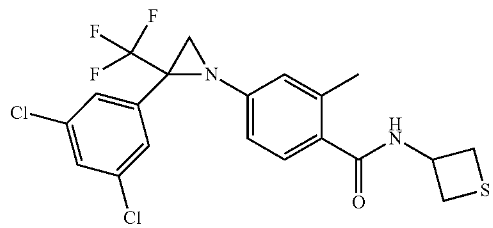 [SMILES: Cc1cc(N2CC2(c2cc(Cl)cc(Cl)c2)C(F)(F)F)ccc1C(=O)NC1CSC1] | 1.85 | [M + H]⁺ = 461 | D |
| A5 | 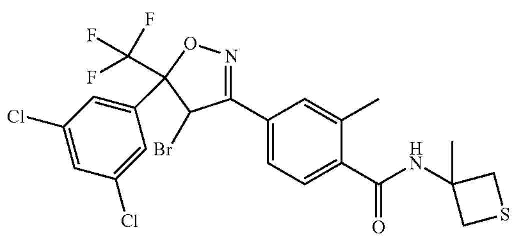 [SMILES: Cc1cc(C2=NOC(c3cc(Cl)cc(Cl)c3)(C(F)(F)F)C2Br)ccc1C(=O)NC1(C)CSC1] | 2.06 | [M + H]⁺ = 580 | E |
| A6 | 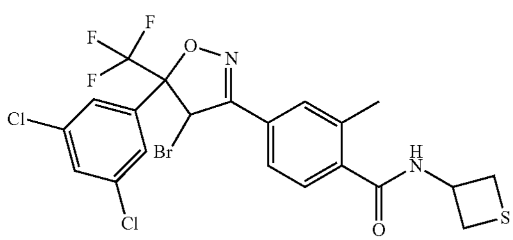 [SMILES: Cc1cc(C2=NOC(c3cc(Cl)cc(Cl)c3)(C(F)(F)F)C2Br)ccc1C(=O)NC1CSC1] | 1.95 | [M + H]⁺ = 566 | E |
| A7 | isomer A | 2.05 | [M + H]⁺ = 585 | E |
| A8 | isomer B | 2.04 | [M + H]⁺ = 585 | E |

TABLE A-continued

| Comp No. | Structure | RT (min) | Molecular ion | LC-MS method |
|---|---|---|---|---|
| A9 | 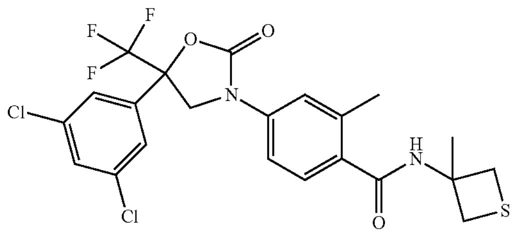 [SMILES: Cc1cc(N2CC(c3cc(Cl)cc(Cl)c3)(C(F)(F)F)OC2=O)ccc1C(=O)NC1(C)CSC1] | 1.87 | [M + H]⁺ = 519 | E |
| A10 | mixture of isomers | 1.55 | [M + H]⁺ = 521 | E |
| A11 | 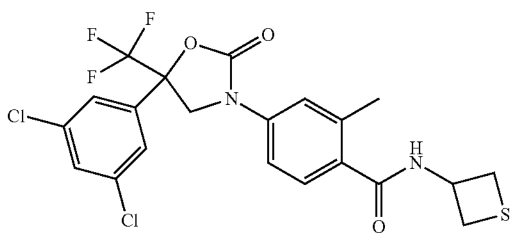 [SMILES: Cc1cc(N2CC(c3cc(Cl)cc(Cl)c3)(C(F)(F)F)OC2=O)ccc1C(=O)NC1CSC1] | 1.79 | [M + H]⁺ = 505 | E |
| A12 | 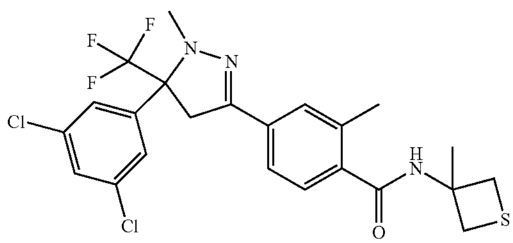 [SMILES: Cc1cc(C2=NN(C)C(c3cc(Cl)cc(Cl)c3)(C(F)(F)F)C2)ccc1C(=O)NC1(C)CSC1] | 2.05 | [M + H]⁺ = 516 | E |
| A13 | mixture of isomers | 1.7 | [M + H]⁺ = 518 | E |
| A14 | 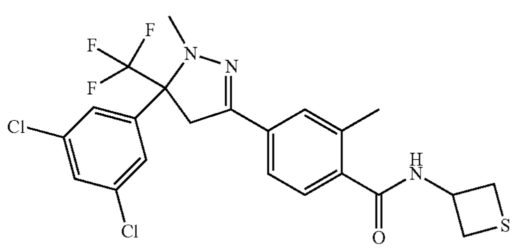 [SMILES: Cc1cc(C2=NN(C)C(c3cc(Cl)cc(Cl)c3)(C(F)(F)F)C2)ccc1C(=O)NC1CSC1] | 1.96 | [M + H]⁺ = 502 | E |

TABLE A-continued

| Comp No. | Structure | RT (min) | Molecular ion | LC-MS method |
|---|---|---|---|---|
| A15 | 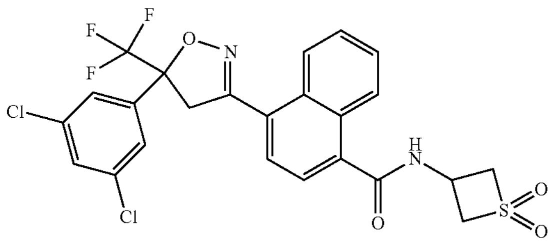 [SMILES: O=C(NC1CS(=O)(=O)C1)c1ccc(C2=NOC(c3cc(Cl)cc(Cl)c3)(C(F)(F)F)C2)c2ccccc12] | 2.11 | [M − H]⁻ = 555 | A |
| A16 | mixture of isomers | 2.05 | [M − H]⁻ = 539 | A |
| A17 | 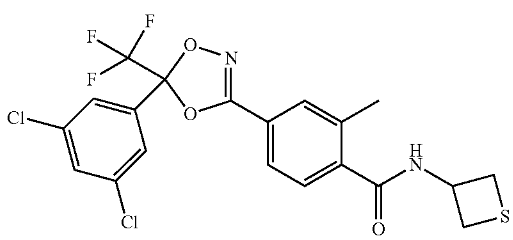 [SMILES: Cc1cc(C2=NOC(c3cc(Cl)cc(Cl)c3)(C(F)(F)F)O2)ccc1C(=O)NC1CSC1] | 2.20 | [M + H]⁺ = 491 | A |
| A18 | mixture of isomers | 3.17 | [M + H]⁺ = 520.1 | E |
| A19 | 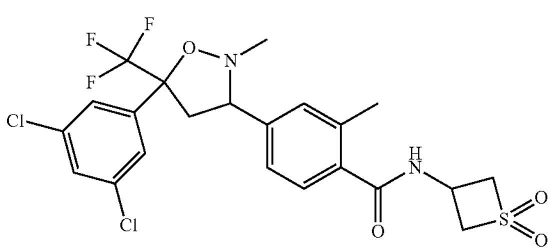 [SMILES: Cc1cc(C2CC(c3cc(Cl)cc(Cl)c3)(C(F)(F)F)ON2C)ccc1C(=O)NC1CS(=O)(=O)C1] | 3.51 | [M + H]⁺ = 536.9 | E |
| A20 | 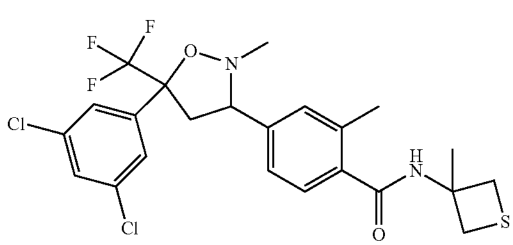 [SMILES: Cc1cc(C2CC(c3cc(Cl)cc(Cl)c3)(C(F)(F)F)ON2C)ccc1C(=O)NC1(C)CSC1] | 4.04 | [M + H]⁺ = 518.9 | E |

TABLE A-continued

| Comp No. | Structure | RT (min) | Molecular ion | LC-MS method |
|---|---|---|---|---|
| A21 | 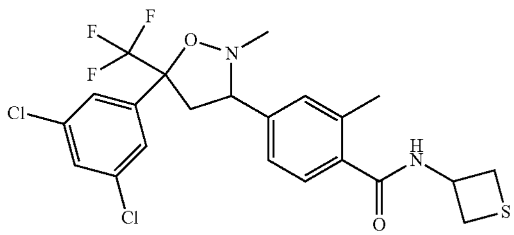 [SMILES: Cc1cc(C2CC(c3cc(Cl)cc(Cl)c3)(C(F)(F)F)ON2C)ccc1C(=O)NC1CSC1] | 3.86 | [M + H]⁺ = 504.9 | E |
| A22 | 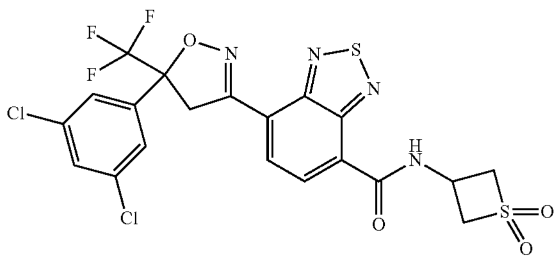 [SMILES: O=C(NC1CS(=O)(=O)C1)c1ccc(C2=NOC(c3cc(Cl)cc(Cl)c3)(C(F)(F)F)C2)c2nsnc12] | 5.52 | [M + H]⁺ = 564 | E |
| A23 | 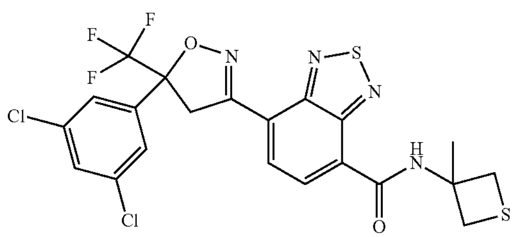 [SMILES: CC1(NC(=O)c2ccc(C3=NOC(c4cc(Cl)cc(Cl)c4)(C(F)(F)F)C3)c3nsnc23)CSC1] | 4.31 | [M + H]⁺ = 547 | E |
| A24 | mixture of isomers | 3.18 | [M + H]⁺ = 549 | E |
| A25 | 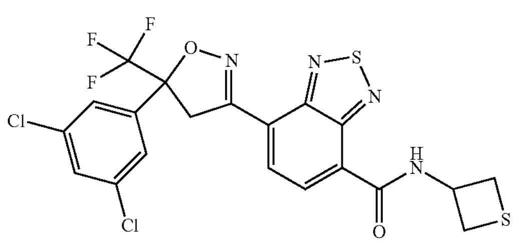 [SMILES: O=C(NC1CSC1)c1ccc(C2=NOC(c3cc(Cl)cc(Cl)c3)(C(F)(F)F)C2)c2nsnc12] | 4.05 | [M + H]⁺ = 533 | E |
| A26 | 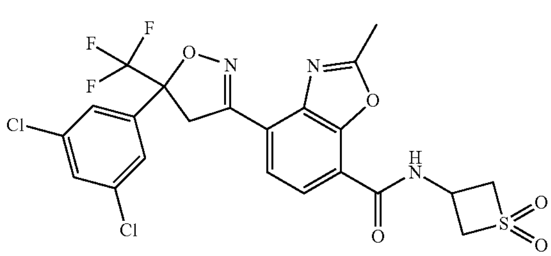 [SMILES: Cc1nc2c(C3=NOC(c4cc(Cl)cc(Cl)c4)(C(F)(F)F)C3)ccc(C(=O)NC3CS(=O)(=O)C3)c2o1] | 3.47 | [M + H]⁺ = 562 | C |

TABLE A-continued

| Comp No. | Structure | RT (min) | Molecular ion | LC-MS method |
|---|---|---|---|---|
| A27 | 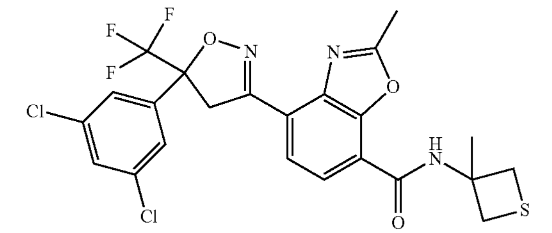 [SMILES: Cc1nc2c(C3=NOC(c4cc(Cl)cc(Cl)c4)(C(F)(F)F)C3)ccc(C(=O)NC3(C)CSC3)c2o1] | 4.12 | [M + H]⁺ = 544 | C |
| A28 | mixture of isomers | 3.18 | [M + H]⁺ = 546 | C |
| A29 | 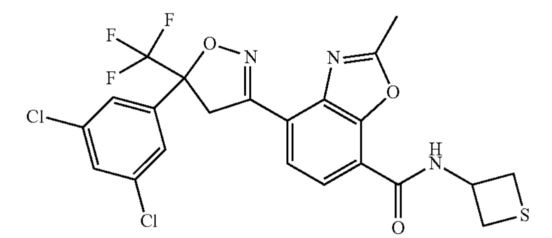 [SMILES: Cc1nc2c(C3=NOC(c4cc(Cl)cc(Cl)c4)(C(F)(F)F)C3)ccc(C(=O)NC3CSC3)c2o1] | 3.91 | [M + H]⁺ = 530 | C |
| A30 | 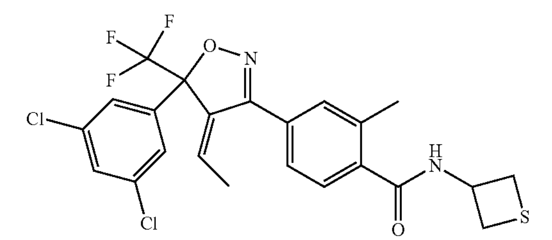 | 2.18 | [M + H + HCOOH]⁺ = 559/561/563 | E |
| A31 | 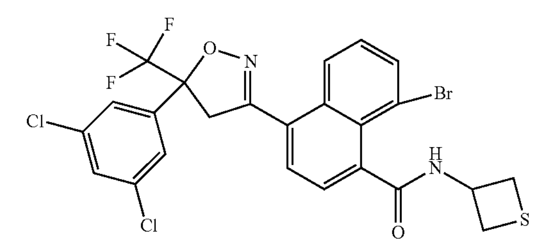 [SMILES: O=C(NC1CSC1)c1ccc(C2=NOC(c3cc(Cl)cc(Cl)c3)(C(F)(F)F)C2)c2cccc(Br)c12] | 2.26 | [M − H]⁻ = 539 | A |
| A32 | 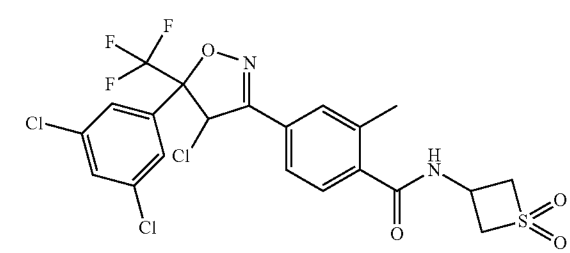 [SMILES: Cc1cc(C2=NOC(c3cc(Cl)cc(Cl)c3)(C(F)(F)F)C2Cl)ccc1C(=O)NC1CS(=O)(=O)C1] | 3.53 | [M + H]⁺ = 555 | E |

TABLE A-continued

| Comp No. | Structure | RT (min) | Molecular ion | LC-MS method |
|---|---|---|---|---|
| A33 | 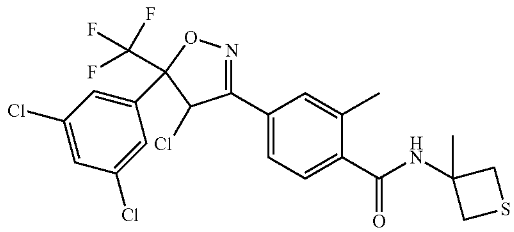 | 4.06 | [M + H]+ = 537 | E |
| A34 | mixture of isomers | 3.3 | [M + H]+ = 539 | E |
| A35 | 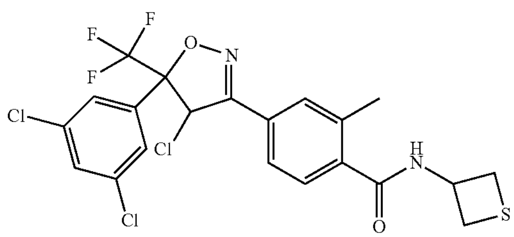 | 3.91 | [M + H]+ = 523 | E |
| A36 | 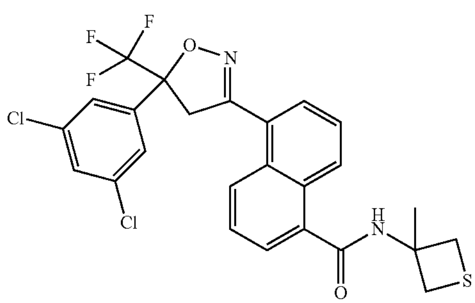 [SMILES: CC1(NC(=O)c2cccc3c(C4=NOC(c5cc(Cl)cc(Cl)c5)(C(F)(F)F)C4)cccc23)CSC1] | 4.05 | [M + H]+ = 539 | C |
| A37 | mixture of isomers | 3.27 | [M + H]+ = 540 | C |

TABLE A-continued

| Comp No. | Structure | RT (min) | Molecular ion | LC-MS method |
|---|---|---|---|---|
| A38 | 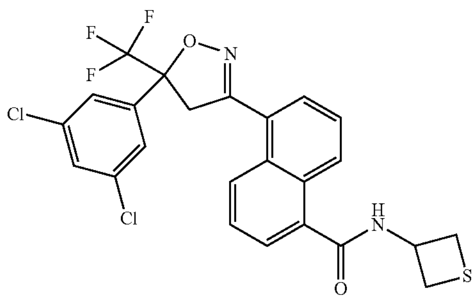 [SMILES: O=C(NC1CSC1)c1cccc2c(C3=NOC(c4cc(Cl)cc(Cl)c4)(C(F)(F)F)C3)cccc12] | 3.87 | [M + H]⁺ = 524 | C |
| A39 | 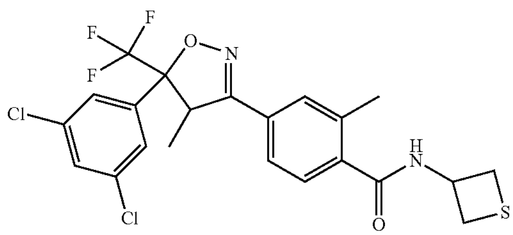 | 2.14 | [M + H]⁺ = 547/549 | F |
| A40 | 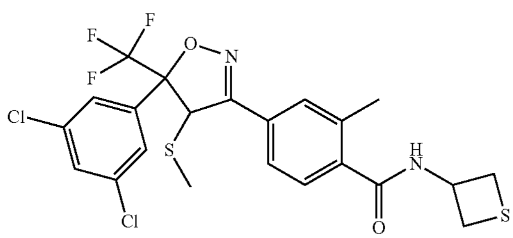 | 2.16 | [M + H]⁺ = 579/581 | F |
| A41 | 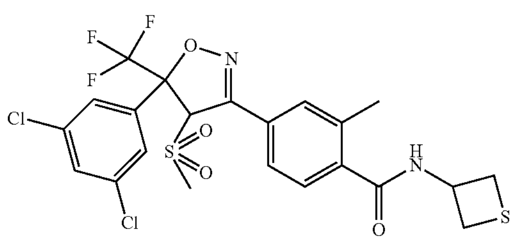 [SMILES: Cc1cc(C2=NOC(c3cc(Cl)cc(Cl)c3)(C(F)(F)F)C2S(C)(=O)=O)ccc1C(=O)NC1CSC1] | 2.05 | [M + H]⁺ = 565/567 | F |
| A42 | 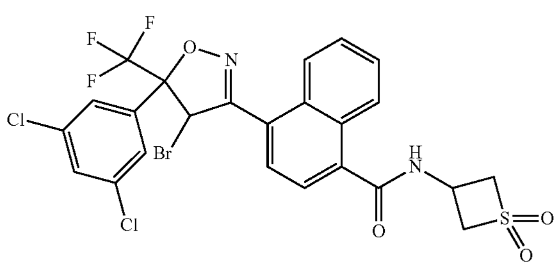 [SMILES: O=C(NC1CS(=O)(=O)C1)c1ccc(C2=NOC(c3cc(Cl)cc(Cl)c3)(C(F)(F)F)C2Br)c2ccccc12] | 2.06 | [M + H]⁺ = 635/637 | E |
| A43 | 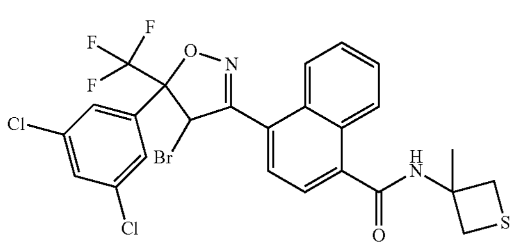 [SMILES: CC1(NC(=O)c2ccc(C3=NOC(c4cc(Cl)cc(Cl)c4)(C(F)(F)F)C3Br)c3ccccc23)CSC1] | 2.35 | [M + H]⁺ = 617/619 | E |

TABLE A-continued
| Comp No. | Structure | RT (min) | Molecular ion | LC-MS method |
|---|---|---|---|---|
| A44 | 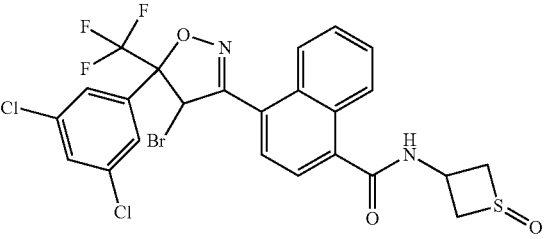 mixture of isomers | 1.94 | [M + H]+ = 619/621 | E |
| A45 | 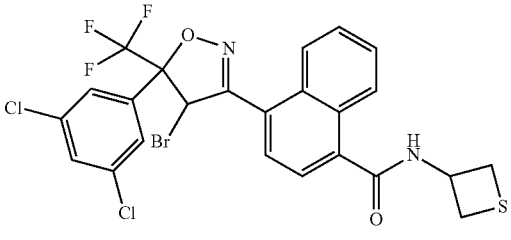 [SMILES: O=C(NC1CSC1)c1ccc(C2=NOC(c3cc(Cl)cc(Cl)c3)(C(F)(F)F)C2Br)c2ccccc12] | 2.15 | [M + H]+ = 603/605 | E |
| A46 | 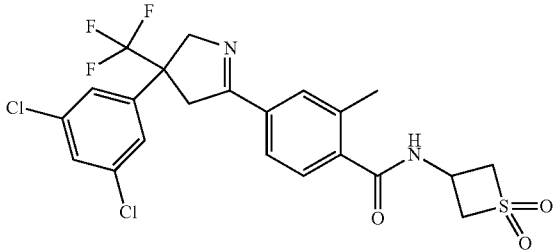 [SMILES: Cc1cc(C2=NCC(c3cc(Cl)cc(Cl)c3)(C(F)(F)F)C2)ccc1C(=O)NC1CS(=O)(=O)C1] | 3.04 | [M + H]+ = 519.0 | C |
| A47 | 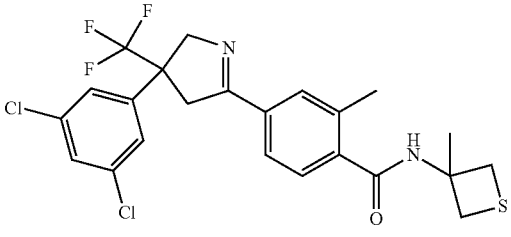 [SMILES: Cc1cc(C2=NCC(c3cc(Cl)cc(Cl)c3)(C(F)(F)F)C2)ccc1C(=O)NC1(C)CSC1] | 3.59 | [M + H]+ = 501.0 | C |
| A48 | 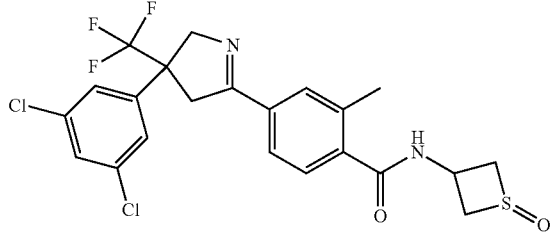 mixture of isomers | 2.82 | [M + H]+ = 503.0 | C |
| A49 | 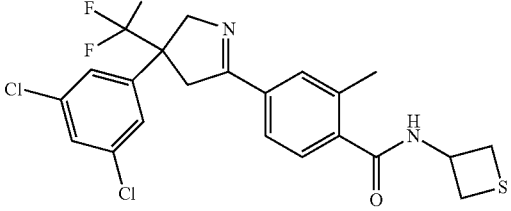 | 3.40 | [M + H]+ = 487.0 | C |

TABLE A-continued

| Comp No. | Structure | RT (min) | Molecular ion | LC-MS method |
|---|---|---|---|---|
| A50 | 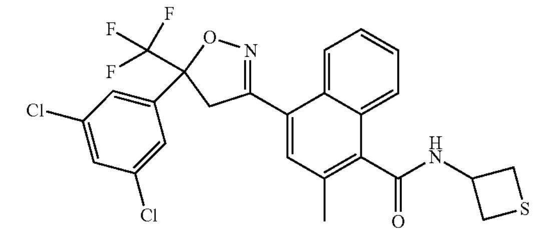 [SMILES: Cc1cc(C2=NOC(c3cc(Cl)cc(Cl)c3)(C(F)(F)F)C2)c2ccccc2c1C(=O)NC1CSC1] | 2.23 | [M − H]⁻ = 603/605 | A |
| A51 | 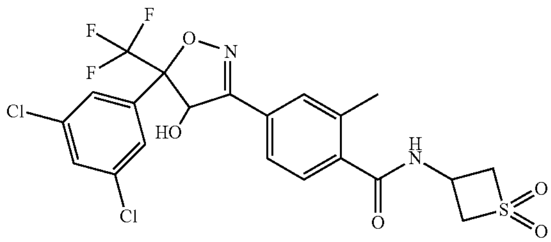 [SMILES: Cc1cc(C2=NOC(c3cc(Cl)cc(Cl)c3)(C(F)(F)F)C2O)ccc1C(=O)NC1CS(=O)(=O)C1] | 2.43 | [M + H]⁺ = 537 | B |
| A52 | 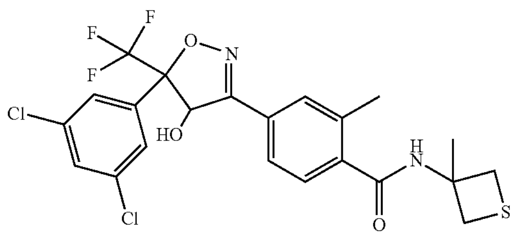 [SMILES: Cc1cc(C2=NOC(c3cc(Cl)cc(Cl)c3)(C(F)(F)F)C2O)ccc1C(=O)NC1(C)CSC1] | 2.93 | [M + H]⁺ = 519 | B |
| A53 | mixture of isomers | 2.17 | [M + H]⁺ = 521 | B |
| A54 | 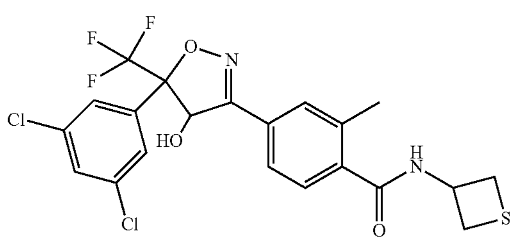 [SMILES: Cc1cc(C2=NOC(c3cc(Cl)cc(Cl)c3)(C(F)(F)F)C2O)ccc1C(=O)NC1CSC1] | 2.75 | [M + H]⁺ = 505 | B |
| A55 | 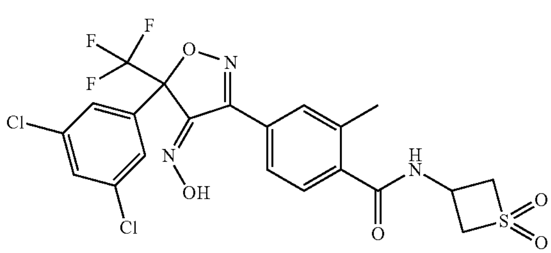 | 2.6 | [M + H]⁺ = 591 | B |

TABLE A-continued

| Comp No. | Structure | RT (min) | Molecular ion | LC-MS method |
|---|---|---|---|---|
| A56 | 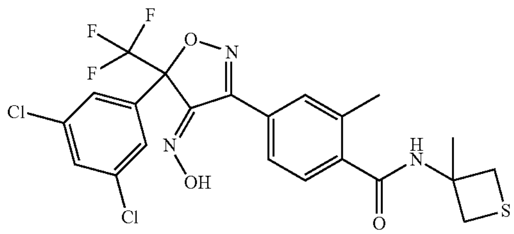 [SMILES: Cc1cc(C2=NOC(c3cc(Cl)cc(Cl)c3)(C(F)(F)F)/C2=N/O)ccc1C(=O)NC1(C)CSC1] | 3.11 | [M + H]⁺ = 532 | B |
| A57 | mixture of isomers | 2.35 | [M + H]⁺ = 534 | B |
| A58 | 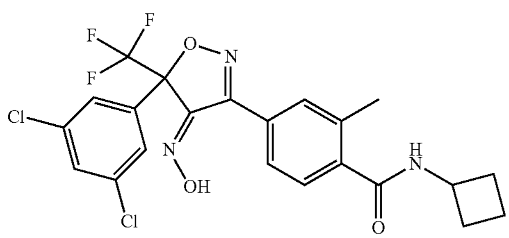 | 2.94 | [M + H]⁺ = 518 | B |
| A59 | 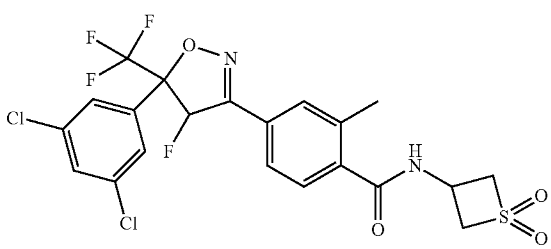 | 2.85 | [M + H]⁺ = 580 | B |
| A60 | 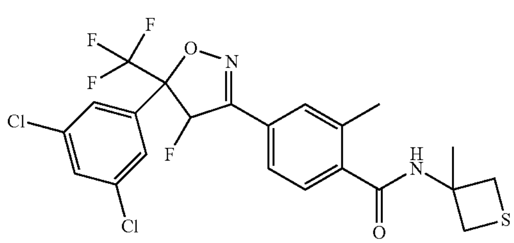 [SMILES: Cc1cc(C2=NOC(c3cc(Cl)cc(Cl)c3)(C(F)(F)F)C2F)ccc1C(=O)NC1(C)CSC1] | 3.4 | [M + H]⁺ = 521 | B |
| A61 | 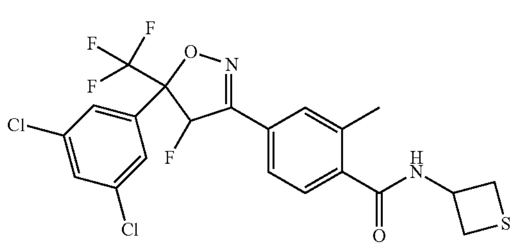 [SMILES: Cc1cc(C2=NOC(c3cc(Cl)cc(Cl)c3)(C(F)(F)F)C2F)ccc1C(=O)NC1CSC1] | 3.22 | [M + H]⁺ = 507 | B |

TABLE A-continued
| Comp No. | Structure | RT (min) | Molecular ion | LC-MS method |
|---|---|---|---|---|
| A62 | 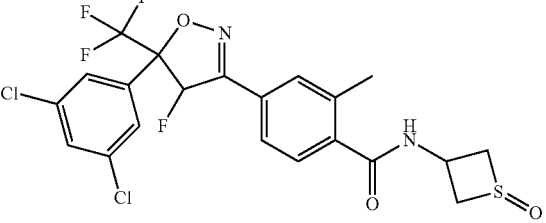 mixture of isomers | 2.55 | [M + H]⁺ = 523 | B |
| A63 | 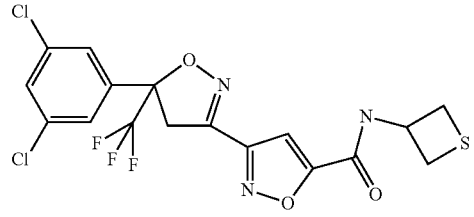 [SMILES: O=C(NC1CSC1)c1cc(C2=NOC(c3cc(Cl)cc(Cl)c3)(C(F)(F)F)C2)no1] | 4.7 | [M + H]⁺ = 466 | C |
| A64 | 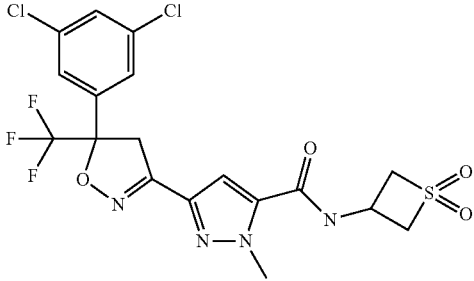 [SMILES: Cn1nc(C2=NOC(c3cc(Cl)cc(Cl)c3)(C(F)(F)F)C2)cc1C(=O)NC1CS(=O)(=O)C1] | 3.36 | [M + H]⁺ = 510.81 | C |
| A65 | 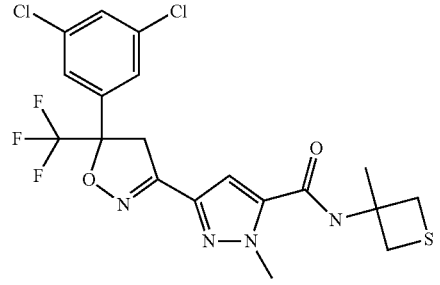 [SMILES: Cn1nc(C2=NOC(c3cc(Cl)cc(Cl)c3)(C(F)(F)F)C2)cc1C(=O)NC1(C)CSC1] | 3.94 | [M + H]⁺ = 492.87 | C |
| A66 | 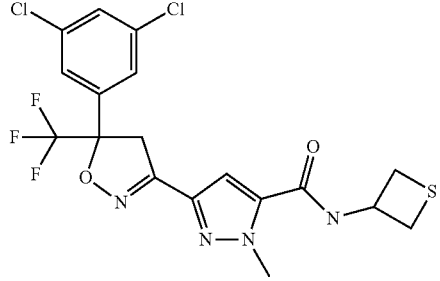 [SMILES: Cn1nc(C2=NOC(c3cc(Cl)cc(Cl)c3)(C(F)(F)F)C2)cc1C(=O)NC1CSC1] | 3.82 | [M + H]⁺ = 478.88 | C |

TABLE A-continued

| Comp No. | Structure | RT (min) | Molecular ion | LC-MS method |
|---|---|---|---|---|
| A67 | 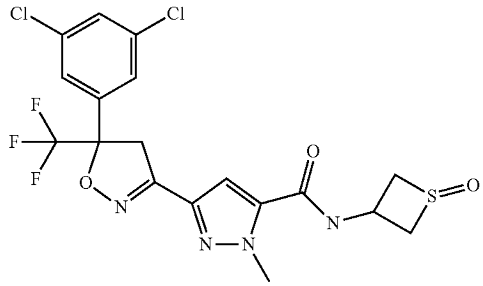 [SMILES: Cn1nc(C2=NOC(c3cc(Cl)cc(Cl)c3)(C(F)(F)F)C2)cc1C(=O)NC1CS(=O)C1] | 3.05 | [M + H]⁺ = 494.87 | C |
| A68 | 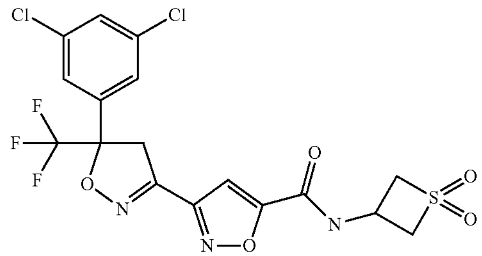 [SMILES: O=C(NC1CS(=O)(=O)C1)c1cc(C2=NOC(c3cc(Cl)cc(Cl)c3)(C(F)(F)F)C2)no1] | 4.48 | [M + H]⁺ = 498 | C |
| A69 | 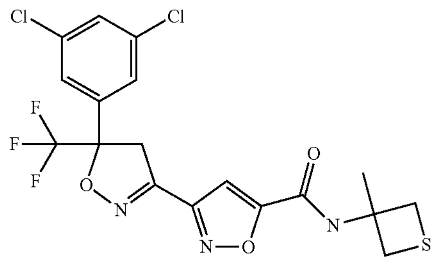 [SMILES: CC1(NC(=O)c2cc(C3=NOC(c4cc(Cl)cc(Cl)c4)(C(F)(F)F)C3)no2)CSC1] | 4.59 | [M + H]⁺ = 479.95 | C |
| A70 | 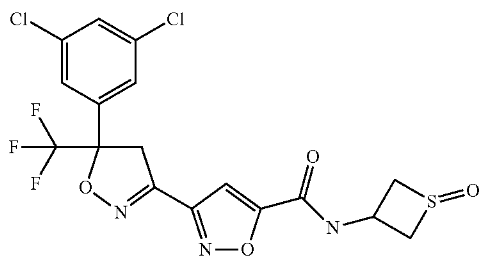 [SMILES: O=C(NC1CS(=O)C1)c1cc(C2=NOC(c3cc(Cl)cc(Cl)c3)(C(F)(F)F)C2)no1] | 4.13 | [M + H]⁺ = 481.84 | C |

Table A provides compounds of formula (I), their structure, retention time, molecular ion and the LC-MS method.

Example 17.1

3-Bromo-5-(3,5-dichloro-phenyl)-5-trifluoromethyl-4,5-dihydro-isoxazole

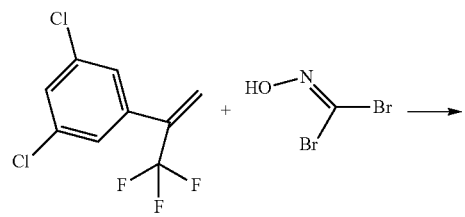

-continued

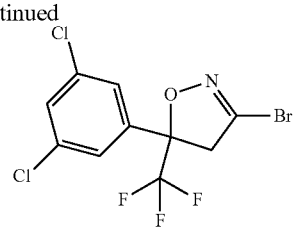

To a solution of dibromoformaldoxime (6.23 g, *Tetrahedron Lett.*, 1984, 487) in ethyl acetate (150 ml) was added 1,3-dichloro-5-(3,3,3-trifluoroprop-1-en-2-yl)benzene (6.3 g, prepared according to WO 2005/085216) and sodium bicarbonate (9.5 g). The reaction was stirred at room temperature for 96 h. Water was added, then the two layers were then separated. The aqueous layer was extracted with ethyl acetate and the combined organic layers were dried over sodium sulfate and concentrated to afford a white solid (6.23 g). 1H-NMR (CDCl$_3$, 400 MHz): 7.47-7.43 (m, 3H), 3.95 (d, 1H), 3.58 (d, 1H)

Example 17.2

3-Chloro-5-(3,5-dichloro-phenyl)-5-trifluoromethyl-4,5-dihydro-isoxazole

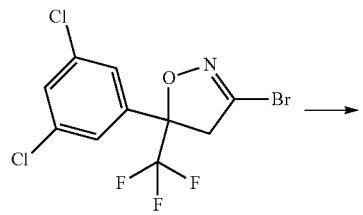

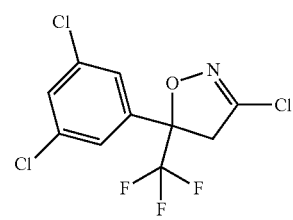

Concentrated hydrochloric acid (2.5 ml) was added on sodium chloride to generate dry HCl gas. This was pushed with argon to bubble into a solution of 3-bromo-5-(3,5-dichloro-phenyl)-5-trifluoromethyl-4,5-dihydro-isoxazole (182 mg) in tetrahydrofuran (5 ml). The reaction was stirred overnight at room temperature then water and diethyl ether ether were added. The two layers were then separated. The aqueous layer was extracted with diethyl etherether. The combined organic layers were washed with water, dried over dodium sulfate and concentrated to afford a residue, which was taken up in cyclohexane and filtered; The filtrate was concentrated in vacuo then dried under high vacuum to afford a white solid (132 mg). 1H-NMR (CDCl$_3$, 400 MHz): 7.44-7.37 (m, 3H), 3.84 (d, 1H), 3.50 (d, 1H)

Example 17.3

1-[5-(3,5-Dichloro-phenyl)-5-trifluoromethyl-4,5-dihydro-isoxazol-3-yl]-3-methyl-1H-pyrazole-4-carboxylic acid ethyl ester

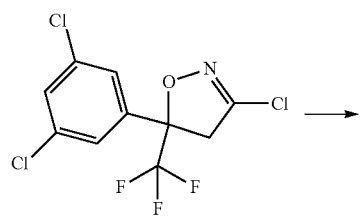

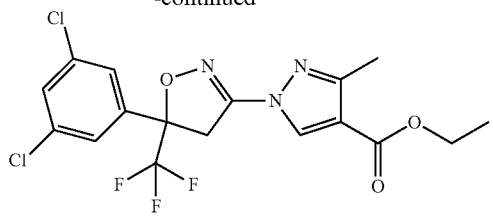

To a solution of 3-methyl-4-ethyl ester pyrazole (616 mg) in acetonitrile (15 ml) under argon was added sodium hydride (60% in oil, 160 mg). The reaction mixture was stirred for 1 hour at room temperature with addition of 5 ml tetrahydrofuran to help solubilising the nucleophile. 10 ml of the resulting solution was added slowly to a solution of chloroisoxazoline (Example 17.2, 630 mg) in acetonitrile (10 ml) at room temperature. The resulting red solution was stirred at rt for 30 min. 5 ml of the pyrazole sodium salt solution was added again and the mixture was stirred a further 1.5 hour. Another 0.2 ml of the pyrazole sodium salt solution was added and after 30 min the reaction was quenched by adding water and dichloromethane. The two layers were separated. The aqueous layer was extracted with dichloromethane. The combined organic layers were washed with brine, dried over Na2SO4 and concentrated. The crude residue was purified by column chromatography (from c-Hex (100%) to c-Hex:EtOAc (80:20)) to afford the title intermediate (872 mg) as the major regioisomer (along with 1-[5-(3,5-dichloro-phenyl)-5-trifluoromethyl-4,5-dihydro-isoxazol-3-yl]-5-methyl-1H-pyrazole-4-carboxylic acid ethyl ester). 1H-NMR (CDCl$_3$, 400 MHz): 8.5 (s, 1H), 7.5 (m, 2H), 7.45 (m, 1H), 4.35 (d, 1H), 4.30 (q, 2H), 3.95 (d, 1H), 2.50 (s, 3H), 1.35 (t, 3H).

Example 17.4

1-[5-(3,5-Dichloro-phenyl)-5-trifluoromethyl-4,5-dihydro-isoxazol-3-yl]-3-methyl-1H-pyrazole-4-carboxylic acid

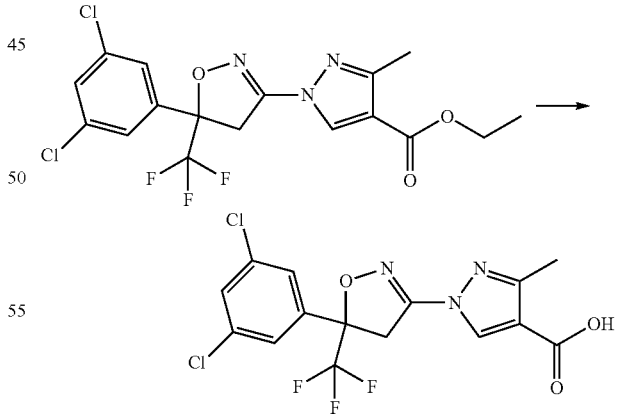

To a solution of ethyl ester of example 17.3 (493 mg) in 10 ml THF:water (4:1) was added sodium hydroxide (68 mg). The reaction mixture was stirred at room temperature for 3 hours before adding 2 ml of methanol. The reaction was stirred overnight before evaporation of the solvent in vacuo. The aqueous layer was extracted with ethyl acetate before being acidified. It was then extracted several times with ethyl acetate. The combined organic layers were dried over sodium sulfate and concentrated to afford a mixture of regioisomeric acids (224 mg, 3-methyl major and 5-methyl minor). 1H-NMR (CDCl₃, 400 MHz): 8.5 (s, 1H), 7.5 (m, 2H), 7.45 (m, 1H), 4.35 (d, 1H), 3.85 (d, 1H), 2.50 (s, 3H).

Example 18.1

1-[5-(3,5-Dichloro-phenyl)-5-trifluoromethyl-4,5-dihydro-isoxazol-3-yl]-1H-pyrazole-3-carboxylic acid methyl ester

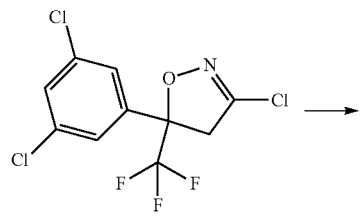

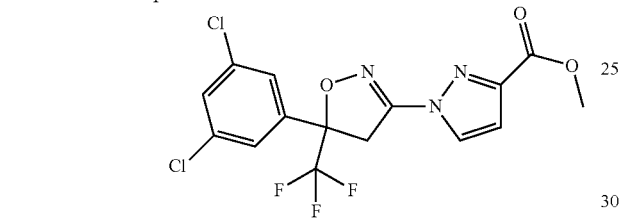

To a solution of pyrazole-3-carboxylic acid methyl ester (504 mg) in acetonitrile (25 ml) under argon was added sodium hydride (160 mg). The reaction mixture was stirred at room temperature for 1 h. 15 mf of this solution was added dropwise to a solution of chloroisoxazoline of example 17.2 (630 mg) in acetonitrile (10 ml). It was then stirred at room temperature for 1 h; 10 ml of pyrazole solution was added again and the mixture was stirred for 1.5 hour. The reaction was quenched by adding water and dichloromethane. The two layers were separated. The aqueous layer was extracted with dichloromethane. The combined organic layers were washed with brine, dried over sodium sulfate and concentrated. The crude residue was purified by column chromatography (from c-Hex (100%) to c-Hex:EtOAc (80:20)) to afford the title intermediate (680 mg). 1H-NMR (CDCl3, 400 MHz): 8.15 (s, 1H), 7.5 (m, 2H), 7.45 (m, 1H), 4.45 (d, 1H), 4.10 (d, 1H), 3.95 (s, 3H).

Example 18.2

1-[5-(3,5-Dichloro-phenyl)-5-trifluoromethyl-4,5-dihydro-isoxazol-3-yl]-1H-pyrazole-3-carboxylic acid

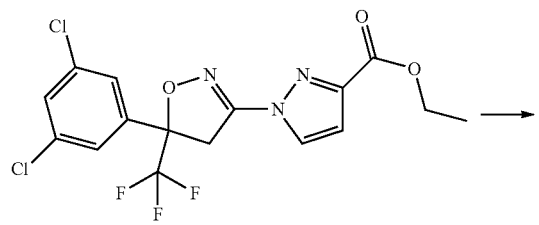

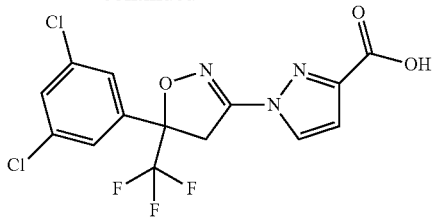

To a solution of methyl ester of example 18.1 (408 mg) in 5 ml THF:water (4:1) was added sodium hydroxide (60 mg). The reaction was stirred 2 hours at room temperature before evaporation of the solvent in vacuo. The aqueous layer was extracted with ethyl acetate before being acidified. It was then extracted several times with ethyl acetate. The combined organic layers were dried over sodium sulfate and concentrated to afford the title acid (369 mg) as a yellowish solid. 1H-NMR (CDCl₃, 400 MHz): 8.20 (s, 1H), 7.50 (m, 2H), 7.45 (m, 1H), 7.05 (s, 1H), 4.45 (d, 1H), 4.10 (d, 1H).

Example 19.1

1-[5-(3,5-Dichloro-phenyl)-5-trifluoromethyl-4,5-dihydro-isoxazol-3-yl]-1H-pyrazole-4-carboxylic acid methyl ester

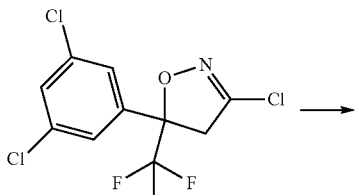

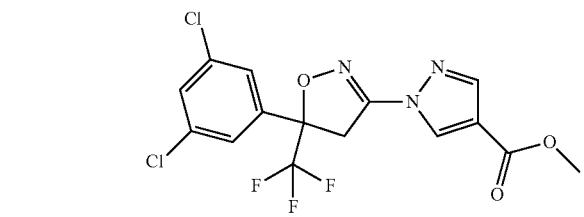

To a solution of pyrazole-4-carboxylic acid methyl ester (756 mg) in acetonitrile (30 ml) under argon was added sodium hydride (240 mg). The reaction mixture was stirred at room temperature for 1 h. 15 mf of this solution was added dropwise to a solution of chloroisoxazoline of example 17.2 (630 mg) in acetonitrile (10 ml). It was then stirred at room temperature for 1 h; 15 ml of pyrazole solution was added again and the mixture was stirred over the weekend. The reaction was quenched by adding water and dichloromethane. The two layers were separated. The aqueous layer was extracted with dichloromethane. The combined organic layers were washed with brine, dried over sodium sulfate and concentrated. The crude residue was purified by column chromatography (from c-Hex (100%) to c-Hex:EtOAc (80:20)) to afford the title intermediate (810 mg) as a yellow solid. 1H-NMR (CDCl3, 400 MHz): 8.60 (s, 1H), 8.10 (s, 1H), 7.5 (m, 2H), 7.45 (m, 1H), 4.35 (d, 1H), 4.00 (d, 1H), 3.75 (s, 3H).

Example 19.2

1-[5-(3,5-Dichloro-phenyl)-5-trifluoromethyl-4,5-dihydro-isoxazol-3-yl]-1H-pyrazole-4-carboxylic acid

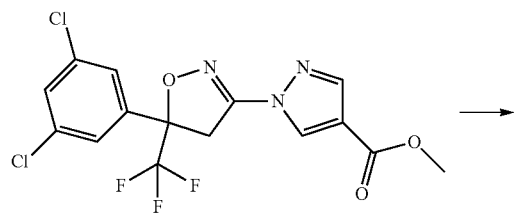

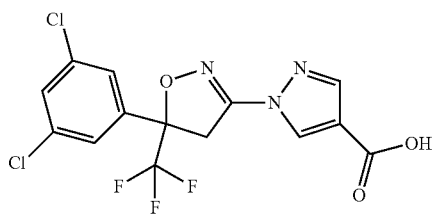

To a solution of methyl ester of example 19.1 (513 mg) in 12.5 ml THF:water (4:1) was added sodium hydroxide (75 mg). The reaction mixture was stirred at room temperature for 3 hours before adding 2 ml of methanol. The reaction was stirred overnight before evaporation of the solvent in vacuo. The aqueous layer was extracted with ethyl acetate before being acidified. It was then extracted several times with ethyl acetate. The combined organic layers were dried over sodium sulfate and concentrated to afford the title acid (452 mg) as a yellow solid. 1H-NMR (CDCl$_3$, 400 MHz): 8.55 (s, 1H), 8.05 (s, 1H), 7.50 (m, 2H), 7.45 (m, 1H), 4.35 (d, 1H), 4.00 (d, 1H).

Example 19.3

Method C for Preparing the Compounds of the Invention from a Carboxylic Acid

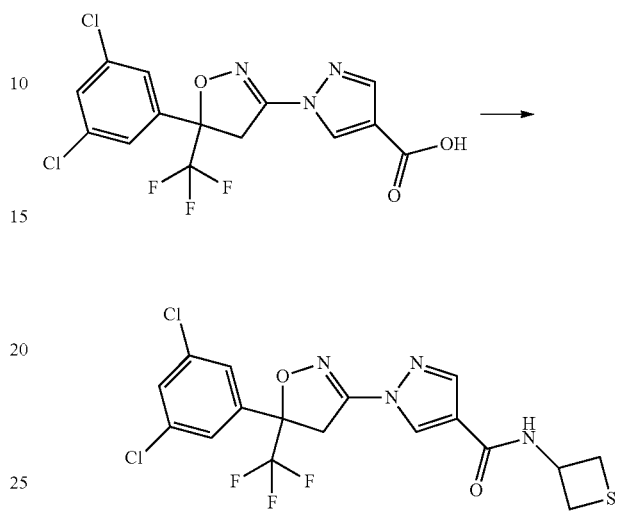

To a solution/suspension of the appropriate carboxylic acid, for example, 1-[5-(3,5-dichloro-phenyl)-5-trifluoromethyl-4,5-dihydro-isoxazol-3-yl]-1H-pyrazole-4-carboxylic acid (example 19.2, 98 mg) in dichloromethane (10 ml) was added the appropriate amine, for example, thietan-3-ylamine (trifluoracetic acid salt, 118 mg), O-(Benzotriazol-1-yl)-N,N,N',N'-tetramethyluronium tetrafluoroborate (TBTU) (80 mg) and triethylamine (0.125 ml). The resulting mixture was stirred at rt overnight. It was then quenched with aqueous diluted hydrochloric acid. The organic layer was washed with water before being dried over sodium sulfate and concentrated. The residue was purified by column chromatography on silica gel (eluent: from c-Hex:EA (95:5) to c-Hex:EA (75:25)) to afford Compound No. B4 of Table B (72 mg) as a colorless solid. M.p. 85-87° C.

This method was used to make:
Compound Nos. B1, B2 of Table B from 1-[5-(3,5-Dichloro-phenyl)-5-trifluoromethyl-4,5-dihydro-isoxazol-3-yl]-3-methyl (5-methyl regioisomer)-1H-pyrazole-4-carboxylic acid (preparation described in Example 17.4),
Compound Nos. B3 of Table B from 1-[5-(3,5-Dichloro-phenyl)-5-trifluoromethyl-4,5-dihydro-isoxazol-3-yl]-1H-pyrazole-3-carboxylic acid (preparation described in Example 18.2),

TABLE B

| Comp No. | Structure | M.p. | 1H-NMR |
|---|---|---|---|
| B1 | ![structure] | 177-180 °C. | (CDCl$_3$, 400 Mhz): 8.32 (s, 1H), 7.50 (m, 2H), 7.45 (m, 1H), 6.21 (br d, 1H), 5.47 (m, 1H), 4.30 (d, 1H), 3.95 (d, 1H), 3.40 (m, 4H), 2.50 (s, 3H). |

TABLE B-continued

| Comp No. | Structure | M.p. | ¹H-NMR |
|---|---|---|---|
| B2 | [structure: 3,5-dichlorophenyl-CF3-isoxazoline linked to methyl-pyrazole-carboxamide-N-thietanyl] | 77 °C. | (CDCl₃, 400 Mhz): 7.78 (s, 1H), 7.50 (m, 2H), 7.45 (m, 1H), 6.15 (br d, 1H), 5.39 (m, 1H), 4.36 (d, 1H), 4.00 (d, 1H), 3.40 (m, 4H), 2.85 (s, 3H). |
| B3 | [structure: 3,5-dichlorophenyl-CF3-isoxazoline linked to pyrazole-carboxamide-N-thietanyl] | 77-80 °C. | (CDCl₃, 400 Mhz): 8.12 (s, 1H), 7.50 (m, 2H), 7.45 (m, 1H), 7.19 (br d, 1H), 7.00 (s, 1H), 5.42 (m, 1H), 4.39 (d, 1H), 4.00 (d, 1H), 3.45 (m, 4H), 2.50 (s, 3H). |
| B4 | [structure: 3,5-dichlorophenyl-CF3-isoxazoline linked to pyrazole-carboxamide-N-thietanyl] | 85-87 °C. | (CDCl₃, 400 Mhz): 8.49 (s, 1H), 7.98 (s, 1H), 7.50 (m, 2H), 7.45 (m, 1H), 6.22 (br d, 1H), 5.40 (m, 1H), 4.32 (d, 1H), 3.98 (d, 1H), 3.42 (m, 4H) |

Table B provides compounds of formula (I), their structure, melting points and ¹H-NMR data.

Biological Examples

This Example illustrates the insecticidal and acaricidal properties of compounds of formula (I). The tests were performed as follows:

*Spodoptera littoralis* (Egyptian cotton leafworm):
Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT). The following compound gave at least 80% control of *Spodoptera littoralis*: A1, A2, A5, A6, A7, A8, A10, A11, A12, A13, A14, A15, A16, A17, A18, A19, A21, A22, A23, A24, A25, A30, A31, A32, A33, A34, A35, A39, A40, A41 A42, A43, A44, A45, A46, A47, A48, A49, A50, A51, A53, A54, A55, A59, A60, A61, A62.

*Heliothis virescens* (Tobacco budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.
The following compound gave at least 80% control of *Heliothis virescens*: A1, A2, A3, A4, A5, A6, A7, A8, A10, A11, A12, A13, A14, A15, A16, A18, A19, A21, A22, A24, A25, A30, A31, A32, A33, A34, A35, A37, A38, A39, A40, A42, A43, A44, A45, A46, A47, A48, A49, A50, A51, A55, AA57, A58, A59, A60, A61, A62.

*Plutella xylostella* (Diamond back moth):
24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compound gave at least 80% control of *Plutella xylostella*: A1, A2, A5, A6, A7, A8, A9, A10, A11, A12, A13, A14, A15, A16, A17, A18, A19, A20, A21, A22, A24, A25, A30, A31, A32, A33, A34, A35, A37, A38, A39, A40, A42, A43, A44, A45, A46, A47, A48, A49, A50, A51, A52, A53, A54, A55, A57, A58, A59, A60, A61, A62, B3.

*Diabrotica balteata* (Corn root worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.
The following compound gave at least 80% control of *Diabrotica balteata*: A1, A2, A5, A6, A7, A10, A11, A12, A13, A14, A15, A16, A17, A18, A19, A21, A22, A24, A25, A30, A31, A32, A33, A34, A35, A38, A39, A40, A42, A43, A44, A45, A46, A47, A48, A49, A50, A59, A60, A61, A62.

*Thrips tabaci* (Onion thrips):
Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.
The following compounds gave at least 80% control of *Thrips tabaci*: A1, A2, A5, A6, A7, A8, A10, A12, A13, A14, A15, A16, A17, A18, A19, A21, A24, A25, A30, A31, A32, A33, A34, A35, A39, A42, A43, A44, A45, A46, A47, A48, A49, A50, A51, A53, A54, A57, A58, A59, A60, A61, A62.

*Tetranychus urticae* (Two-spotted spider mite):
Bean leaf discs on agar in 24-well microtiter plates were sprayed with test solutions at an application rate of 200 ppm.

After drying, the leaf discs are infested with mite populations of mixed ages. 8 days later, discs are checked for egg mortality, larval mortality, and adult mortality.

The following compound gave at least 80% control of *Tetranychus urticae*: A1, A2, A4, A5, A6, A7, A8, A10, A11, A12, A13, A14, A15, A16, A17, A18, A19, A20, A21, A22, A30, A31, A32, A33, A34, A35, A39, A40, A41, A42, A43, A44, A45, A46, A47, A48, A49, A50, A51, A53, A54, A55, A57, A59, A60, A61, A62.

Compound Nos. A26, A27, A28, A29, A36 and A56 of Table A were tested using the same protocols and showed little or no effect on mortality, feeding behavior, or growth regulation under the test conditions.

The invention claimed is:
1. A compound of formula (I)

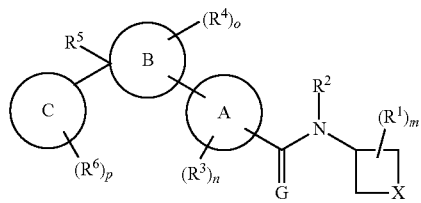

where
A is aryl or heteroaryl;
B is a saturated or partially unsaturated heterocyclyl;
C is a group of formula (C.I)

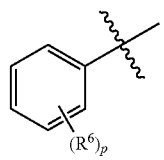

where
p is 1, 2, 3, 4 or 5, and
each $R^6$ is independently halogen, cyano, nitro, $C_1$-$C_8$alkyl, $C_1$-$C_8$haloalkyl, $C_1$-$C_8$alkoxy-, $C_1$-$C_8$haloalkoxy-, $C_1$-$C_8$alkoxycarbonyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;
G is oxygen or sulfur;
m is 0, 1, 2, 3, 4 or 5;
n is 0, 1, 2, 3, 4 or 5;
o is 0, 1, 2, 3, 4 or 5;
p is 1, 2, 3, 4 or 5;
each $R^1$ is independently $C_1$-$C_8$alkyl;
$R^2$ is hydrogen, $C_1$-$C_8$alkyl, $C_1$-$C_8$alkylcarbonyl-, or $C_1$-$C_8$alkoxycarbonyl-;
each $R^3$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_3$-$C_{10}$cycloalkyl, $C_1$-$C_8$alkoxy-, $C_1$-$C_8$haloalkoxy-, or $C_1$-$C_8$alkoxycarbonyl-;
each $R^4$ is independently halogen, cyano, $C_1$-$C_8$alkyl, $C_1$-$C_8$haloalkyl, hydroxy, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-, or
if two $R^4$ are attached to the same carbon atom the two $R^4$ together form =O, =N—$OR^7$ or =$CR^8R^9$;
$R^5$ is $C_1$-$C_8$haloalkyl;
each $R^6$ is independently halogen, cyano, nitro, $C_1$-$C_8$alkyl, $C_1$-$C_8$haloalkyl, $C_1$-$C_8$alkoxy-, $C_1$-$C_8$haloalkoxy-, $C_1$-$C_8$alkoxycarbonyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
X is S, SO, $SO_2$, S($NR^{10}$) or SO($NR^{10}$);
$R^7$ is hydrogen or $C_1$-$C_4$alkyl;
$R^8$ and $R^9$ are independently of each other hydrogen or $C_1$-$C_4$alkyl;
$R^{10}$ is hydrogen, cyano, nitro, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene- where the aryl moiety is substituted by one to three $R^{11}$, or heteroaryl-$C_1$-$C_4$alkylene- or heteroaryl-$C_1$-$C_4$alkylene- where the heteroaryl moiety is substituted by one to three $R^{11}$, aryl or aryl substituted by one to five $R^{11}$, or heteroaryl or heteroaryl substituted by one to five $R^{11}$; and
each $R^{11}$ is independently halogen, cyano, nitro, $C_1$-$C_8$alkyl, $C_1$-$C_8$haloalkyl, $C_1$-$C_8$alkoxy or $C_1$-$C_8$haloalkoxy, or $C_1$-$C_8$alkoxycarbonyl-;
or a salt or an N-oxide thereof;
provided that if A is a group of formula (A.I), (A.II), (A.III), (A.IV) or (A.V)

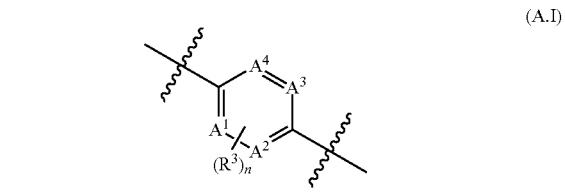

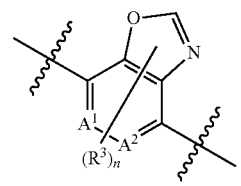

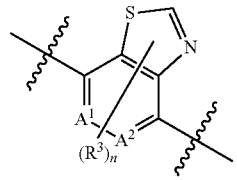

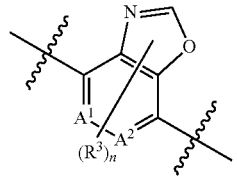

-continued (A.V)

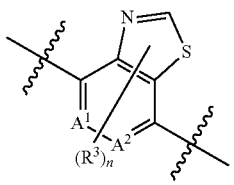

where

A$^1$, A$^2$, A$^3$ and A$^4$ are independently of each other C—H or nitrogen;

n is 0, 1, 2, 3, 4 or 5, and each R$^3$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_3$-C$_{10}$cycloalkyl, C$_1$-C$_8$alkoxy-, C$_1$-C$_8$haloalkoxy-, or C$_1$-C$_8$alkoxycarbonyl-, B is not a group of formula (B.VI)

(B.VI)

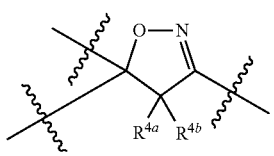

where R$^{4a}$ and R$^{4b}$ are both hydrogen.

2. A compound according to claim 1 where A is a group of formula (A.I), (A.VI), (A.VII) or (A.VIII)

(A.I)

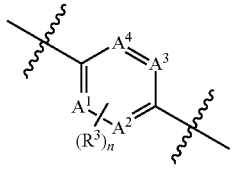

(A.VI)

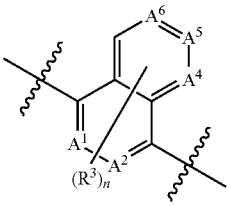

(A.VII)

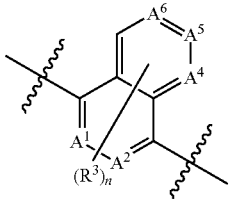

-continued (A.VIII)

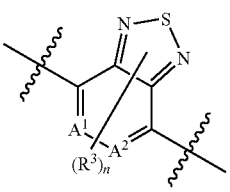

where

A$^1$, A$^2$, A$^3$, A$^4$, A$^5$ and A$^6$ are independently of each other C—H or nitrogen;

n is 0, 1, 2, 3, 4 or 5, and each R$^3$ is independently halogen, cyano, nitro, C$_1$-C$_8$alkyl, C$_1$-C$_8$haloalkyl, C$_2$-C$_8$alkenyl, C$_2$C$_8$haloalkenyl, C$_2$-C$_8$alkynyl, C$_3$-C$_{10}$cycloalkyl, C$_1$-C$_8$alkoxy-, C$_1$-C$_8$haloalkoxy-, or C$_1$-C$_8$alkoxycarbonyl-.

3. A compound according to claim 1 where B is a group of formula (B.I), (B.II), (B.III), (B.IV), (B.V), (B.VI) or (B.VII)

(B.I)

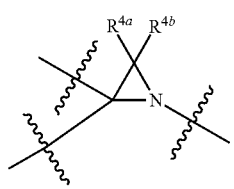

(B.II)

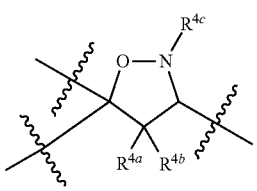

(B.III)

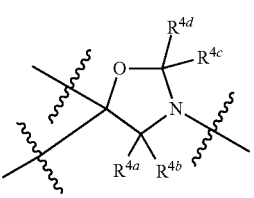

(B.IV)

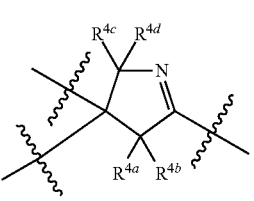

(B.V)

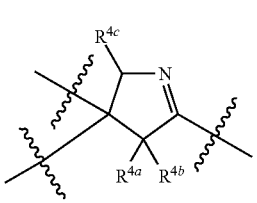

-continued (B.VI)

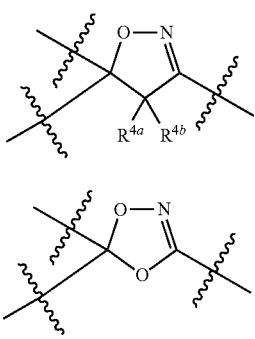

(B.VII)

where
$R^{4a}$, $R^{4b}$, $R^{4c}$ and $R^{4d}$ are independently of each other hydrogen, halogen, cyano, $C_1$-$C_8$alkyl, $C_1$-$C_8$haloalkyl, hydroxy, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-, or $R^{4a}$ and $R^{4b}$ and/or $R^{4c}$ and $R^{4d}$ when attached to the same carbon atom together form =O, N=$OR^7$ or =$CR^8R^9$.

4. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

5. An insecticidal, acaricidal, nematicidal or molluscicidal composition comprising an insecticidally, acaricidally, nematicidally or molluscicidally effective amount of a compound of formula (I) as defined in claim 1.

* * * * *